United States Patent
Buhimschi et al.

(10) Patent No.: US 11,125,758 B2
(45) Date of Patent: Sep. 21, 2021

(54) METHODS AND KITS FOR DETECTING MISFOLDED PROTEINS

(71) Applicant: Yale University, New Haven, CT (US)

(72) Inventors: Catalin S. Buhimschi, Columbus, OH (US); Irina Buhimschi, Columbus, OH (US); Charles G. Glabe, Irvine, CA (US)

(73) Assignees: Yale University, New Haven, CT (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/679,285

(22) Filed: Aug. 17, 2017

(65) Prior Publication Data

US 2017/0356920 A1      Dec. 14, 2017

Related U.S. Application Data

(63) Continuation of application No. 14/849,670, filed on Sep. 10, 2015, now Pat. No. 10,048,276, which is a continuation of application No. 13/126,757, filed as application No. PCT/US2009/005957 on Nov. 2, 2009, now Pat. No. 9,229,009.

(60) Provisional application No. 61/206,534, filed on Jan. 29, 2009, provisional application No. 61/197,914, filed on Oct. 31, 2008.

(51) Int. Cl.
| | | |
|---|---|---|
| *G01N 33/53* | (2006.01) | |
| *G01N 33/68* | (2006.01) | |
| *G01N 33/52* | (2006.01) | |

(52) U.S. Cl.
CPC ........... *G01N 33/689* (2013.01); *G01N 33/52* (2013.01); *G01N 33/53* (2013.01); *G01N 33/68* (2013.01); *G01N 33/6803* (2013.01); *G01N 33/6857* (2013.01); *G01N 33/6866* (2013.01); *G01N 2333/4703* (2013.01); *G01N 2333/8125* (2013.01); *G01N 2333/90287* (2013.01); *G01N 2800/368* (2013.01)

(58) Field of Classification Search
CPC ....... G01N 33/689; G01N 33/52; G01N 33/53
See application file for complete search history.

(56) References Cited

U.S. PATENT DOCUMENTS

| | | | |
|---|---|---|---|
| 4,444,879 | A | 4/1984 | Foster et al. |
| 5,998,216 | A | 12/1999 | O'Donnell |
| 6,444,435 | B1 | 9/2002 | Christner |
| 7,727,733 | B2 | 6/2010 | Buhimschi et al. |
| 7,935,496 | B2 | 5/2011 | Buhimschi et al. |
| 8,263,342 | B2 | 9/2012 | Buhimschi et al. |
| 9,229,009 | B2 | 1/2016 | Buhimschi et al. |
| 10,048,276 | B2 | 8/2018 | Buhimschi et al. |
| 10,324,094 | B2 | 6/2019 | Buhimschi et al. |
| 2005/0051052 | A1 | 3/2005 | Vanmaele et al. |
| 2011/0065139 | A1 | 3/2011 | Mullerad et al. |
| 2011/0280863 | A1 | 11/2011 | Buhimschi et al. |
| 2015/0293115 | A1 | 10/2015 | Buhimschi et al. |
| 2016/0097775 | A1 | 4/2016 | Buhimschi et al. |

FOREIGN PATENT DOCUMENTS

| | | |
|---|---|---|
| CN | 102483418 A | 5/2012 |
| CN | 103012599 A | 4/2013 |
| EP | 1 733 762 A1 | 12/2006 |
| WO | WO 1998/28006 A | 7/1998 |
| WO | WO 2004/008946 A | 1/2004 |
| WO | WO 2004/024090 A2 | 3/2004 |
| WO | WO 2007/051069 A | 5/2007 |
| WO | WO 2007/053161 A | 5/2007 |
| WO | WO 2010/062377 A | 6/2010 |
| WO | WO 2015/157704 A | 10/2015 |

OTHER PUBLICATIONS

U.S. Appl. No. 14/683,908, filed Apr. 10, 2015, Buhimschi et al.
PCT/US2009/005957, dated May 26, 2010, International Search Report and Written Opinion.
PCT/US2009/005957, dated May 12, 2011, International Preliminary Report on Patentability.
PCT/US2015/025432, dated Mar. 15, 2016, International Search Report and Written Opinion.
PCT/US2015/025432, dated Oct. 20, 2016, International Preliminary Report on Patentability.
Abou-Zahr et al., Antenatal care in developing countries: promises, achievements and missed opportunities: an analysis of trends, levels and differentials, 1990-2001. World Health Organization, Geneva, Switzerland, 2003. 36 pages.
ACOG Committee on Obstetric Practice. ACOG practice bulletin. Diagnosis and management of preeclampsia and eclampsia. No. 33, Jan. 2002. American College of Obstetricians and Gynecologists. Int J Gynaecol Obstet. Apr. 2002;77(1):67-75.
Buhimschi et al., 239: Preeclampsia is a disease characterized by specific supramuolecular aggregates of misfolded proteins and congophilia. Am J Obstet Gynecol. 2008 199(6): S78. Abstract Only.
Buhimschi et al., Protein misfolding, congophilia, oligomerization, and defective amyloid processing in preeclampsia. Sci Transl Med. Jul. 16, 2014;6(245):245ra92. doi: 10.1126/scitranslmed.3008808.
Buhimschi et al., Proteomic profiling of urine identifies specific fragments of SERPINA1 and albumin as biomarkers of preeclampsia. Am J Obstet Gynecol. Nov. 2008;199(5):551.e1-16. doi: 10.1016/j.ajog.2008.07.006.
Buhimschi et al., The nitric oxide pathway in pre-eclampsia: pathophysiological implications. Hum Reprod Update. Jan.-Feb. 1998;4(1):25-42. Review.
Buhimschi et al., Urinary angiogenic factors cluster hypertensive disorders and identify women with severe preeclampsia. Am J Obstet Gynecol. Mar. 2005;192(3):734-41.
Carrell et al., Alpha1-antitrypsin deficiency—a model for conformational diseases. N Engl J Med. Jan. 3, 2002;346(1):45-53. Review.

(Continued)

*Primary Examiner* — Robert C Hayes
(74) *Attorney, Agent, or Firm* — Wolf, Greenfield & Sacks, P.C.

(57) ABSTRACT

Methods, kits and compounds are provided that relate to the diagnosis, treatment, and/or prevention of preeclampsia.

10 Claims, 19 Drawing Sheets

Specification includes a Sequence Listing.

(56) References Cited

OTHER PUBLICATIONS

Chang et al., Identification of a 4-mer peptide inhibitor that effectively blocks the polymerization of pathogenic Z alpha1-antitrypsin. Am J Respir Cell Mol Biol. Nov. 2006;35(5):540-8. Epub Jun. 15, 2006.

Devlin et al., Prevention of polymerization of M and Z alpha1-Antitrypsin (alpha1-AT) with trimethylamine N-oxide. Implications for the treatment of alpha1-at deficiency. Am J Respir Cell Mol Biol. Jun. 2001;24(6):727-32.

Eiland et al., Preeclampsia 2012. J Pregnancy. 2012;2012:586578. doi: 10.1155/2012/586578. Epub Jul. 11, 2012. Review.

Engel et al., Remote real-time monitoring of free flaps via smartphone photography and 3G wireless Internet: a prospective study evidencing diagnostic accuracy. Microsurgery. Nov. 2011;31(8):589-95. doi: 10.1002/micr.20921. Epub Aug. 24, 2011.

Faas et al., A new animal model for human preeclampsia: ultra-low-dose endotoxin infusion in pregnant rats. Am J Obstet Gynecol. Jul. 1994;171(1):158-64.

Frid et al., Congo red and protein aggregation in neurodegenerative diseases. Brain Res Rev. Jan. 2007;53(1):135-60. Epub Sep. 7, 2006. Review.

Halimi et al., Prion urine comprises a glycosaminoglycan-light chain IgG complex that can be stained by Congo red. J Virol Methods. May 2006;133(2):205-10. Epub Jan. 4, 2006.

Harlow et al., The diversity of diagnoses of preeclampsia. Hypertens Pregnancy. 2001;20(1):57-67. Review.

Hinberg et al., Sensitivity of in vitro diagnostic dipstick tests to urinary protein. Clin Biochem. Apr. 1978;11(2):62-4.

Howie et al., Optical properties of amyloid stained by Congo red: history and mechanisms. Micron. Apr. 2009;40(3):285-301. doi:10.1016/j.micron.2008.10.002. Epub Oct. 15, 2008. Review.

Ikonomovic et al., X-34 labeling of abnormal protein aggregates during the progression of Alzheimer's disease. Methods Enzymol. 2006;412:123-44. Review.

Jonathan et al., Investigating a smartphone imaging unit for photoplethysmography. Physiol Meas. Nov. 2010;31(11):N79-83. doi: 10.1088/0967-3334/31/11/N01. Epub Sep. 24, 2010.

Joundi et al., Rapid tremor frequency assessment with the iPhone accelerometer. Parkinsonism Relat Disord. May 2011;17(4):288-90. doi: 10.1016/j.parkreldis.2011.01.001. Epub Feb. 5, 2011.

Kayed et al., Annular protofibrils are a structurally and functionally distinct type of amyloid oligomer. J Biol Chem. Feb. 13, 2009;284(7):4230-7. doi: 10.1074/jbc.M808591200. Epub Dec. 18, 2008.

Khan et al., WHO analysis of causes of maternal death: a systematic review. Lancet. Apr. 1, 2006;367(9516):1066-74. Review.

Klunk et al., Quantifying amyloid beta-peptide (Abeta) aggregation using the Congo red-Abeta (CR-abeta) spectrophotometric assay. Anal Biochem. Jan. 1, 1999;266(1):66-76.

Lemoyne et al., Implementation of an iPhone as a wireless accelerometer for quantifying gait characteristics. Conf Proc IEEE Eng Med Biol Soc. 2010;2010:3847-51. doi: 10.1109/IEMBS.2010.5627699.

Lemoyne et al., Implementation of an iPhone for characterizing Parkinson's disease tremor through a wireless accelerometer application. Conf Proc IEEE Eng Med Biol Soc. 2010;2010:4954-8. doi: 10.1109/IEMBS.2010.5627240.

Levine et al., Circulating angiogenic factors and the risk of preeclampsia. N Engl J Med. Feb. 12, 2004;350(7):672-83. Epub Feb. 5, 2004.

Levine et al., Urinary placental growth factor and risk of preeclampsia. JAMA. Jan. 5, 2005;293(1):77-85.

Linke, Highly sensitive diagnosis of amyloid and various amyloid syndromes using Congo red fluorescence. Virchows Arch. May 2000;436(5):439-48.

Lomas et al., Alpha1-antitrypsin polymerization and the serpinopathies: pathobiology and prospects for therapy. J Clin Invest. Dec. 2002;110(11):1585-90. Review.

Maisnar et al., The problems of proteinuria measurement in urine with presence of Bence Jones protein. Clin Biochem. Apr. 2011;44(5-6):403-5. doi: 10.1016/j.clinbiochem.2011.01.008. Epub Feb. 1, 2011.

Maynard et al., Excess placental soluble fms-like tyrosine kinase 1 (sFlt1) may contribute to endothelial dysfunction, hypertension, and proteinuria in preeclampsia. J Clin Invest. Mar. 2003;111(5):649-58.

Murray et al., The clinical utility of routine urinalysis in pregnancy: a prospective study. Med J Aust. Nov. 4, 2002;177(9):477-80.

Oliver et al., Activation of the receptor for advanced glycation end products system in women with severe preeclampsia. J Clin Endocrinol Metab. Mar. 2011;96(3):689-98. doi: 10.1210/jc.2010-1418. Epub Feb. 16, 2011.

Oresko et al., A wearable smartphone-based platform for real-time cardiovascular disease detection via electrocardiogram processing. IEEE Trans Inf Technol Biomed. May 2010;14(3):734-40. doi: 10.1109/TITB.2010.2047865. Epub Apr. 12, 2010.

Ozdalga et al., The smartphone in medicine: a review of current and potential use among physicians and students. J Med Internet Res. Sep. 27, 2012;14(5):e128. Review.

Publications Committee, Society for Maternal-Fetal Medicine et al., Evaluation and management of severe preeclampsia before 34 weeks' gestation. Am J Obstet Gynecol. Sep. 2011;205(3):191-8. doi: 10.1016/j.ajog.2011.07.017. Epub Jul. 20, 2011. Review.

Roberts et al., Pre-eclampsia: more than pregnancy-induced hypertension. Lancet. Jun. 5, 1993;341(8858):1447-51. Erratum in: Lancet Aug. 21, 1993;342(8869):504.

Ruano-Lopez et al., The SmartBioPhone, a point of care vision under development through two European projects: OPTOLABCARD and LABONFOIL. Lab Chip. Jun. 7, 2009;9(11):1495-9. doi: 10.1039/b902354m. Epub Mar. 10, 2009.

Rybarska et al., Evidence that supramolecular Congo red is the sole ligation form of this dye for L chain lambda derived amyloid proteins. Folia Histochem Cytobiol. 2001;39(4):307-14.

Styren et al., X-34, a fluorescent derivative of Congo Red: A novel histochemical stain for Alzheimer's disease pathology. J of Histochem and Cytochem. 2000 48(9):1223-32.

Talaga, Inhibitors of beta-amyloid aggregation: still an issue of structure and function? Drug Discovery Today: Therapeutic Strategies. Sep. 2004;1(1):7-12.

Tang et al., Decreased levels of folate receptor-β and reduced numbers of fetal macrophages (Hofbauer cells) in placentas from pregnancies with severe pre-eclampsia. Am J Reprod Immunol. Aug. 2013;70(2):104-15. doi: 10.111/aji.12112. Epub Mar. 11, 2013.

Thangaratinam et al., Estimation of proteinuria as a predictor of complications of preeclampsia: a systematic review. BMC Med. Mar. 24, 2009;7:10. doi: 10.1186/1741-7015-7-10. Review.

Vieira et al., Small molecule inhibitors of lysozyme amyloid aggregation. Cell Biochem Biophys. 2006;44(3):549-53.

Wallukat et al., Patients with preeclampsia develop agonistic autoantibodies against the angiotensin AT1 receptor. J Clin Invest. Apr. 1999;103(7):945-52.

Ward et al., A molecular variant of angiotensinogen associated with preeclampsia. Nat Genet. May 1993;4(1):59-61.

Wolf et al., Diagnostic inaccuracy of smartphone applications for melanoma detection. JAMA Dermatol. Apr. 2013;149(4):422-6. doi: 10.1001/jamadermatol.2013.2382.

Wu et al., Dual binding modes of Congro red to amyloid protofibril surface observed in molecular dynamics simulations. J Am Chem Soc. Feb. 7, 2007;129(5):1225-32.

Zhang et al., Maternal vasculopathy and histologic diagnosis of preeclampsia: poor correlation of histologic changes and clinical manifestation. Am J Obstet Gynecol. Apr. 2006;194(4):1050-6.

Calbiochem General Catalog (2002-2003), catalog #234610, p. 180.

Davis et al., Supramolecular assembly dynamics. Proc Natl Acad Sci U S A. Apr. 16, 2002;99(8):4793-6. Epub Mar. 5, 2002.

Lehn, Toward self-organization and complex matter. Science. Mar. 29, 2002;295(5564):2400-3.

Lehn, Supramolecular Chemistry-Scope and Perspectives. Molecules-Supermolecules-Molecular Devices. Nobel lecture, Dec. 8, 1987. 48 pages.

Paas Magical Color Cups (2005). 1 page.

(56) References Cited

OTHER PUBLICATIONS

Rybarska et al., In vivo accumulation of self-assembling dye Congo red in an area marked by specific immune complexes: possible relevance to chemotherapy. Folia Histochem Cytobiol. 2004;42(2):101-10.
Stopa et al., Effect of self association of bis-ANS and bis-azo dyes on protein binding. Biochimie. 1997;79(1):23-6.
U.S. Appl. No. 16/406,942, filed May 8, 2019, Buhimschi et al.
Hrncic et al., Antibody-mediated resolution of light chain-associated amyloid deposits. Am J Pathol. Oct. 2000;157(4):1239-46.
Kayed et al., Common structure of soluble amyloid oligomers implies common mechanism of pathogenesis. Science. Apr. 18, 2003;300(5618):486-9.
Kayed et al., Conformation-dependent anti-amyloid oligomer antibodies. Methods Enzymol. 2006;413:326-44.
Kayed et al., Fibril specific, conformation dependent antibodies recognize a generic epitope common to amyloid fibrils and fibrillar oligomers that is absent in prefibrillar oligomers. Mol Neurodegener. Sep. 26, 2007;2:18.
Levites et al., Anti-Abeta42- and anti-Abeta40-specific mAbs attenuate amyloid deposition in an Alzheimer disease mouse model. J Clin Invest. Jan. 2006;116(1):193-201. Epub Dec. 8, 2005.
O'Nuallain et al., Conformational Abs recognizing a generic amyloid fibril epitope. Proc Natl Acad Sci U S A. Feb. 5, 2002;99(3):1485-90. Epub Jan. 29, 2002.

1= α-hemolysin in PBS
2= α-hemolysin w/ deoxycholate
3= Aβ42 in NaOH

_US 11,125,758 B2_

METHODS AND KITS FOR DETECTING MISFOLDED PROTEINS

RELATED APPLICATIONS

This application is a continuation of U.S. application Ser. No. 14/849,670 filed Sep. 10, 2015, which is a continuation of U.S. application Ser. No. 13/126,757 filed Aug. 3, 2011, now U.S. Pat. No. 9,229,009, which is a national stage filing under 35 U.S.C. § 371 of international application number PCT/US2009/005957 filed Nov. 2, 2009, which was published under PCT Article 21(2) in English and claims the benefit under 35 U.S.C. § 119(e) of U.S. provisional application No. 61/197,914 filed on Oct. 31, 2008 and U.S. provisional application No. 61/206,534 filed Jan. 29, 2009, each of which is herein incorporated by reference in its entirety.

BACKGROUND OF THE INVENTION

Preeclampsia complicates 6-8% of pregnancies (Hauth, J. C. et al., Obstet Gynecol. 95(1):24-8, 2000) with an incidence in the US of 23.6 cases per 1000 deliveries in the US. (Samadi, A. R. et al., Obstet Gynecol. 87(4):557-63, 1996.) Preeclampsia has been determined to be responsible for 20% of pregnancy-related maternal deaths (MacKay, A. P. et al., Paediatr Perinat Epidemiol. 19(3):206-14, 2005), the leading reason for a medically indicated preterm delivery (MIPTD) (Fronterhouse, W. et al., J Matern Fetal Med. 10(3):162-5, 2001) and responsible for 10% of all premature births. (Fronterhouse, W. et al., J Matern Fetal Med. 10(3):162-5, 2001.) Preeclampsia (PE) is characterized by the onset of elevated blood pressure with proteinuria after 20 weeks of gestation. (ACOG Committee on Practice Bulletins. Obstet Gynecol. 99(1):159-67, 2002.) It is considered severe (sPE) if blood pressure and proteinuria are increased substantially or symptoms of end-organ damage, including fetal growth restriction, occur. The course of severe preeclampsia is associated with a progressive deterioration of maternal condition and iatrogenic delivery remains the only definitive treatment. Management from the part of the caring physician consists of balancing the risks of immediate delivery of an immature fetus against the risks to both mother and child of a complication of preeclampsia. For this, the current approach is close monitoring of maternal and fetal status with delivery remaining the ultimate treatment. (Zamorski, M. A. & Green, L. A. Am Fam Physician 64: 263-70, 216, 2001.)

Currently, there is no single test to predict or diagnose preeclampsia or to foretell the severity of the condition that will develop in a particular patient. Early symptoms include persistent headaches, blurred vision or sensitivity to light and abdominal pain. However, a diagnosis of preeclampsia is often not made until increased blood pressure and protein in the urine (proteinuria) are revealed, typically in routine physician tests following the 20$^{th}$ week of pregnancy (Roberts J M, Cooper D W. Pathogenesis and genetics of preeclampsia. Lancet. 2001; 357(9249):53-56). Severe effects of preeclampsia, including seizures, cerebral hemorrhage, disseminated intravascular coagulation and renal failure, may appear very shortly following such diagnosis. These methods are imprecise and provide little insight into the likelihood of the most severe symptoms developing. Moreover, the current diagnostics require physician oversight and invasive methodologies, further delaying and complicating early and immediate assessment. An early and accurate method for the detection and diagnosis of preeclampsia and associated proteinuric hypertensive disorders that does not require physician oversight is needed.

SUMMARY OF THE INVENTION

As described herein, Applicants have shown that preeclampsia (PB) is a pregnancy-specific condition characterized by protein misfolding (formation of abnormal or misfolded protein aggregates). In addition, they have shown that characteristic abnormal protein aggregates (also referred to as misfolded protein aggregates or intermediates), are present in the urine and accumulate in the placenta of pregnant women (patients) with preeclampsia and are congophilic. These abnormal protein aggregates are associated with the occurrence of preeclampsia and their presence in urine and/or placental tissue is indicative of preeclampsia. As described herein, the term "supramolecular aggregates of misfolded proteins" (and the shortened term "supramolecular aggregates") encompasses both soluble protein aggregates and insoluble protein aggregates. The presence of supramolecular aggregates of misfolded protein aggregates that are associated with preeclampsia, such as those described herein, can be used to determine the presence of preeclampsia in a pregnant woman, as well as the likelihood or risk that a pregnant woman will develop preeclampsia.

Recent advances in proteomics enabled biomarker discovery and a novel view of preeclampsia (PE) as a misfolding disorder. As described herein, Applicants have determined the presence, as well as the nature ad level, of protein misfolding in PE. They have shown that PE is characterized by increased excretion of misfolded proteins that can be detected using the affinity of misfolded protein aggregates for certain dyes, such as for example the self-assembling azo dye Congo Red (CR).

Protein conformational disorders, such as Alzheimer's, light chain amyloidosis and prion diseases, are propagated by amyloid fibril formation and aggregation due to defective folding of cellular proteins into aberrant 3D structures. Applicants observed that soluble pre-amyloid oligomers (intermediates in fibril assembly, also referred to as misfolded protein intermediates) have proteotoxic effects that lead to endothelial damage and oxidative stress, which are processes that play pathogenic roles in severe preeclampsia (sPE). Applicants have found that the detectable presence of soluble pre-amyloid oligomers is indicative and/or predictive of severe PE and pre-severe PE (pre-preeclampsia), a subclinical state that precedes onset of clinically manifest sPE.

Thus, Applicants worked to identify and characterize the nature of urinary soluble pre-amyloid oligomers in this pregnancy-specific condition. Theirs is the first observation that PE is a conformational disorder characterized by amyloid-like assembly of proteins.

Further work described herein, carried out using antibodies that recognize proteins and protein oligomers that have adopted a unique folding conformation, supports the observation that the misfolded protein intermediates have a propensity to assemble into pore-like structures (amyloid channels) that appear to play a role in clinical disease manifestations. The accumulation of abnormal and/or excessive misfolded protein aggregates in the urine and/or placenta of patients diagnosed with PE or destined to develop PE, indicates that these abnormal protein aggregates are a causative factor in the pathology of this disease. This novel finding provides the basis for new diagnostic and therapeutic strategies to treat (reduce, partially or totally, the onset or progression; reverse) preeclampsia. For example, blocking the formation of such structures with immunological or pharmacological strategies and reversing (disrupting) existing supramolecular aggregates provide new lines of therapeutic intervention for preeclampsia.

Characteristics of such abnormal protein aggregates (of the supramolecular amyloid-like assembly of proteins), in addition to their affinity for Congo Red, are also described herein. One component of supramolecular aggregates abnormal protein aggregates found in urine and placental tissue in preeclampsia is SerpinA1 (alpha-1 antitrypsin) and peptide fragments of SerpinA1. Thus, preeclampsia has a characteristic similar to that of other disorders, such as alpha-1 antitrypsin deficiency, in which accumulation of misfolded alpha-1 antitrypsin leads to damage of hepatocytes and cirrhosis of the liver (n. Engl. 1 ed. 346:45-53 (2002); J. Clin. Inv. 110: 1585-1590 (2002). In addition, ceruloplasmin, heavy-chain IgG and light-chain IgG, interferon-inducible protein 6-16 (IFI6-16, G1P3) and fragments of each were identified in congophilic proteinuria of PE as components of the misfolded protein aggregates. Isolated abnormal protein aggregates that are associated with preeclampsia and are present in urine and placental tissue are described herein and, in specific embodiments discussed further herein, such isolated abnormal protein aggregates comprise at least one (a, one or more) of SerpinA1, ceruloplasmin, heavy-chain IgG, light-chain IgG, interferon-inducible protein 6-16 and fragments of each.

One embodiment of the invention described herein is a noninvasive urine diagnostic and prognostic test or assay that is based on determining the presence and, optionally, the quantity of abnormal protein aggregates that are associated with preeclampsia, described further herein, that demonstrate Congo Red affinity (congophilia) and is a measure of global protein misfolding load in pregnancy. Assessment of global protein misfolding load by Congo Red Retention (CRR) is a simple diagnostic test for PE and for prediction of indicated delivery (IND), which is an important contributor to preterm birth. The diagnostic and prognostic assays are described herein, in some embodiments, with reference to assessing or analyzing a sample (e.g., urine or placental tissue) obtained from a pregnant woman for the presence of abnormal protein aggregates that are associated with preeclampsia and exhibit congophilia. However, it is understood that the diagnostic and prognostic assays can be carried out using a wide variety of agents that permit assessment or analysis of a sample to determine the presence (and, optionally, the quantity) of abnormal protein aggregates that are associated with preeclampsia, as described herein, and that congophilia is but one, descriptive property of the misfolded protein aggregates. Other properties are, for example, the composition and conformation of the abnormal protein aggregates, which, in turn, define other characteristics of the misfolded protein aggregates, such as their size, interactions with other dyes, and binding by antibodies that can be used in a diagnostic or prognostic method.

Described herein is a method of diagnosing or aiding in diagnosing preeclampsia in a pregnant woman by detecting a (one, one or more) supramolecular aggregates of misfolded proteins (abnormal protein aggregates, misfolded protein aggregates, misfolded protein intermediates, supramolecular amyloid-like assembly of proteins) that is associated with preeclampsia in urine or placental tissue of the pregnant woman. It should be appreciated that the diagnostic tests described herein can be carried out at any time during pregnancy. In certain embodiments, the diagnostic tests described herein can be carried in women planning to become pregnant.

Such supramolecular aggregates can be detected in urine, as well as in placental tissue, using a variety of techniques or methods known to those of skill in the art. An appropriate technique is one that permits detection of the abnormal protein aggregates in urine or placental tissue at the levels at which they occur in preeclampsia. Such techniques can make use of a dye, a small molecule, a fluorescent compound or other agent (such as an antibody, antibody fragment, antibody mimetic) that binds or otherwise interacts with abnormal protein aggregates and, as a result labels, flags or otherwise alters the aggregates so that they are detectable. One result, in this and in other embodiments described herein, is that the supramolecular aggregates/abnormal protein aggregates, as well as the urine or placental tissue sample, are different from the originally-obtained urine or placental tissue and its constituents (e.g, samples have been modified, such as by addition of reagents used in their analysis, change in temperature or dilution or concentration; abnormal protein aggregates are labeled, flagged or otherwise altered, e.g., so that they can be detected). It should be appreciated that if a dye is used, a dye useful for the detection of supramolecular aggregates described herein may have one or more of the following characteristics: a self-assembling dye, a non self-assembling dye, a heteroaromatic dye, an azo dye, a fibril-specific dye and/or another dye. Such dyes may include, but are not limited to Congo Red, curcumin analogs; X-34 (1,4-bis(3-carboxy-4-hydroxyphenylethenyl)-benzene); Thioflavin S; Thioflavin T; Nile Red; acridino orange; Amino-8-napthalene sulfonate (ANS); Bis-ANS; 4-(dicyanovinyl)-julolidine (DCVJ); AO1987 (oxazine dye); fluorescent styryl dyes; BF-168: (6-2-Fluoroethoxy)-2-[2-(4-methylaminophenil)ethenyl]benzoxazole; BSB: (trans,trans)-1-bromo-2,5-bis-(3-hydroxycarbonyl-4-hydroxy)styrylbenzene; quinilinehydrazone compounds (e.g., 4-methyl-7-methoxy-2-(4-quinolylmethylenehydrazino)quinoline); Chrysamine-G; rifampicin; melatonin; baicalein; soyllitol (e.g. Cocositol, Quercinitol, 1,3,5/2,4,6-Hexahydroxycyclohexane) and derivatives; imaging probes, such as [11C]-PIB:N-methyl [11C]2-(4'-methylaminophenyl-6-hydroxybenzathiazole); stilbenylbenzothiazole and stilbenylbenzothiazole derivatives.

Self-assembling dyes include for example, Congo Red, Evans Blue, bis-azo ANS and non self-assembling dyes include, for example, ANS and Trypan Blue.

As described herein, such abnormal protein aggregates exhibit affinity for the self-assembling azo dye Congo Red and, thus, their presence in urine or placental tissue can be determined (and, optionally, quantified) by detecting congophilia in mine or placental tissue obtained from a pregnant woman to be assessed (tested) for preeclampsia. Described herein is a method of diagnosing or aiding in diagnosing preeclampsia in a pregnant woman, in which detection of urine congophilia, such as by dot blot fixation and spectral shift assays, is indicative of a pregnant woman with preeclampsia (indicates that the pregnant woman has preeclampsia) or as likely to have preeclampsia (which can be confirmed, if needed, by further assessment, using known methods). As further described herein, although the abnormal protein is referred to as congophilic, this is a descriptive term and it is to be understood that the abnormal protein can be detected by a variety of other means, including other agents, such as other dyes (e.g., other self-assembling dyes), a Thioflavin (Thioflavin S, Thioflavin T) and antibodies (e.g., both polyclonal, such as A11 antibody, Officer antibody, OC antibody and monoclonal, such as M118, M204, M205, M89 (such as M89-17) and M09) or by visualizing the aggregates by e.g. polarizing light microscopy, fluorescence microscopy or electron microscopy.

The abnormal protein aggregate or fragment thereof detected through detection of congophilia can be the abnormal protein aggregate described herein, which comprises at least one (a, one or more) of SerpinA1, ceruloplasmin, heavy-chain IgG, light-chain IgG, and interferon-inducible protein 6-16, or a fragment of any of the foregoing.

It should be understood that in all embodiments described herein, a variety of antibodies (polyclonal or monoclonal) can be used. In specific embodiments, at least one (a, one or more) of the following antibodies or their equivalents (antibodies that recognize (bind) in substantially the same manner (e.g., to the same epitope or conformations can be used: A11 antibody, OC antibody, Officer antibody, M118 antibody, M204 antibody, M205 antibody, M89 antibody (e.g., 89-17) and M09 antibody.

In specific embodiments, the method of diagnosing or aiding in diagnosing preeclampsia in a pregnant woman comprises (a) obtaining a urine sample or placental tissue sample from the woman; (b) combining (contacting) the sample obtained in (a) with an agent (e.g., a dye, such as Congo Red, or an antibody) that binds or otherwise labels abnormal protein aggregate that is associated with PE or binds or otherwise labels a component of such abnormal protein aggregate, under conditions under which binding to or other interaction with abnormal protein aggregate occurs, thereby producing detectable (labeled) abnormal protein aggregates or components thereof (e.g., detectable serpina-2 or other component) and (b) determining if binding or other interaction occurred in (a), such as by determining whether detectable abnormal protein aggregates or components thereof are in the sample, wherein binding is indicative of preeclampsia in the woman and woman is diagnosed as having or likely to have preeclampsia. Her status (having preeclampsia or not having preeclampsia) can be further assessed, using known methods, such as methods described herein, in order to confirm the determination resulting from the present method. The agent that binds or otherwise flags or labels abnormal protein can be any of many types available, such as a dye (e.g, Congo Red, Thioflavin S, Thioflavin T, Evans Blue, Trypan blue, ANS, bis-azo ANS), a radioactive tracer (e.g. (11)C Pittsburgh compound B (PIB)) or an antibody against (that binds) abnormal protein aggregates, such as antibodies that bind a characteristic region or feature of the conformation or one or more of the components of the abnormal protein aggregates, such as one or more of SerpinA1, ceruloplasmin, heavy-chain IgG, light-chain IgG, interferon-inducible protein 6-16 and fragments of each.

In a specific embodiment, the method of diagnosing or aiding in diagnosing preeclampsia in a pregnant woman comprises: (a) obtaining a urine sample or placental tissue sample from the pregnant woman; (b) combining the sample obtained in (a) with a dye that stains at least one protein or protein fragment present in the abnormal protein aggregates (e.g., Congo Red), under conditions under which the dye stains protein in the sample, thereby producing a urine sample or a placental tissue sample that further comprises the dye and (c) analyzing the urine sample or placental tissue sample produced in (b) for the presence of (determining if the sample contains) supramolecular aggregates, (abnormal protein aggregates) associated with preeclampsia stained with the dye, wherein if the sample contains supramolecular aggregates associated with preeclampsia stained with the dye, it is indicative of preeclampsia in the woman mad the woman is diagnosed as having or likely to have preeclampsia. If the sample contains such stained misfolded protein aggregates, she is more likely to have preeclampsia than if the sample does not contain abnormal protein aggregates associated with preeclampsia stained with the dye. The presence of abnormal protein aggregates associated with preeclampsia stained with the dye indicates that the woman has preeclampsia or is likely to have preeclampsia. Her status (having preeclampsia or not having preeclampsia (can be further assessed, using known methods, such as methods described herein, in order to confirm the determination resulting from the present method. The abnormal protein aggregate detected can be the abnormal protein aggregate described herein, which comprises at least one (one or more) of SerpinA1, ceruloplasmin, heavy-chain IgG, light-chain IgG, interferon inducible protein 6-16 or a fragment of any of the foregoing. Detection of stained abnormal protein aggregates can be carried out using known methods, such as dot blot analysis or simple visualization of an area of a stained surface (e.g., on a surface such as filter paper) that comprises the urine or placental tissue sample combined with the dye (e.g., urine combined with Congo Red).

A pregnant woman determined, using any of the embodiments described herein, as having, likely to have or to be at risk of developing preeclampsia can be further assessed for this condition or the presence or risk can be confirmed by carrying out an additional assessment, such as one or more of those described herein or known to one of skill in the art (e.g., blood pressure measurement, assessment of edema, abdominal pain, occurrence of headaches, vision problems).

Detection of urinary congophilic abnormal protein aggregates, as described herein, is not only diagnostic of existing preeclampsia, but also predictive of the future development of preeclampsia in a pregnant woman, which can also be seen as predictive of the increased risk that a pregnant woman will develop preeclampsia. In one embodiment, the method of predicting or aiding in predicting the likelihood that a pregnant woman will have (will develop) preeclampsia comprises obtaining a urine or placental tissue sample from the pregnant woman and analyzing the urine or placental tissue sample for the presence of (determining if the sample contains) abnormal protein aggregates associated with preeclampsia, wherein if the sample contains abnormal protein aggregates associated with preeclampsia, the woman is more likely to develop (has an increased likelihood of developing) preeclampsia than if the sample does not contain abnormal protein aggregates associated with preeclampsia. It should be appreciated that the methods for assessing the occurrence and/or risk of PE described herein include methods that detect the presence or absence of abnormal protein aggregates associated with preeclampsia (e.g. for rapid qualitative assessment) and methods that quantify the amount of and/or the precise nature of (e.g. identification of proteins in the aggregate, identification of the conformation of the aggregate, etc.) the supramolecular aggregates detected in the sample.

The abnormal protein aggregate detected can be a (one, one or more) supramolecular aggregate described herein, which comprises at least one (a, one or more) of SerpinA1, ceruloplasmin, heavy-chain IgG, light-chain IgG, interferon inducible protein 6-16 or a fragment of any of the foregoing. The method of predicting whether a pregnant woman will develop preeclampsia can be carried out, for example, by (a) obtaining a urine sample or a placental tissue sample from the pregnant woman; (b) combining the urine sample or placental tissue sample with an agent that binds or otherwise interacts with misfolded protein aggregates associated with preeclampsia, under conditions under which the agent binds or otherwise interacts with such misfolded protein aggregates or a component thereof thereby producing detectable (labeled) protein aggregates or components thereof (e.g., detectable SerpinA1 or other component); and (c) determining if binding or other interaction occurred in (b), such as by determining whether detectable misfolded protein aggregates or components are present in the sample, wherein if detectable misfolded protein aggregates are present, the pregnant woman is more likely to develop (has an increased likelihood of developing) preeclampsia than if detectable protein aggregates are not present. The agent that binds or otherwise flags or labels abnormal protein can be any of many types available, such as a dye (e.g. Congo Red, Thioflavin S, Thioflavin T, Evans Blue, Trypan blue, ANS, bis-azo ANS), a radioactive tracer (e.g. (11)C Pittsburgh compound B (PIB)) or an antibody against (that binds) abnormal protein aggregates, such as antibodies that bind a characteristic region or feature of the conformation or one or more of the components of the aggregates, such as one or more of SerpinA1, ceruloplasmin, heavy-chain IgG, light-chain IgG, interferon-inducible protein 6-16 and fragments of one or more of the foregoing.

In a specific embodiment, the method of predicting or aiding in predicting the likelihood that a pregnant woman will have (will develop) preeclampsia comprises: (a) obtaining a urine sample or a placental tissue sample from the pregnant woman; (b) combining the sample with a dye that stains at least one protein or protein fragment present in supramolecular aggregates associated with preeclampsia (e.g., Congo Red), under conditions under which the dye stains proteins in the sample, thereby producing a sample that further comprises the dye; and (c) analyzing the urine sample or placental tissue sample produced in (b) for the presence of (determining if the sample contains) supramolecular aggregates associated with preeclampsia stained with the dye, wherein if the sample contains supramolecular aggregates associated with preeclampsia stained with the dye, the woman is more likely to develop (has an increased likelihood of developing) preeclampsia than if the sample does not contain supramolecular aggregates associated with preeclampsia stained with the dye. Detection of stained aggregates can be carried out using known methods, such as dot blot analysis or simple visualization of an area of a stained surface (e.g., on a surface, such as filter paper) that comprises the urine or placental tissue sample combined with the dye (e.g., urine combined with Congo Red).

Similarly, the risk that a pregnant woman will develop preeclampsia can be assessed using the method described herein. In one embodiment, the method of determining the risk that a pregnant woman will have (will develop) preeclampsia comprises obtaining a urine or placental tissue sample from the pregnant woman and analyzing the urine or placental tissue sample for the presence of (determining if the sample contains) misfolded protein aggregates associated with preeclampsia, wherein if the sample contains misfolded protein aggregates associated with preeclampsia, the woman is at greater risk of developing preeclampsia than if the sample does not contain misfolded protein aggregates associated with preeclampsia. In a specific embodiment, the method of assessing or determining the risk that a pregnant woman will develop preeclampsia comprises (a) obtaining a urine sample or a placental tissue sample from a pregnant woman; (b) combining the urine sample or placental tissue sample with an agent that binds or otherwise interacts with misfolded protein aggregates associated with preeclampsia, under conditions under which the agent binds or otherwise interacts with such misfolded protein aggregates, thereby producing detectable (labeled) protein aggregates or components thereof (e.g., detectable serpina-2 or other component) and (c) determining if binding or other interaction occurred in (b), such as by determining whether detectable misfolded protein aggregates or components are present in the sample, wherein if detectable misfolded protein aggregates are present, the pregnant woman is at greater risk of developing preeclampsia than if detectable protein aggregates are not present. The agent that binds or otherwise flags or labels abnormal protein can be say of many types available, such as a dye (e.g. Congo Red, Thioflavin S, Thioflavin T, Evans Blue, Trypan blue, ANS, bis-azo ANS), a radioactive tracer (e.g. (11)C Pittsburgh compound B (PIB)) or a antibody against (that binds) abnormal protein aggregates, such as antibodies that bind a characteristic region or feature of the conformation or one or more of the components of the aggregates, such as one or more of SerpinA1, ceruloplasmin, heavy-chain IgG, light-chain IgG, interferon-inducible protein 6-16 and fragments of each of the foregoing.

In a specific embodiment, the method of assessing or estimating the risk that a pregnant woman will have (will develop) preeclampsia comprises (a) obtaining a urine sample or a placental tissue sample from the pregnant woman; (b) combining the sample with a dye (e.g., Congo Red) that stains at least one protein or protein fragment present in misfolded protein aggregates associated with preeclampsia, under conditions under which the dye stains proteins in the sample, thereby producing a sample that further comprises the dye; and (c) analyzing the urine or placental tissue sample produced in (b) for the presence of (determining if the sample contains) misfolded protein aggregate associated with preeclampsia stained with the dye, wherein if the sample contains misfolded protein aggregates associated with preeclampsia stained with the dye, the woman is at greater risk of developing (has an increased risk of developing) preeclampsia than if the sample does not contain misfolded protein aggregates associated with preeclampsia stained with the dye. Detection of stained aggregates can be carried out using known methods, such as dot blot analysis or simple visualization of an area of a stained surface (e.g., on a surface, such as filter paper) that comprises the urine or placental tissue sample combined with the dye (e.g., urine combined with Congo Red).

Placental tissue samples stained with Congo Red also display characteristic features of such protein aggregates and detecting staining, such as Congo Red staining. Other labeling of supramolecular aggregates in the placenta can also be used in diagnosing or aiding in diagnosing preeclampsia in a pregnant woman; predicting or aiding in predicting the likelihood that a pregnant woman will have (will develop) preeclampsia; and assessing or estimating the risk that a pregnant woman will have (will develop) preeclampsia.

In another embodiment described herein, the method is a method of diagnosing or aiding in diagnosing preeclampsia in a pregnant woman, in which detection of (determination of the presence of) supramolecular aggregates that are associated with preeclampsia in urine or placental tissue obtained from the pregnant woman is carried out by using antibodies that recognize (bind) proteins and protein oligomers that have adopted a unique folding conformation associated with preeclampsia, as described herein, or antibodies that recognize (bind) supramolecular aggregates ad/or a protein or peptide constituent of such aggregates that are associated with preeclampsia (as a component of/in the context of such an aggregate). The presence of such supramolecular aggregates is indicative of (is an indication that the pregnant woman has) preeclampsia.

Also described herein is an ex vivo method for diagnosing preeclampsia or of predicting the future development of preeclampsia in a subject (a pregnant woman), comprising the step of detecting abnormal/misfolded protein aggregates (supramolecular aggregates) in a sample of urine or placenta from said subject. In one embodiment, the supramolecular aggregates (abnormal/misfolded protein aggregates) are detected in a sample of urine. In a further embodiment, the abnormal/misfolded protein aggregates are detected in a sample of placenta. In any of the preceding embodiments, the abnormal protein aggregates are detected by Congo Red staining, such as by dot blot fixation and/or spectral shift assays, or by Thioflavin S staining. In my of the embodiments, the abnormal/misfolded protein aggregates can comprise SerpinA1 (alpha-1 antitrypsin) and/or peptide fragments thereof and/or fragments of ceruloplasmin and/or heavy-chain IgG and/or light-chain IgG.

Also described herein is a protein aggregation inhibitor for use in a method of treating and/or preventing preeclampsia in a pregnant woman. Protein aggregation inhibitors for use in a method of treating and/or preventing preeclampsia in a pregnant woman include 1) protein aggregation inhibitors that inhibit the de novo formation of supramolecular aggregates; 2) protein inhibitors that reverse the formation of pro-existing supramolecular aggregates; 3) protein inhibitors that inhibit the de novo formation of supramolecular protein aggregates and reverse or disrupt pre-existing supramolecular protein aggregates; 4) protein aggregation inhibitors that stabilize the native conformation of the protein, thereby decreasing the rate of abnormal folding and consequent aggregation; 5) protein aggregation inhibitors of 1) to 4) that inhibit the aggregation of SerpinA1 (alpha-1 antitrypsin) and/or peptide fragments thereof; a protein aggregation inhibitor of any one of 1) to 4), which inhibits the aggregation of SerpinA1 (alpha-1 antitrypsin) and/or peptide fragments thereof and is selected from: (a) trimethylamine N-oxide; (b) trimethylamine N-oxide-related compounds; (c) the FLEAIG peptide; and (d) peptides and derivatives related to the FLEAIG peptide; 6) a peptide inhibitor of any one of 1) to 5), which is selected from: (a) trimethylamine N-oxide; (b) trimethylamine N-oxide-related compounds; (c) the FLEAIG peptide; and (d) peptides and derivatives related to the FLEAIG peptide; 7) a peptide inhibitor of any one of 1) to 5), which is an anti-beta amyloid agent; 8) a peptide inhibitor of 7) wherein the anti-beta amyloid agent is selected from p-Aminophenol, 2-Amino-4-Chlorophenol pentapeptide iAβ5 (LPFFD) (Ax-onyx Inc.); Aβ aggregation inhibitor PPI-1019 (Praecis); the glycosaminoglycan (GAG) mimetic NC-531 (Neurochem); the antibiotic Clioquinol (Prana Biotechnology Ltd.), the small molecule cyclodextrin, the natural product from the *Ginkgo biloba* extract EGb 761 (Dr. Willman Schwabe GmbH & Co); polyphenols; SP-233, a 22R-hydroxycholesterol derivative (Samaritan Pharmaceuticals), Apomorphine, and Aβ immunization (Elan Pharmaceutical Inc., Acumen's ADDL technology). See also, Drug Discovery Today: Therapeutic Strategies 2004 Elsevier Ltd 1(1):7-12.

Also described herein is a method for developing and testing therapies (e.g., drugs) that can be used to treat preeclampsia. For example, drugs, including those known or subsequently found to reduce severity of other misfolding disorders, can be tested. For example, drugs, that have been assessed for their effectiveness in treating, for example, Alzheimer's disease, light chain amyloidosis and prion diseases, can be assessed for their effectiveness in treating preeclampsia, including preventing its onset, reducing the extent to which preeclampsia occurs or reversing existing preeclampsia (e.g., by disrupting, degrading or otherwise interrupting misfolded protein aggregates associated with preeclampsia, reducing the burden of pre-existing misfolded protein aggregates). Such agents, as well as agents that have not yet been assessed for their usefulness in treating diseases of abnormal protein aggregations, can be tested in order to identify those of use in treating preeclampsia.

Methods of treating preeclampsia in a pregnant woman are also described herein. In a method of treating preeclampsia, a pregnant woman is given a therapeutically effective amount of for example, a drug that that inhibits (partially or completely) de novo formation of protein aggregates; a drug that reverses (partially or completely) the burden or existence of preexisting protein aggregates; a drug that stabilizes the native conformation of these proteins, thereby decreasing the rate of abnormal folding and consequent aggregation; or a combination of drugs (more than one drug of the same type or mode of action, such as two drugs that inhibit do novo formation of protein aggregates; more than one drug which are not of the same type or mode of action, such as a drug that inhibits do novo formation of protein aggregates and a drug that reduces the burden of preexisting protein aggregates).

As further described herein, Applicants claim the following:

1. A method of diagnosing or aiding in the diagnosis of preeclampsia in a pregnant woman, comprising:
   (a) obtaining a sample from the woman; and
   (b) detecting the presence in the ample of a supramolecular aggregate of misfolded proteins that is associated with (is a causative factor in the pathology of) preeclampsia, wherein if the supramolecular aggregate is present in the sample, the woman has preeclampsia or is more likely to have preeclampsia than if the supramolecular aggregate is not present in the sample.

2. A method of diagnosing or aiding in diagnosing preeclampsia in a pregnant woman, comprising:
   (a) obtaining a sample from the woman;
   (b) combining the sample with a reagent that labels a supramolecular aggregate of misfolded proteins that (i) comprises serpina-1 (alpha-1 antitrypsin) or a fragment of serpina-1 and (ii) is associated with (a causative factor in the pathology of) preeclampsia, under conditions appropriate for labeling of the supramolecular aggregate to occur, and
   (c) determining if the supramolecular aggregate is present in the sample,
   wherein if the protein aggregate is present, the woman has preeclampsia or is more likely to have preeclampsia than if the supramolecular aggregate is not present in the sample.

3. The method of claim 1, wherein the supramolecular aggregate comprises serpina-1 (alpha-1 antitrypsin) or a fragment of serpina-1.

4. The method of claim 2 or claim 3, wherein the supramolecular aggregate further comprises at least one of ceruloplasmin, heavy-chain IgG, light-chain IgG and interferon inducible protein 6-16 (IFI6).

5. The method of any one of claims 1, 3 or 4, wherein the presence of the supramolecular aggregate is detected by combining the sample with a reagent that detectably labels the supramolecular aggregate.

6. The method of any one of the claims 1 to 5, wherein the sample is a urine sample or a placental tissue sample.

7. The method of any one of claims 1 to 6, wherein the reagent is a dye, an antibody or a fluorescent label.

8. The method of claim 7, wherein the dye is a heteroaromatic dye.

9. The method of claim 8, wherein the dye is Congo red or a Thioflavin.

10. The method of any one of claims 7 to 9, wherein the dye stains supramolecular aggregates and staining of supramolecular aggregates is detected by dot blot fixation and/or spectral shift assay.

11. A diagnostic assay for preeclampsia in a pregnant woman, wherein the assay is a determination of the presence of congophilic proteinuria in the woman and a congophilic protein aggregate that comprises serpina-1 (alpha-1 antitrypsin) or a fragment of serpina-1 is detected in a urine sample obtained from the pregnant woman.

12. The method of claim 7, wherein the antibody is a conformation-dependent, amino acid sequence independent antibody.

13. The method of claim 12, wherein the conformation-dependent antibody recognizes one or more epitopes on one or more supramolecular aggregates of misfolded protein selected from the group consisting of prefibrillar oligomer, fibrillar oligomer, protofibril and amyloid fibril.

14. The method of claim 13, wherein the conformation-dependent antibody recognizes one or more epitopes on a fibrillar oligomer and/or amyloid fibril.

15. The method of claim 13, wherein the conformation-dependent antibody binds one or more epitopes on a (ring-shaped) protofibril.

16. The method of claim 13, wherein the conformation-dependent antibody binds one or more epitopes on a prefibrillar oligomer.

17. The method of claim 14, wherein the conformation specific antibody is OC antibody.

18. The method of claim 15, wherein the conformation specific antibody is Officer antibody.

19. The method of claim 16, wherein the conformation-specific antibody is A11 antibody.

20. The method of claim 15 or 18, wherein if the protofibril-specific antibody is immunoreactive with the sample, the woman has developed or is likely to develop hemolysis.

21. A method of diagnosing or aiding in diagnosing preeclampsia in a pregnant woman, comprising
(a) obtaining a urine sample or a placental tissue sample from the woman;
(b) contacting the sample with a conformation-dependent antibody that binds a supramolecular aggregate of misfolded protein associated with preeclampsia, wherein if the antibody binds a component of the sample, the woman has preeclampsia or is more likely to have preeclampsia than if the antibody does not bind a component of the sample.

22. The method of claim 21, wherein the component of the sample is supramolecular aggregate that is a prefibrillar oligomer, a fibrillar oligomer, a protofibril or an amyloid fibril, 23. The method of claim 22, wherein the conformation-dependent antibody recognizes one or more epitopes on a fibrillar oligomer and/or amyloid fibril.

24. The method of claim 22, wherein the conformation-dependent antibody recognizes one or more epitopes on a (ringshaped) protofibril.

25. The method of claim 22, wherein the conformation-dependent antibody recognizes one or more epitopes on a prefibrillar oligomer.

26. The method of claim 23, wherein the conformation specific antibody is OC antibody.

27. The method of claim 24, wherein the conformation specific antibody is Officer antibody.

28. The method of claim 25, wherein the conformation-specific antibody is A11 antibody.

29. The method of claim 24 or 27, wherein if the protofibril-specific antibody is immunoreactive with the sample, the woman has developed or is likely to develop hemolysis.

30. A method of determining whether a pregnant woman is at risk of developing preeclampsia, comprising:
(a) obtaining a sample from the woman;
(b) detecting the presence in the sample of a supramolecular aggregate of misfolded proteins that is associated with (is a causative factor in the pathology of) preeclampsia, wherein if the supramolecular aggregate is present in the sample, the woman is at greater risk of developing preeclampsia than if the protein aggregate is not present in the sample.

31. A method of determining whether a pregnant woman is at risk of developing preeclampsia, comprising:
(a) obtaining a sample from the woman;
(b) combining the sample with a reagent that labels a supramolecular aggregate of misfolded proteins that (i) comprises serpina-1 (alpha-1 antitrypsin) or a fragment of serpina-1 and (it) is associated with (is a causative factor in the pathology of) preeclampsia, under conditions appropriate for labeling of the supramolecular aggregate to occur, and
(c) determining if the supramolecular aggregate is present in the sample,
wherein if the supramolecular aggregate is present, the woman is at greater risk of developing preeclampsia than if the protein aggregate is not present in the sample.

32. The method of claim 30, wherein the supramolecular aggregate comprises serpina-1 (alpha-1 antitrypsin) or a fragment of serpina-1.

33. The method of claim 31 or 32, wherein the supramolecular aggregate further comprises at least one of ceruloplasmin, heavy-chain IgG, light-chain IgG and interferon inducible protein 6-16 (IFI6).

34. The method of any one of claims 30, 32 or 33, wherein the presence of the supramolecular aggregate is detected by combining the sample with a reagent that detectably labels the supramolecular aggregate.

35. The method of any one of claims 30 to 34, wherein the sample is a urine sample or a placental tissue sample.

36. The method of claim 34 or 35, wherein the reagent is a dye, an antibody, or a fluorescent label.

37. The method of claim 36, wherein the dye is Congo red or a Thioflavin.

38. The method of any one of claims 35 to 37, wherein Congo red dye stains supramolecular aggregates and staining of supramolecular aggregates is detected by dot blot fixation and/or spectral shift assay.

39. A method of reducing the extent to which preeclampsia occurs in a pregnant woman, comprising administering to the woman a therapeutically effective amount of an inhibitor of the occurrence [formation] in the woman of protein aggregates that comprise serpina-1 (alpha-1 antitrypsin) or a serpina-1 fragment and are associated with (are a causative factor of) preeclampsia, wherein a therapeutically effective amount is an amount sufficient to inhibit (partially or completely) development of supramolecular aggregates, disrupt (partially or completely) existing supramolecular aggregates or both.

40. The method of claim 39, wherein the inhibitor stabilizes the native conformation of at least one component of supramolecular aggregates and decreases the extent to which abnormal folding occurs, whereby formation of supramolecular aggregates in the woman occurs to a lesser extent than would occur in the absence of the inhibitor.

41. The method of 39 or 40, wherein the inhibitor is an antibody or antibody fragment that binds a component of the protein aggregate, a trimethylamine N-oxide, an anti-beta amyloid agent (e.g., p-aminophenol, 2-amino-4-chlorophenol, a derivative thereof), a small molecule inhibitor of fibril formation, protofibril formation or oligomer formation; or a peptide inhibitor of fibril formation, protofibril formation or oligomer formation.

42. An ex vivo method for diagnosing preeclampsia or of predicting the future development of preeclampsia in a subject comprising the step of detecting abnormal protein aggregates (supramolecular aggregates of misfolded proteins) in a sample of urine or placenta from said subject.

43. The method of claim 1, wherein the abnormal protein aggregates are detected in a sample of urine.

44. The method of claim 42, wherein the abnormal protein aggregates are detected in a sample of placenta.

45. The method of any one of claims 42 to 44, wherein said abnormal protein aggregates are detected by Congo Red staining.

46. The method of claim 45, wherein the Congo Red staining comprises dot blot fixation and spectral shift assays.

47. The method of any one of claims 42 to 44, wherein said abnormal protein aggregates are detected by Thioflavin S or Thioflavin A staining.

48. The method of any one of claims 42 to 47, wherein the abnormal protein aggregates comprise serpina-1 (alpha-1 antitrypsin) and/or peptide fragments thereof.

49. The method of any one of claims 42 to 48, wherein the abnormal protein aggregates comprise fragments of ceruloplasmin and heavy- and light-chain IgG.

50. A protein aggregation inhibitor for use in a method of treating and/or preventing preeclampsia.

51. The inhibitor of claim 50, which inhibits the de novo formation of protein aggregates.

52. The inhibitor of claim 50 or claim 51, which reverses or disrupts the formation of pre-existing protein aggregates.

53. The inhibitor of claim 50, which stabilizes the native conformation of the protein, thereby decreasing the rate of abnormal folding and consequent aggregation.

54. The inhibitor of any one of claims 50 to 53, which inhibits the aggregation of serpina-1 (alpha-1 antitrypsin) and/or peptide fragments thereof, which is selected from: (a) trimethylamine N-oxide (b) trimethylamine N-oxide-related compounds; (c) the FLEAIG peptide; and (d) peptides and derivatives related to the FLEAIG peptide.

55. The inhibitor of any one of claims 50 to 54, which is selected from: (a) trimethylamine N-oxide; (b) trimethylamine N-oxide-related compounds; (c) the FLEAIG peptide; and (d) peptides and derivatives related to the FLEAIG peptide.

56. The inhibitor of any one of claims 50 to 54, which is an anti-beta amyloid agent.

57. The inhibitor of claim 56, wherein the anti-betas amyloid agent is selected from p-Aminophenol, and 2-Amino-4-Chlorophenol.

58. The method of claim 7 wherein the antibody is at least one (one or more) of the following. A11 antibody, OC antibody, Officer antibody, M118 antibody, M204 antibody, M205 antibody, M89 antibody (e.g., 89-17) and M09 antibody.

DETAILED DESCRIPTION OF THE INVENTION

Figure 1:
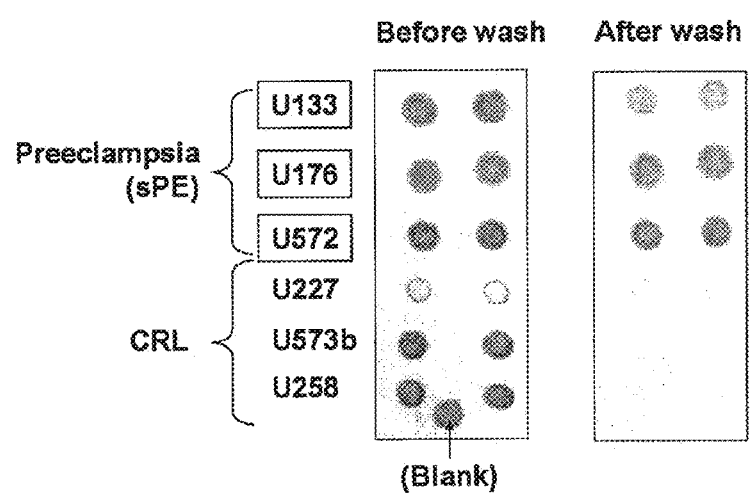
FIG. 1 shows a photograph of a nitrocellulose membrane before (left) and after wash (right) following Congo Red Dot Test of urine samples (5 µL/spot were applied to nitrocellulose).

Preeclampsia develops in the second half of pregnancy and is associated with significant maternal and fetal morbidity and mortality. Presently, there is no effective screening test to diagnose or assess the risk of developing this disease and associated hypertensive disorders. As a result, pregnant women cannot receive effective monitoring or treatment until after complications associated with the disorders, including increased blood pressure and proteinuria, have developed. Additionally, pregnant women with little to no risk of developing such disorders must undergo unnecessary testing for symptoms throughout their pregnancy because there is no effective means by which caregivers may exclude them from risk in the early stages of pregnancy. Further, current test require the oversight of a physician.

Described herein are methods and compositions related to the detection and/or monitoring of PE-associated congophilia and detection of specific conformations of aggregates of misfolded protein associated with or causative of PE, which are useful in diagnosis and treatment of PE. Also described herein are additional biomarkers that can be used independently in diagnosis and treatment of PE and, in conjunction with methods and compositions described herein, as biomarkers that can be used to confirm or further assess the status of a pregnant woman as to PE. For example, a woman who has been assessed, using the presently-described methods that rely on detection of misfolded protein aggregate, as having preeclampsia or being at increased risk of having preeclampsia, can be further assessed by relying on methods in which additional biomarkers or indicators that are associated with (are indicators of) preeclampsia are assessed. This can include, for example, detecting the presence or absence of certain additional biomarkers that are associated with (indicators of) preeclampsia (e.g. SerpinA1 and albumin) in a urine sample obtained from the pregnant woman and/or determining the ratio of biomarkers that are associated with (are indicators of) preeclampsia (e.g, sFlt-1 and PlGF) in a wine ample. Assessment of these biomarkers can confirm or aid in confirming (or negate or aid in negating) the assessment, resulting from application of the presently-described methods, that a pregnant woman has preeclampsia or is at risk of having preeclampsia. Methods by which such assessments can be carried out are described herein and in the referenced patent documents (e.g., U.S. application Ser. No. 12/084,004; PCT/US2006/042585 and U.S. Publ. No: US-2006-0183175; PCT/US2005/047010, incorporated herein by reference in their entirety).

The methods disclosed are useful to diagnose or aid in diagnosis of pregnant women as having or as being at increased risk for developing any of the following hypertensive disorder: preeclampsia, eclampsia, mild preeclampsia, chronic hypertension, EPH gestosis, gestational hypertension, superimposed preeclampsia (including preeclampsia superimposed an chronic hypertension, chronic nephropathy or lupus), HELLP syndrome (hemolysis, elevated liver enzymes, low platelet count) and nephropathy.

The methods described herein may also be used to assess the risk of a pregnant woman developing a specific complication of hypertensive disorders, including preeclampsia. Such complications may include delivery by cesarean section, increased serum uric acid, increased systolic and diastolic blood pressures, dipstick proteinuria, gravidity, fetal weight at delivery, placental abruption, IUGR, hemolysis, thrombocytopenia, elevated liver enzymes and HELLP syndrome (hemolysis, elevated liver enzymes, low platelet count).

1. Congo Red Test/Congophilia for Diagnosis of PE

Protein instability, misfolding and aggregation into supramolecular structures with affinity for the self-assembling dye Congo red (congophilia) are features common to a growing number progressive human conditions, such as Alzheimer's, Parkinson's and prion diseases. Affinity for the azo dye Congo Red (CR) is used to detect aberrant amyloidal aggregates in such diseases associated with protein misfolding. Applicants have made the novel and unexpected observation that preeclampsia (PE) is a pregnancy-specific disease associated with protein misfolding and protein aggregation. Applicants have shown that PE is characterized by supramolecular amyloid-like assembly of proteins and congophilic proteinuria, indicating an increased excretion of misfolded proteins. Applicants reasoned that congophilia of PE-associated proteins in the urine provides a diagnostic and/or prognostic test for PE as a measure of global protein misfolding load in pregnancy.

Misfolded proteins associated with PE can be found in "supramolecular aggregate of misfolded proteins." As used herein, the term "supramolecular aggregate of misfolded proteins" (herein also referred to as "supramolecular aggregate," "abnormal protein aggregate," "supramolecular amyloid assembly" and "congophillic protein aggregate") refers to soluble protein aggregates and insoluble protein aggregates. These include: (1) pre-fibrillar oligomers (also referred to as "pre-amyloid oligomers" and "non-fibrillar misfolded protein aggregates") which are soluble and have adopted "amyloid-like" properties; (2) protofibrils; (3) fibrillar oligomers, which are soluble; and (4) amyloid fibrils, which are insoluble.

Samples, such as e.g., urine samples, obtained from PE patients, patients suspected of having PB or patients at risk of developing PE, may contain relatively few or no insoluble amyloid fibrils, but may contain any one of, or a mixture of soluble supramolecular aggregates, such as pre-fibrillar oligomers, fibrillar oligomers, and/or protofibrils.

In some embodiments, methods of diagnosing PB are provided that comprise detecting supramolecular aggregates in a sample. Supramolecular aggregates may be detected using, for example, a heteroaromatic and/or fibril-specific dye. In some embodiments, the presence of supramolecular aggregates in a sample, e.g., urine sample, may be detected using the capacity of these supramolecular aggregates to increase/enhance fluorescence of (or causing a spectral shift in) heteroaromatic dyes such as thioflavins (e.g. thioflavin T, ThT or thioflavin S, ThS) and Congo red (CR) compared with native protein. In some embodiments, methods of diagnosing PE are provided that comprise detecting soluble supramolecular aggregates, such as pre-fibrillar oligomers in a sample using a heteroaromatic and/or fibril-specific dye. Without wanting to be bound by any particular theory, it is thought that the addition of the heteroaromatic and/or fibril-specific dye to soluble supramolecular aggregates promotes the formation and precipitation of insoluble supramolecular aggregates from soluble supramolecular aggregates, such as pre-fibrillar aggregates and/or fibrillar aggregates, allowing easy detection of these aggregates.

Provided herein are methods for diagnosis or aiding in the diagnosis of preeclampsia. In certain embodiments, detection of urine congophilia (e.g., by dot blot fixation and/or spectral shift assays) is indicative of a pregnant woman with preeclampsia. In certain embodiments, the presence of urinary congophilic protein aggregates, detected as described, is not only diagnostic of an existing preeclampsia, but also predictive of the future development of preeclampsia. In certain embodiments, the presence of congophilic protein aggregates in placental tissue samples stained with Congo Red is used for the diagnosis of preeclampsia. It should be appreciated that the presence of protein aggregates can be detected through the use of a variety of other agents and methodologies. Such modifications are well within the capabilities of one of ordinary skill and do not involve undue experimentation. Such modifications to the methods described herein are meant to be part of the invention and are included herein.

In addition to dyes such as Congo Red and thioflavins other agents (including derivatives of Congo Rod and thioflavins) may also be used for detection of supramolecular aggregates described herein. These detection agents include, but are not limited to, curcumin analogs (e.g. J. Am. Chem Soc. 131: 15257 (2009)); X-34 (1,4-bis(3-carboxy-4-hydroxyphenylethenyl)-benzene), a highly fluorescent congo red (e.g. Ikonomovic et al. Methods in Enzymology 412 (2006), "Amyloid, Prions and other protein aggregates", Part B pp: 123-144) and J. Histochem and Cytochem 48: 1223 (2000); Thioflavin S; Thioflavin T; Nile Red; acridine orange; Amino-8-napthalene sulfonate (ANS) and Bis-ANS; 4-(dicyanovinyl)-julolidine (DCVJ) (e.g. Biophysical Journal 94 (12): 4867-4879, 2008); AO1987 (oxazine dye) (e.g. Nature Biotechnology 23(5) 577 (2005); fluorescent styryl dyes (e.g. Angewandte Chemie, International Edition 43 (46) 6331-6335 (2004); BF-168: (6-2-Fluoroethoxy)-2-[2-(4-methylaminophenil)ethenyl]benzoxazole (e.g. J. Neuroscience 24 (10), 2535 (2004); BSB: (trans,trans)-1-bromo-2,5-bis-(3-hydroxycarbonyl-4-hydroxy)styrylbenzene (e.g. Lab. Investigation 83(12) 1751 (2003); quinilinehydrazone compounds (e.g., 4-methyl-7-methoxy-2-(4-quinolylmethylenehydrazino)quinoline) (e.g. WO2002/024652, Thomas Raub et. al., Chrisamin G et al. Chrysamine-G, a lipophilic analogue of Congo red, inhibits A beta-induced toxicity in PC12 cells. Life Sci. 1998; 63(20):1807-14); rifampicin (e.g. Tomiyama T et al. J Biol Chem. 1996; 271:6839-6844); melatonin (e.g. Pappolla M et al. J Biol Chem. 1998; 273:7185-7188); baicalein (e.g. Zhu M et al. The flavonoid baicalein inhibits fibrillation of alpha-synuclein and disaggregates existing fibrils. J Biol Chem. 2004 Jun. 25; 279 (26):26846-57); scyllitol (e.g. Cocositol, Quercinitol, 1,3,5/ 2,4,6-Hexahydroxycyclohexane) and derivatives (e.g. Sun et al. Synthesis of scyllo-inositol derivatives and their effects on amyloid beta peptide aggregation. Bioorg Med Chem. 2008 Aug. 1; 16(15):7177-84); imaging probes, such as [11C]-PIB: N-methyl [11C] 2-(4'-methylaminophenyl-6-hydroxybenzathiazole) (e.g. Brain 130:2607 (2007)); stilbenylbenzothiazole and stilbenylbenzothiazole derivatives (e.g. Bioorganic and Medicinal Chemistry Letters 18: 1534 (2008)) and other agents as for example described in FEBS letters 583: 2593 (2009).

In certain embodiments, noninvasive and rapid urine diagnostic assays are provided. In certain embodiments, these diagnostic assays are based on Congo red affinity. In certain embodiments, the global protein misfolding load of PE patients can be assessed via a simple diagnostic test (e.g., Congo Red retention (CRR) of the urine sample). The CRR tests provided may also be used for prediction of IND, an important contributor to preterm birth.

The methods and compositions described herein enable one to assess and/or monitor the risk in a pregnant woman of developing a hypertensive disorder by detecting and/or monitoring congophilia as measured, for example, by Congo Red retention. It should be appreciated that other dyes that interact/associate with protein aggregates and/or dyes that have chemical properties similar to Congo Red may likewise be used in the methods described herein and the invention is not limited to the use of Congo Red.

In certain embodiments, diagnostic assays comprise obtaining a protein sample from a pregnant woman and testing the protein sample for congophilia. In certain embodiments, the congophilia assay is conducted by contacting the urine sample with the dye Congo Red for sufficient time to allow Congo Red incorporation (CRI) and then washing the sample with a wash solution. After washing, Congo Red Retention (CRR) by the sample indicates that the pregnant woman has developed or is at risk of developing preeclampsia. As references for Congo Red incorporation, positive and negative controls may be incorporated, e.g., from subjects with diagnosed PE and normotensive subjects, respectively. The incorporation step and/or the washing step can be controlled, for example, by including the positive and negative controls, wherein sufficient dye incorporation is indicated when the positive sample retains Congo Red (is CRR positive) after the washing step, and sufficient washing is indicated when the positive sample does not retain any Congo Red (is CRR negative) after the wash step. In certain embodiments, CRR can be visualized without the need for visualization equipment, e.g., by separation methods such as, Congo red affinity by dot blot, gel filtration, and centrifugation and washing of the precipitated Congo red bound proteins with water (see FIG. 8). In certain embodiments, the separation step may be carried out in a vessel or tube, such as a Falcon™ or Eppendorf™ tube and dye contacting (retention) and washing can occur within the vessel or tube, followed by a centrifugation step to separate (e.g., precipitate) the dye incorporated into the protein aggregates from unincorporated dye, optionally followed by additional washing steps. In certain embodiments, the samples may be spotted on a membrane that has affinity to proteins, such as nitrocellulose, and contacting and washing steps may be carried out on the membrane (e.g. dot blots).

Such tests may be performed with only limited or no supervision by trained physicians, e.g., by trained technicians, or in some embodiments may be performed by the patient/subject without requiring any supervision and/or laboratory equipment (such as through the use of a kit that includes the necessary reagents and instructions).

Applicants have found that although urine samples from a group of pregnant women vary widely in protein concentration, protein levels in urine are usually sufficiently concentrated to allow for testing of congophilia without the need to concentrate the urine sample, allowing for the design of simple analytic tests that do not require any laboratory equipment or may require only the most basic equipment.

In certain embodiments, the percent Congo Red Incorporation (% CRI) may be determined, such as by measuring optical density (OD, densitometry), compared to a negative control and multiplied by the factor 100. After washing the percent Congo Red Retention (% CRR) may be determined by measuring optical density (OD) as compared to a negative control and multiplied by the factor 100. The CRR value of the sample may then be subtracted from the corresponding value of the negative control. Sufficient washing is indicated if no residual Congo Red stain is visible in the negative control. An OD average should be 0 (if multiple controls are used).

In certain embodiments, Congo Red Retention (CRR) and Congo Red incorporation (CRI) coefficients may be calculated and samples with CRR>20% may be "called" Red Dot Test positive and those CRR<15% Red Dot Test negative.

In certain embodiments, using the diagnostic assays described herein to identify the presence of congophilic urine proteins makes it possible to identify women who develop severe preeclampsia (sPE) 8-10 weeks prior to clinical manifestations. In certain embodiments, detection of urine congophilia (e.g., by dot blot fixation and/or spectral shift assays) is indicative of a patient with preeclampsia and provides a method for diagnosis of preeclampsia. In certain embodiments, the presence of urinary congophilic protein aggregates, detected as described, is not only diagnostic of an existing preeclampsia, but also predictive of the future development of preeclampsia.

In certain embodiments, urine samples may be analyzed immediately after collection (e.g., on a dot blot, dipstick or similar) or at a later time. For example, the urine samples may be frozen at −70° C. and/or collected in a tube or vessel and dried and stored at e.g. −20° C., or 4° C. Drying of the sample may be conducted using a centrifuge under vacuum (e.g. e.g. a SpeedVac) and allows for storage and later analysis limiting the risk of sample spoiling (e.g. protein denaturation) at temperatures above freezing. It should be appreciated that drying of the sample to concentrate the sample is usually not necessary, but the samples may nevertheless be dried for reasons described herein or any other reason.

2. Protein Aggregate Conformation-Specific Antibodies for Diagnosis of PE

Applicants have unexpectedly found that PE is a conformational disorder associated with protein misfolding and aggregation, characterized by amyloid-like assembly of proteins.

Provided herein, in certain embodiments, are methods for diagnosis of preeclampsia whereby detection of protein aggregates in the urine of pregnant women using antibodies that recognize certain proteins and/or protein oligomers that have adopted a unique folding conformations is indicative of this disease.

Certain embodiments described herein are polyclonal and monoclonal antibodies that may be used to detect protein conformations associated with protein aggregation disorders such as PE. Such antibodies, in some embodiments, may include those that detect proteins in e.g. (i) a prefibrillar soluble oligomer conformation, such as the "A11" antibody, provided herein, amongst others, (ii) a ring-shaped protofibril conformation, such as the "Officer" antibody, provided herein, amongst others, and (iii) a fibril conformation, such as the "OC" antibody, provided herein amongst others.

As used herein, the term "supramolecular aggregate of misfolded proteins" (herein also referred to as "supramolecular aggregate," "abnormal protein aggregate," "supramolecular amyloid assembly" and "congophillic protein aggregate") refers to soluble protein aggregates and insoluble protein aggregates. These include: (1) pre-fibrillar oligomers (also referred to as "pre-amyloid oligomers" and "non-fibrillar misfolded protein aggregates") which are soluble and have adopted "amyloid-like" properties; (2) protofibrils; (3) fibrillar oligomers, which are soluble; and (4) amyloid fibrils, which are insoluble.

Each of those supramolecular aggregates is recognized by antibodies such as the conformation-dependent, sequence-independent antibodies described herein.

Protein aggregates with "amyloid-like" properties as used herein describe protein aggregates that may share some chemical, physical, biological characteristics with amyloid fibrils but are distinct in other chemical, physical, biological characteristics, such as, for example for certain amyloid-like protein aggregates, the structure of the aggregate.

In some embodiments, pre-fibrillar oligomers are present in the urine of patients with PE. In some embodiments, the presence of these pre-fibrillar oligomers in a sample, e.g. urine sample, may be detected using conformation-dependent, amino acid sequence-independent antibodies. In some embodiments, the antibody is A11.

In some embodiments, protofibrils are present in a sample, e.g. a urine sample of a patient with PE. In some embodiments, the presence of these protofibrils in a sample, e.g. urine sample, may be detected using conformation-dependent, amino acid sequence-independent antibodies. In some embodiments, the antibody is Officer.

In some embodiments, fibrillar oligomers and/or amyloid fibrils are present in a sample, e.g., a urine sample of a patient with PB. In some embodiments, the presence of those fibrillar oligomers and/or amyloid fibrils in a sample, e.g., urine sample, may be detected using conformation-dependent, amino acid sequence-independent antibodies. In some embodiments, the antibody is OC.

Samples, such as e.g. urine samples, obtained from PB patients or patients suspected of having PB or patients at risk of developing PE, may contain relatively few or no insoluble amyloid fibrils, but may contain any one of or a mixture of soluble supramolecular aggregates, such as pre-fibrillar oligomers, fibrillar oligomers, and/or protofibrils.

Antibodies that recognize supramolecular aggregates in a conformation-dependent, amino acid sequence-independent manner may be raised in animals, such as e.g. mice or rabbit, using preparations comprising pre-fibrillar aggregates (oligomers), fibrillar aggregates (oligomers), protofibrils or fibrils comprising polypeptides with "amyloid-like" properties that may form such pre-fibrillar aggregates, fibrillar aggregates, protofibrils and/or amyloid fibrils. Peptides with "amyloid-like" properties are known in the art, including amyloid beta (Aβ) peptides, such as e.g. Aβ(1-40) or Aβ(1-42), and polyglutamine (polyGln) molecule $NH_2$-$KKQ_{42}KK$-COOH and are described for example in Example 4, Kayed et al. Mol Neurodegenr. 2007; 2: 18; Hrncic et al. Am J Pathol. 2000; 157:1239-1246; O'Nuallain B et al. Proc Natl Acad Sci USA. 2002; 99:1485-1490, references incorporated herein).

Animals can be immunized with morphologically homogeneous populations of fibrils, for example to generate conformation-dependent, amino acid sequence-independent antibodies that specifically recognize fibrils and/or fibrillar aggregates. Some of the resulting antibodies may specifically recognize fibrils and/or fibrillar aggregates and do not recognize (do not cross-react with) random coil monomers, pre-fibrillar oligomers, or natively folded precursor proteins.

Alternatively, animals can be immunized with morphologically amorphous populations of pre-fibrillar aggregates, for example to generate conformation-dependent, amino acid sequence-independent antibodies that specifically recognize pre-fibrillar aggregates. Some of the resulting antibodies may specifically recognize pre-fibrillar aggregates and do not recognize (do not cross-react with) fibrillar oligomers, amyloid fibrils, monomers or natively folded precursor proteins.

Alternatively, animal can be immunized with populations of protofibrils, for example to generate conformation-dependent, amino acid sequence-independent antibodies that specifically recognize ring-shaped protofibril. Some of the resulting antibodies may specifically recognize protofibrils and do not recognize (do not cross-react with) pre-fibrillar oligomers, fibrillar oligomers, amyloid fibrils, monomers or natively folded precursor proteins.

Applicants have shown that the specificity of detection of PB associated abnormal protein conformations (supramolecular aggregates) is significantly improved when the secondary antibody used for detection is preabsorbed with human IgG to reduce the non-specific binding. This is based, in part, on the finding by Applicant that PE-associated aggregated proteins in supramolecular aggregates include human immunoglobulins or fragments thereof. Cross-reactivity of a secondary antibody that has not been pre-adsorbed leads to non-specific binding of the secondary antibody. In certain embodiments, methods for detecting PE associated abnormal protein conformations from urine samples are provided. Such methods comprise obtaining a urine sample from a pregnant woman who has or is suspected of having or being at risk of developing PE; contacting the urine sample with a primary antibody (polyclonal or monoclonal) specific for (that binds) conformations associated with protein aggregation disorders, under conditions under which misfolded protein aggregate-antibody binding occurs, thereby producing a combination; contacting the combination with a secondary antibody that is preabsorbed with human IgG to reduce non-specific binding and determining if misfolded protein aggregate-antibody complexes are present in the urine sample, wherein the presence of misfolded protein aggregate-antibody complexes (abnormal protein conformations) in the urine sample is indicative of PB.

In certain embodiments, the protein aggregates are contacted with A11 primary antibody, described herein, and subsequently with preabsorbed secondary antibody, wherein A11 positivity in the assay is correlated with severity of the PE symptoms.

It should be appreciated that any secondary antibody that is suitable for detection of the primary antibody cm be used as long as the secondary antibody is sufficiently preabsorbed with human IgG to reduce or prevent non-specific binding and the invention is not limited in this aspect. The secondary antibody may be labeled with any label to allow detection, including but not limited to radioisotopic labels, enzyme labels, non-radioactive isotopic labels, fluorescent labels, toxin labels, affinity labels, chemiluminescent labels and nuclear magnetic resonance contrast agents. It should also be appreciated that one of ordinary skill can easily modify or adopt the detection system for different purposes, e.g., high-throughput and/or automated screening, using various labeling and/or detection systems known in the art and the invention is not limited in this aspect. Further, it should be appreciated that the antibodies described herein are intended to be examples and one of ordinary skill can generate additional antibodies having the characteristics described herein using the methods described herein and/or methodologies known in the art without the need for undue experimentation. Antibodies other than those described herein, including, but not limited to, whole antibodies, monoclonal antibodies, polyclonal antibodies, chimeric antibodies, humanized antibodies, primatized antibodies, multi-specific antibodies, single chain antibodies, epitope-binding fragments, fragments comprising either a VL or VH domain, and totally synthetic and recombinant antibodies that have the characteristics described herein, e.g., that recognize protein aggregates and/or misfolded or aberrant protein conformations and/or specific protein fragments (e.g., those of biomarker proteins described herein) also form part of the invention.

In certain embodiments, monoclonal antibodies are provided that recognize protein aggregates and/or misfolded or aberrant protein conformation. In certain embodiments, monoclonal antibodies are provided that are raised against the same antigen as the A11 antibody (Science 300: 486-489, 2003), with preferential affinities for different types of prefibrillar protein oligomer conformation. In certain embodiments, monoclonal antibodies #204, #205 and #89 are provided that show immunoreactivity for protein aggregates and demonstrate the ability to detect these protein aggregates in the urine of preeclampsia patients but not in controls. In certain embodiments, monoclonal antibodies that recognize different conformations of prefibrillar protein oligomers, such as monoclonal #204, #205 and #89 are used in the diagnosis of preeclampsia.

Urinary protein aggregates, detected as described, are not only diagnostic of an existing preeclampsia, but are also predictive of the future development of preeclampsia. In addition to detecting the presence of protein aggregates in the urine, placental tissue samples can display characteristic features of such protein aggregates. This methodology of detecting abnormally folded proteins and protein aggregates in the placenta with selective antibodies also has application in the diagnosis of preeclampsia. In certain embodiments, antibodies that bind to protein oligomers are provided that have therapeutic potential e.g., by (i) disrupting protein oligomers/aggregates; (ii) preventing further growth of protein oligomers/aggregates (iii) stabilizing protein oligomers/aggregates to prevent them from converting into a more pathological confirmation(s); and/or (iv) converting protein oligomers/aggregates from a pathological to a non-pathological conformation(s).

Such a therapeutic approaches have been used to treat Alzheimer's disease, e.g., using antibodies against the beta-amyloid protein. Applicants have found that preeclampsia is a disease associated with the accumulation of abnormal protein oligomers. In certain embodiments, antibodies with affinity for unique conformations of abnormally folded proteins, such as e.g., the monoclonal antibodies #204, #205 and #89-17 described herein, or similar, are used as therapeutic agents for the treatment of preeclampsia.

Applicants have found that protein aggregates present in urine of subjects with PE that comprise one or more of immunoglobulin heavy and light chains, ceruloplasmin and the interferon-inducible protein 6-16 (IFI-6) also have therapeutic potential in treating preeclampsia. In certain embodiments, methods for the diagnosis or prognosis of preeclampsia are provided comprising quantitation of one or more of proteins, such as e.g., immunoglobulin heavy and light chains, ceruloplasmin and the interferon-inducible protein 6-16, in protein aggregates in the placenta and/or the urine from preeclampsia patients. In certain embodiments, the quantitation of the proteins comprises relative protein concentration of these proteins when compared to a standard, e.g., obtained from a normotensive control subject. In certain embodiments, antibodies specific for immunoglobulin heavy and light chains, ceruloplasmin or the interferon-inducible protein 6-16 are used.

In certain embodiments, antibodies are provided that are specific for conformational epitopes of misfolded protein aggregates found in urinary samples of patients having, suspected of having or at risk of developing PE and that are useful for the detection of PE. Antibodies provided herein include polyclonal and monoclonal antibodies, as well as antibody fragments and derivatives that contain the relevant antigen binding domain of the antibodies. The term "antibody" as used herein refers to immunoglobulin molecules or other molecules which comprise at least one antigen-binding domain. The term "antibody" as used herein is intended to include whole antibodies (e.g. IgG, IgA, IgE, IgM, or IgD), monoclonal antibodies, polyclonal antibodies, chimeric antibodies, humanized antibodies, primatized antibodies, multi-specific antibodies, single chain antibodies, epitope-binding fragments, e.g., Fab, Fab' and F(ab'), Fd, Fv, single-chain Fvs (scFv), disulfide-linked Fvs (sdFv), fragments comprising either a VL or VH domain, and totally synthetic and recombinant antibodies.

Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In certain embodiments, polyclonal antibodies are provided, such as e.g., the "Officer," "OC," and "A11" polyclonal antibody. Monoclonal and polyclonal antibodies can be produced in vivo in response to immunization with different epitopes on an immunogen, e.g., oligomeric aggregates (pre-fibrillar, fibrillar), protofibrillar aggregates or aggregates comprising amyloid fibrils. These aggregates may be conformationally homogenous or heterogenous/amorphous.

Anti-serum may be raised in a wide range of animals with one or more injections of an antigen optionally along with a non-specific enhancer of the immune response, such as an adjuvant. For many small molecules or haptens, a carrier protein, which may provide determinants recognized by helper T-cells, may be required for conjugation via various bi-functional coupling reagents. Homogenous or heterogenous/amorphous oligomeric aggregates (pre-fibrillar, fibrillar), protofibrillar aggregates or aggregates comprising amyloid fibrils may be administered with and adjuvant, e.g., incomplete Freund's adjuvant.

Upon one or more immunizations, the antibodies produced may be predominantly IgG with some affinity to the epitope. Polyclonal antibodies provide multiple specificity. The specificity of polyclonal antibodies may be improved by affinity chromatography using purified antigen.

In certain embodiments, monoclonal antibodies are provided, such as e.g., the "M204," monoclonal antibody "M205" monoclonal antibody and "M89" monoclonal antibody. Such monoclonal antibodies and others that recognize (bind) similar partners, can be used in the methods described herein, such as of diagnosing or aiding in diagnosing preeclampsia; methods of predictive or aiding in predictive the likelihood a pregnant woman will develop preeclampsia; and methods of determining or aiding in predicting whether a pregnant woman is at risk of developing preeclampsia.

For example, the level of immunoreactivity for monoclonal 89 in urine of pregnant women is indicative of the risk and severity of HELP syndrome, an atypical form of severe preeclampsia characterized by Hemolysis, Elevated liver enzymes and Low Platelets. In HELP syndrome, early diagnosis is critical because the morbidity and mortality rates have been reported to be as high as 25 percent. The monoclonal antibody has been raised against alpha protofibrils and reacts with those formed by hemolysin which are exotoxins produced by bacteria which cause lysis of red blood cells in vitro. Results presented in this application (e.g., FIG. 13) support the use of the relative level of immunoreactivity for monoclonal 89 to that of monoclonal 204, 205 or to polyclonal A11 to determine the risk for HELLP syndrome and need for urgent intervention. Also described herein is a method of determining the risk or aiding in determining the risk (likelihood) that a pregnancy woman will develop HELLP syndrome and be in need of urgent intervention. The method comprises assessing the level of immunoreactivity in a sample (such as urine or placental tissue) for monoclonal 89 relative to that of at least one of monoclonal 204 or 205 or polyclonal A11. A difference in the relative levels of immunoreactivity (pregnant woman compared with control, such as relative immunoreactivity in a nonpreeclamptic pregnant woman or population thereof) are determined and the likelihood a pregnant woman will develop HELLP is determined or assisted.

Monoclonal antibodies may be produced in animals such as mice and rats by immunization. B cells can be isolated from the immunized animal, for example from the spleen. The isolated B cells can be fused, for example with a myeloma cell line, to produce hybridomas, that can be maintained indefinitely in in vitro cultures. These hybridomas can be isolated by dilution (single cell cloning) and grown into colonies. Individual colonies can be screened for the production of antibodies of uniform affinity and specificity. Hybridoma cells may be grown in tissue culture and antibodies may be isolated from the culture medium. Hybridoma cells may also be injected into an animal, such as a mouse, to form tumors in vivo (such as peritoneal tumors) that produce antibodies that can be harvested as intraperitoneal fluid (ascites). The lytic complement activity of serum may be optionally inactivated, for example by heating.

Specific proteins, peptides, haptens, chemical compounds, and protein aggregates, such as homogenous or heterogenous/amorphous oligomeric aggregates (pre-fibrillar, fibrillar), protofibrillar aggregates or aggregates comprising amyloid fibrils may be used to generate antibodies. One skilled in the art will recognize that the amount of polypeptides (e.g. aggregates) used for immunization will vary based on a number of factors, including the animal which is immunized, the antigenicity of the polypeptide selected, and the site of injection. The polypeptides (e.g. aggregates) used as an immunogen may be modified as appropriate or administered in an adjuvant in order to increase the peptide antigenicity. In some embodiments, polypeptides (e.g. aggregates), peptides, haptens, and small compounds may be conjugated to a carrier protein to elicit an immune response. Homogenous or heterogenous/amorphous oligomeric aggregates (pre-fibrillar, fibrillar), protofibrillar aggregates or aggregates comprising amyloid fibrils may be administered with and adjuvant, e.g. incomplete Freund's adjuvant.

Suitable methods to increase antigenicity are well known in the at, and include, for example, coupling the antigen with a heterologous protein (such as globulin or β-galactosidase) or through the inclusion of an adjuvant during immunization.

Antibody titers can be monitored e.g., by antigen-specific ELISA, western blot analysis, or radioimmunoassay. One or more animals me commonly used for antibody production. Antibodies or immunospecific fragments thereof of provided herein may be from any animal origin including rabbits, sheep, goats, chicken, mice, rats, hamsters, guinea pigs, donkey, camel, llama, or horse.

After one or more injections of the antigen, approximately 7-10 days after each boost, serum may be taken to determine the production of specific antibodies (titer). The test bleeds may be assayed against the immunogen itself, for example in an ELISA assay. Antibodies may be stored in several different buffers, for example at neutral pH, such as 0.0 IM phosphate-buffered saline (PBS) at pH 7.4, optionally containing, for example 0.1% sodium azide to inhibit microbial growth. For long-term storage, antibodies may be kept at a low temperature, such as 4° C., −20° C. or −70° C. Antibodies may be stored at >0.5 mg/mL and/or in the presence of a carrier protein (e.g., 1% bovine serum albumin (BSA)), or if frozen, for example in 50% glycerol.

Protocols for generating antibodies, including preparing immunogen, immunization of animals, and collection of antiserum may be found in Antibodies: A Laboratory Manual, E. Harlow and D. Lane, ed., Cold Spring Harbor Laboratory (Cold Spring Harbor, N.Y., 1988) pp. 55-120 and A. M. Campbell, Monoclonal Antibody Technology Laboratory Techniques in Biochemistry and Molecular Biology, Elsevier Science Publishers, Amsterdam, The Netherlands (1984).

The term "antibody fragment" as used herein is intended to include any appropriate antibody fragment which comprises an antigen-binding domain that displays antigen binding function. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab$^1$ fragments. Papain digestion can lead to the formation of Fab figments. Fab, Fab' and F(ab')$_2$, scFv, Fv, dsFv, Fd, dAbs, TandAbs, ds-cFv, dimers, minibodies, diabodies, bispecific antibody fragments and other fragments can also be synthesized by recombinant techniques or can be chemically synthesized. Techniques for producing antibody fragments are well known and described in the art. Antibody fragments, including single-chain antibodies, may comprise the variable region(s) alone or in combination with the entirety or a portion of the following: hinge region, CH1, CH2, and CH3 domains.

In some aspects, the antibody or antibody fragment comprises an antibody light chain variable region (VL) and an antibody heavy chain variable region (VII) which generally comprise the antigen binding site. In certain embodiments, the antibody or antibody fragment comprises all or a portion of a heavy chain constant region, such as an IgG1, IgG2, IgG3, IgG4, IgA1, IgA2, IgE, IgM or IgD constant region. In some aspects, the heavy chain constant region is an IgG1 heavy chain constant region, or a portion thereof. Furthermore, the antibody or antibody fragment may comprise all or a portion of a kappa light chain constant region or a lambda light chain constant region, or a portion thereof. In some aspects, the light chain constant region is a lambda light chain constant region, or a portion thereof. All or part of such constant regions may be produced naturally or may be wholly or partially synthetic. Appropriate sequences for such constant regions are well known and documented in the art.

As used herein, the term "heavy chain portion" includes amino acid sequences derived from an immunoglobulin heavy chain. A polypeptide comprising a heavy chain portion comprises at least one of a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). It will be understood by one of ordinary skill in the art that these domains (e.g., the heavy chain portions) may be modified such that they vary in amino acid sequence from the naturally occurring immunoglobulin molecule.

As used herein, the term "light chain portion" includes amino acid sequences derived from an immunoglobulin light chain. Preferably, the light chain portion comprises at least one of a VL or CL domain.

In some embodiments, the antibodies or antigen-binding fragments thereof are mammalian antibodies or antigen-binding fragments, such as mouse, rat, rabbit, or human antibodies or antigen-binding fragments.

In a certain embodiments, antibodies of the invention are human antibodies. The term "human" as used herein in connection with antibody molecules and fragments thereof refers to antibodies having variable (e.g. VH, VL, CDR or FR regions) and/or constant antibody regions derived from or corresponding to sequences found in humans, e.g., in the human germline or somatic cells.

In some embodiments, human antibodies may be used in human therapy, such as e.g, in the treatment and/or prevention of PE. In such antibodies, the effector portion may be human and hence it may interact better with the other parts of the human immune system, that is they are not recognized by the body as foreign. In certain embodiments, such antibodies have half-lives similar to naturally-occurring human antibodies.

In certain embodiments, human antibodies of the invention may also comprise one or more amino acid residues which are not naturally encoded by wild-type human nucleic acid sequences, but which have been artificially changed/introduced in order to modify the sequence of the antibody.

Recombinant techniques are preferred for generating large quantities of antibodies, antibody fragments and single chain antibodies. In general, recombinant production of antibodies, antibody fragments or derivatives thereof; uses mRNA encoding an antibody which is isolated from hybridoma cells that produce the desired antibody. This mRNA is used as a source for generating a cDNA molecule which encodes the antibody, or a fragment thereof. Once obtained, the cDNA may be amplified and expressed according to known methods in a variety of eukaryotic and prokaryotic hosts.

In certain embodiments, antibody derivatives are provided. As used herein, "antibody derivatives" contain an antibody or a fragment thereof as well as an additional moiety. Such moieties may improve the solubility, absorption, biological half-life, etc., of the antibody, decrease the toxicity of the antibody in vivo or in vitro, eliminate or attenuate any undesirable side effect of the antibody in vivo, or serve as a detectable marker of the presence of the antibody. Moieties capable of mediating such effects are well known in the art. In certain embodiments, detectably labeled antibodies are provided. An antibody is referred to as "detectably labeled" if the antibody, or fragment thereof is attached to a molecule which is capable of identification, visualization, or localization using known methods. Suitable detectable labels include radioisotopic labels, enzyme labels, non-radioactive isotopic labels, fluorescent labels, toxin labels, affinity labels, chemiluminescent labels and nuclear magnetic resonance contrast agents.

In certain embodiments hybrid cell lines are provided that secrete monoclonal antibodies selective for specific supramolecular aggregate conformations, such as the specific conformations found in pre-fibrillar oligomers, fibrillar oligomers, ring-shaped protofibrils or amyloid fibrils.

In certain embodiments, these monoclonal antibodies may be used for treatment and/or prevention of PE, as described herein. These monoclonal antibodies can also be used for qualitative and/or quantitative measurement of PE-associated aggregates of misfolded proteins, e.g., in urine samples. These PE-associated aggregates of misfolded proteins display specific oligomeric conformations that may be detected and measured by the monoclonal antibodies provided herein and the presence of these oligomeric conformations is predictive of the likelihood of having developed PE and/or the risk of developing symptoms of PB.

3. SerpinA1 and Albumin as PE Biomarkers

Applicants have previously demonstrated, using proteomic technology (SELDI-TOF mass spectroscopy) coupled with standard molecular and biochemical identification assays, that women with preeclampsia have higher levels of SerpinA1 polypeptides and/or albumin polypeptides in their urine and other fluids and tissues, than do women without preeclampsia (U.S. application Ser. No. 12/084,004 (PCT/US2006/042585), incorporated herein by reference in their entirety).

In certain aspects, the present invention relates to methods of detecting and/or measuring SerpinA1 polypeptides and/or albumin polypeptides in a sample from a subject (e.g., urine) for determining preeclampsia status. In some embodiments, SELDI-based methods of identifying subjects with preeclampsia may be used. Such methods may include a step for detecting the level of up to 13 SerpinA1 and albumin polypeptide biomarkers. The method is based, in part, on a correlation between the presence of SerpinA1 and albumin polypeptide biomarkers and the presence of preeclampsia. Thirteen SerpinA1 and albumin polypeptide biomarkers have previously been identified (U.S. application Ser. No. 12/084,004 (PCT/US2006/042585)), a subset me set forth herein as SEQ ID NOs: 1-6 [MIEQNTKSPLFPMKVVNPTQK (SEQ ID NO:1); $M_{ox}$IEQNTKSPLFMOKVVNPTQK (SEQ ID NO:2); $M_{ox}$IEQNTKSPLFM$_{ox}$GKVVNPTQK (SEQ ID NO:3); EDPQGDAAQKTDTSHHDQDHPTFNKITPNLAEFAFS (SEQ ID NO:4); DAHKSEVAHRFKDLGEENFKALVL (SEQ ID NO:5); DAHKSEVAHRFKDLGEENFKALVLIA (SEQ ID NO:6)]. As used herein, the term "albumin polypeptide" is mean to refer to full-length albumin polypeptide and also refers to a polypeptide that is a fragment of full-length albumin polypeptide. Examples of albumin polypeptide biomarkers are set forth herein as SEQ ID NOs: 5 and 6 [DAHKSEVAHRFKDLGEENFKALVL (SEQ ID NO:5); and DAHKSEVAHRFKDLGEENFKALVLIA (SEQ ID NO:6)]. The wild-type, full-length amino acid sequence of albumin has Genbank Accession No. P02768.

It has been found that the presence in a sample from a patient (pregnant woman) of a number of the 13 biomarkers that is above certain cut-off values indicates the presence of preeclampsia in the pregnant woman. In such embodiments of the invention, two objective urinary proteomic scores (UPS) are calculated: a Boolean score (UPSb), which represents the sum of Boolean indicators assigned to each of the 13 biomarkers complemented by a ranked score (UPSr), which retains the quantitative information of the 13 biomarkers with Boolean indicators of 1 (i.e., objectively present) and is calculated as a rounded integer with the following formula: UPSr=[S/N/10]+1, with S/N=signal to noise from SELDI analysis. Thus, in theory, the UPSb ranges from 0 to a maximum of 13 (one for each of the SerpinA1 and albumin polypeptide biomarkers) and the UPSr can range from 0 to infinity. Optimum cut-off values as used for both UPSb and UPSr to discriminate between subjects with severe preeclampsia and controls without severe preeclampsia. A UPSb level greater than six and a UPSr level greater than 8 indicate that the subject has severe preeclampsia. A UPSb level less than 6 and a UPSr level less than 8 indicate that the subject does not have severe preeclampsia. If a sample is determined to have any other combination of values for UPSb and UPSr, a subsequent sample may be obtained from the subject at a time of 1, 2, 3, 4, 5, 6, or more days after the first sample was obtained and the second sample may be tested using methods of the invention to determine the status of the subject with respect to preeclampsia. Test sample preparation, detection and measurement of biomarkers, and diagnosis methods are described herein and also in (U.S. application Ser. No. 12/084,004 (PCT/US2006/042585)).

4. VEGF, PlGF and sFlt-1 as PE Biomarkers

Studies have reported that maternal serum concentrations of vascular endothelial growth factor (VEGF), placental growth factor (PlGF) and soluble fine-like tyrosine kinase-1 (sFlt-1) are altered in patients with clinical preeclampsia (Levine R J et al. N Engl J Med 2004:12; 350:672-83; Maynard S E et al. J Clin Invest 2003; 111:649-58; Levine R J et al. N Engl J Med 2004: 12; 350: 672-83). Applicants have previously shown that endothelial growth factor (VEGF), placental growth factor (PlGF) and soluble fms-like tyrosine kinase-1 (sFlt-1) can serve as a biomarkers for early detection of preeclampsia (U.S. Publ. No: US-2006-0183175; PCT/US2005/047010, incorporated herein by reference in their entirety). Applicants demonstrated that urinary sFlt-1 is significantly increased and urinary PlGF is significantly decreased in pregnant women with hypertensive disorders. In certain embodiments, the invention features methods for measuring the concentration of PlGF and sFlt-1 in a urine sample and utilizing the ratio of such opposing growth factors to differentiate pregnant women with severe preeclampsia from pregnant women with other forms of hypertensive disorders, including mild preeclampsia with or without chronic hypertension, or from normotensive controls. The methods of the invention may also be used to assess the risk of a pregnant woman developing a specific complication of hypertensive disorders, including preeclampsia. Such complications may include delivery by cesarean section, increased serum uric acid, increased systolic and diastolic blood pressures, dipstick proteinuria, gravidity, fetal weight at delivery, placental abruption, IUGR, hemolysis, thrombocytopenia, elevated liver enzymes and HELLP syndrome (hemolysis, elevated liver enzymes, low platelet count).

In certain embodiments, a formula is used to analyze results of determination of concentrations or levels of biomarkers. The resulting value provides information with respect to the likelihood that the pregnant woman will develop a hypertensive disorder, such as preeclampsia. As used herein, the term "formula" refers to any mathematical expression, algorithm or other metric that is useful in evaluating whether the levels of an biomarker(s) of interest indicate that a pregnant woman has or is at risk of developing a hypertensive disorder and/or specific complications of hypertensive disorders.

In one embodiment, the formula is used to calculate the pregnant woman's uFP. For purposes of this invention, the term "uFP" refers to the log [sFlt-1/PlFG×100]. In one aspect of the invention, a uFP in excess of 1.4 is a prognostic indicator of an increased risk that a pregnant woman will require treatment to prevent the development of or worsening of symptoms associated with hypertensive disorders. In another aspect of the invention, a uFP in excess of 2.1 indicates that a pregnant woman has or is at risk for developing severe preeclampsia. In a further aspect of the invention, a uFP in excess of 2.1 indicates that a pregnant woman is at risk for delivering by cesarean section.

Teat sample preparation, detection and measurement of biomarkers, and diagnosis methods are described herein and also in (U.S. Publ. No: US-2006-0183175; PCT/US2005/047010)

5. Test Sample Preparation (for Certain Embodiments of the Invention)

In certain aspects, a sample from a subject may be a sample collected from a pregnant subject, e.g., a pregnant subject in whom preeclampsia status is to be assessed. A pregnant subject may be a pregnant woman who has been determined to have a high risk of preeclampsia based on her personal or family history. A pregnant subject may be a subject who has previously been diagnosed with chronic hypertension. Other subjects may include pregnant subjects who are known to have preeclampsia. In some embodiments, the methods of the invention may be used to monitor a subject diagnosed with preeclampsia, for example to determine the effectiveness of a therapy or treatment administered to the preeclamptic subject. Also, a subjects may be a healthy pregnant woman who is being tested for preeclampsia as part of a routine examination, or to establish a baseline level (e.g., a control or reference level) of the biomarkers in the subject or for other subjects. In other aspects, a sample may be collected from a pregnant non-human mammal, or a non-pregnant subject, for example, for use in methods to identify a compound to treat preeclampsia.

Urine samples may be analyzed immediately after collection or at a later time, provided that, when analyzed, the sample contains detectable levels of the biomarker(s) of interest. For example, the urine samples may be frozen at −70° C. and/or mixed, combined or stored in a container pretreated with agents that stabilize or preserve the biomarker(s) of interest. In a preferred embodiment, the urine sample is collected from the first morning void.

Biomarkers of the invention can be measured in different types of biological samples, preferably biological fluid samples such as urine. Biomarkers of the invention may also be assessed in tissues and/or in other biological fluid samples. Examples of other biological fluid samples that may be used in methods and kits of the invention, although not intended to be limiting include blood, blood serum, plasma, vaginal secretions, CSF, tears, and saliva. If desired, a sample can be prepared to enhance detectability of the biomarkers. For example, a urine sample from the subject can be fractionated. Any method that enriches for a biomarker polypeptide of interest can be used. Sample preparations, such as prefractionation protocols, are optional and may not be necessary to enhance detectability of biomarker depending on the methods of detection used. For example, sample preparation may be unnecessary if an antibody that specifically binds a biomarker is used to detect the presence of the biomarker in a sample. Sample preparation may involve fractionation of a sample and collection of fractions determined to contain the biomarkers. Methods of prefractionation include, for example, size exclusion chromatography, ion exchange chromatography, heparin chromatography, affinity chromatography, sequential extraction, gel electrophoresis and liquid chromatography. Examples of methods of fractionation are described in PCT/US03/00531 (incorporated herein in its entirety).

As an example, a sample is pre-fractionated by anion exchange chromatography. Anion exchange chromatography allows pre-fractionation of the proteins in a sample roughly according to their charge characteristics. For example, a Q anion-exchange resin can be used, and a sample can be sequentially eluted with eluants having different pHs. Anion exchange chromatography allows separation of biomolecules in a sample that are more negatively charged from other types of biomolecules. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

As another example, biomolecules in a sample can be separated by high-resolution electrophoresis, e.g., one or two-dimensional gel electrophoresis. A fraction containing a biomarker can be isolated and further analyzed by gas phase ion spectrometry. Preferably, two-dimensional gel electrophoresis is used to generate two-dimensional array of spots of biomolecules, including one or more biomarkers. See, e.g., Jungblut and Thiede, Mass Spectr. Rev. 16:145-162 (1997). The two-dimensional gel electrophoresis can be performed using methods known in the art See, e.g., Deutscher ed., Methods In Enzymology vol. 182. In certain cases, biomolecules in a sample are separated by, e.g., isoelectric focusing, during which biomolecules in a sample are separated in a pH gradient until they reach a spot where their net charge is zero (isoelectric point). This first separation step results in one-dimensional array of biomolecules. The biomolecules in one-dimensional array is further separated using a technique generally distinct from that used in the first separation step. Typically, two-dimensional gel electrophoresis can separate chemically different biomolecules in the molecular mass range from 1000-200,000 Da within complex mixtures. The pI range of these gels is about 3-10 (wide range gels).

As another example, high performance liquid chromatography (HPLC) can also be used to separate a mixture of biomolecules in a sample based on their different physical properties, such as polarity, charge and size. HPLC instruments typically consist of a reservoir of mobile phase, a pump, an injector, a separation column, and a detector.

Biomolecules in a sample are separated by injecting an aliquot of the sample onto the column. Different biomolecules in the mixture pass through the column at different rates due to differences in their partitioning behavior between the mobile liquid phase and the stationary phase. A fraction that corresponds to the molecular weight and/or physical properties of one or more biomarkers can be collected. The fraction can then be analyzed by gas phase ion spectrometry to detect biomarkers. For example, the spots can be analyzed using either MALDI or SELDI as described herein.

Optionally, a biomarker can be modified before analysis to improve its resolution or to determine its identity. For example, the biomarkers may be subject to proteolytic digestion before analysis. Any suitable protease may be used. Proteases, such as trypsin, that are likely to cleave the biomarkers into a discrete number of fragments are particularly useful. The fragments that result from digestion may function as a fingerprint for the biomarkers, thereby enabling their detection indirectly. This is particularly useful where there are biomarkers with similar molecular masses that might be confused for the biomarker in question. Also, proteolytic fragmentation is useful for high molecular weight biomarkers because smaller biomarker, are more easily resolved by mass spectrometry. Optionally, the identity of the biomarkers can be further determined by matching the physical and chemical characteristics of the biomarkers in a protein database (e.g., SwissProt).

In certain embodiments, the invention comprises treating the urine sample(s) from the pregnant woman with one or more stabilizing agent and/or pretreating the container used for collection of such urine sample(s) with one or more stabilizing agent prior to measuring the levels of angiogenic markers. The term "stabilizing agent" refers to one or more molecules, such as polypeptides or nucleic acids, that can be used to prevent the degradation of the angiogenic markers. In one embodiment, the stabilizing agent is a protease inhibitor, including any of 4-(2-Aminoethyl) benzenesulphonyl fluoride (AEBSF) and Pefabloc SC, Antipain and Antipain-dihydrochloride, Aprotinin, Benzamidine and Benzamidine hydrochloride, Bestatin, Chymostatin, E-64 (L-trans-epoxysuccinyl-leucylamide-(4-guanido)-butane or N—[N-(L-trans-carboxyoxiran-2-carbonyl)-L-leucyl]-agmatine), Ethylenediaminetetraacetic acid and its sodium salt (EDTA-Na2), Leupeptin, Ethylmaleimide, Pepstatin and Pepstatin A, Phosphoramidon, Sodium aside, Trypsin inhibitor or ε-aminocaproic acid.

5. Detection and Measurement of Biomarkers (or Certain Embodiments of the Invention)

Levels of a biomarker for PB (e.g. SerpinA1 polypeptides and albumin polypeptides, VEGF polypeptides, sFlt-1 polypeptides, and PlGF polypeptides) that is useful in a method of the present invention may be assessed by any of a wide variety of well known methods for detecting expression of a transcribed molecule or its corresponding protein. Non-limiting examples of such methods include immunological methods for detection of secreted proteins, protein purification methods, protein function or activity assays, nucleic acid hybridization methods, nucleic acid reverse transcription methods, and nucleic acid amplification methods. In one embodiment, levels of a bio marker is assessed using an ELISA assay.

Methods and compositions described herein permit assessment and/or monitoring risk in a pregnant woman of developing preeclampsia by detecting and/or monitoring levels of biomarkers for PE (e.g. SerpinA1 polypeptides and albumin polypeptides, VEGF polypeptides, sFlt-1 polypeptides, and PlGF polypeptides) in a sample obtained from the pregnant woman. This can be carried out by obtaining a urine sample and detecting levels of biomarkers of the invention, as described herein, at varied times as the pregnancy progresses. Resulting values may also be compared to a control or known (pre-established) standard. As used herein, the terms "appropriate standard" or "control" refers to the levels of the biomarker in urine obtained from a reference subject. The appropriate standard concentration can be determined from urine samples obtained from pregnant women with normal pregnancies or from pregnant women who have a confirmed hypertensive disorder, such as preeclampsia (reference or control subjects). In some embodiments of the invention, samples that form the basis of an appropriate standard are obtained from the reference subject who, when the sample is obtained, is in the week of pregnancy corresponding to that week of pregnancy the test subject is in when the test sample is obtained. Samples may be obtained and analyzed at the same time as urine samples are obtained from test subjects. Alternatively, PE biomarker levels (e.g. levels of SerpinA1 polypeptides and albumin polypeptides, VEGF polypeptides, sFlt-1 polypeptides, and PlGF polypeptides) may be determined prospectively or retrospectively to the assessment of the urine sample obtained from a test subject using statistical studies with routine experimentation. Standard PB biomarker levels (e.g., standard levels for SerpinA1 polypeptides and albumin polypeptides, VEGF polypeptides, sFlt-1 polypeptides, and PlGF polypeptides) can be determined by a person having ordinary skill in the art using well known methods.

Biomarkers such as SerpinA1 polypeptides and albumin polypeptides are preferably captured with capture reagents immobilized to a solid support, such as any biochip described herein, a multiwell microtiter plate, a resin, or other suitable support. A preferred mass spectrometric technique for use in the invention is Surface Enhanced Laser Desorption and Ionization (SELDI), as described, for example, in U.S. Pat. Nos. 5,719,060 and 6,225,047, in which the surface of a probe that presents the analyte to the energy source plays an active role in desorption/ionization of analyte molecules. In this context, the tem "probe" refers to a device adapted to engage a probe interface and to present an analyte to ionizing energy for ionization and introduction into a gas phase ion spectrometer, such as a mass spectrometer. A probe typically includes a solid substrate, either flexible or rigid, that has a sample-presenting surface, on which an analyte is presented to the source of ionizing energy.

One version of SELDI, called "Surface-Enhanced Affinity Capture" or "SEAC," involves the use of probes comprised of a chemically selective surface ("SELDI probe"). A "chemically selective surface" is one to which is bound either the adsorbent, also called a "binding moiety," or "capture reagent," or a reactive moiety that is capable of binding a capture reagent, e.g., through a reaction forming a covalent or coordinate covalent bond.

The phrase "reactive moiety" here denotes a chemical moiety that is capable of binding a capture reagent. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact noncovalently with histidine containing peptides. A "reactive surface" is a surface to which a reactive moiety is bound. An "adsorbent" or "capture reagent" can be any material capable of binding a biomarker of the invention. Suitable adsorbents for use in SELDI, according to the invention, are described in U.S. Pat. No. 6,225,047.

One type of adsorbent is a "chromatographic adsorbent," which is a material typically used in chromatography. Chromatographic adsorbents include, for example, ion exchange materials, metal chelators, immobilized metal chelates, hydrophobic interaction adsorbents, hydrophilic interaction adsorbents, dyes, mixed mode adsorbents (e.g., hydrophobic attraction/electrostatic repulsion adsorbents). "Biospecific adsorbent" is another category, for adsorbents that contain a biomolecule, e.g., a nucleotide, a nucleic acid molecule, an amino acid, a polypeptide, a simple sugar, a polysaccharide, a fatty acid, a lipid, a steroid or a conjugate of these (e.g., a glycoprotein, a lipoprotein, a glycolipid). In certain instances, the biospecific adsorbent can be a macromolecular structure such as a multiprotein complex, a biological membrane or a virus. Illustrative biospecific adsorbents are antibodies, receptor proteins, and nucleic acids. A biospecific adsorbent typically has higher specificity for a target analyte than a chromatographic adsorbent.

Another version of SELDI is Surface-Enhanced Neat Desorption (SEND), which involves the use of probes comprising energy absorbing molecules that are chemically bound to the probe surface ("SEND probe"). The phrase "Energy absorbing molecules" (EAM) denotes molecules that are capable of absorbing energy from a laser desorption ionization source and, thereafter, contributing to desorption and ionization of analyte molecules in contact therewith. The EAM category includes molecules used in MALDI, frequently referred to as and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. The category also includes EAMs used in SELDI, as enumerated, for example, by U.S. Pat. No. 5,719,060.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g, to laser light. For instance, see U.S. Pat. No. 5,719,060. SEPAR and other forms of SELDI are readily adapted to detecting a biomarker or biomarker profile, pursuant to the present invention.

The detection of the biomarkers according to the invention can be enhanced by using certain selectivity conditions, e.g., adsorbents or washing solutions. The phrase "wash solution" refers to an agent, typically a solution, which is used to affect or modify adsorption of an analyte to an adsorbent surface and/or to remove unbound materials from the surface. The elution characteristics of a wash solution can depend, for example, on pH, ionic strength, hydrophobicity, degree of chaotropism, detergent strength, and temperature.

In some embodiments of the invention, a sample is analyzed by means of a "biochip," a term that denotes a solid substrate having a generally planar surface, to which a capture reagent (adsorbent) is attached. Frequently, the surface of a biochip comprises a plurality of addressable locations, each of which has the capture reagent bound there. A biochip can be adapted to engage a probe interface and, hence, function as a probe, which can be inserted into a gas phase ion spectrometer, preferably a mass spectrometer. Alternatively, a biochip of the invention can be mounted onto another substrate to form a probe that can be inserted into the spectrometer.

A variety of biochips is available for the capture of biomarkers, in accordance with the present invention, from commercial sources such as Ciphergen Biosystems (Fremont, Calif.), Packard BioScience Company (Meriden, Conn.), Zyomyx (Hayward, Calif.), and Phylos (Lexington, Mass.). Exemplary of these biochips are those described in U.S. Pat. Nos. 6,225,047, 6,329,209, and in PCT Publication Nos. WO 99/151773 and WO 00/56934.

More specifically, biochips produced by Ciphergen Biosystems have surfaces presented on an aluminum substrate in strip form, to which are attached, at addressable locations, chromatographic or biospecific adsorbents. The surface of the strip is coated with silicon dioxide.

Illustrative of Ciphergen ProteinChip® arrays are biochips H4, SAX-2, WCX-2, and IMAC-3, which include a functionalized, crosslinked polymer in the form of a hydrogel, physically attached to the surface of the biochip or covalently attached through a silane to the surface of the biochip. The H4 biochip has isopropyl functionalities for hydrophobic binding. The SAX-2 biochip has quaternary ammonium functionalities for anion exchange. The WCX-2 biochip has carboxylate functionalities for cation exchange. The IMAC-3 biochip has nitriloacetic acid functionalities that adsorb transition metal ions, such as $Cu^{++}$ and $Ni^{++}$, by chelation. These immobilized metal ions, in turn, allow for adsorption of biomarkers by coordinate bonding.

A substrate with an adsorbent is contacted with the urine sample for a period of time sufficient to allow biomarker that may be present to bind to the adsorbent. After the incubation period, the substrate is washed to remove unbound material. Any suitable washing solutions can be used; preferably, aqueous solutions are employed. An energy absorbing molecule then is applied to the substrate with the bound biomarkers. As noted, an energy absorbing molecule is a molecule that absorbs energy from an energy source in a gas phase ion spectrometer, thereby assisting in desorption of biomarkers from the substrate. Exemplary energy absorbing molecules include, as noted above, cinnamic acid derivatives, sinapinic acid and dihydroxybenzoic acid. Preferably sinapinic acid is used.

Once captured on a substrate, e.g., biochip or antibody, any suitable method can be used to measure one or more biomarkers in a sample. For example, biomarkers can be detected and/or measured by a variety of detection methods including for example, gas phase ion spectrometry methods, optical methods, electrochemical methods, atomic force microscopy and radio frequency methods. Using these methods, one or more biomarkers can be detected.

In one embodiment, methods of detection and/or measurement of the biomarkers use mass spectrometry and, in particular, SELDI. SELDI refers to a method of desorption/ionization gas phase ion spectrometry (e.g., mass spectrometry) in which the analyte is captured on the surface of a SELDI probe that engages the probe interface. In "SELDI MS," the gas phase ion spectrometer is a mass spectrometer. SELDI technology is described in more detail above.

In another embodiment, an immunoassay can be used to detect and analyze biomarkers in a sample. An immunoassay is an assay that uses an antibody to specifically bind an antigen (e.g., a biomarker). An immunoassay is characterized by the use of specific binding properties of a particular antibody to isolate, target, and/or quantify the antigen. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a biomarker from specific species such as rat, mouse, or human can be selected to obtain only those polyclonal antibodies that are specifically reactive with that biomarker and not with other proteins, except for polymorphic variants and alleles of the biomarker. This selection may be achieved by subtracting out antibodies that cross-react with the biomarker molecules from other species.

Using purified biomarkers or their nucleic acid sequences, antibodies that specifically bind to a biomarker (e.g., SerpinA1 polypeptide or albumin polypeptide) can be prepared using any suitable methods known in the art. See, e.g., Coligan, Current Protocols in Immunology (1991); Harlow & Lane, Antibodies: A Laboratory Manual (1988); Goding, Monoclonal antibodies: Principles and Practice (2d ed. 1986); Kohler & Milstein, Nature 256:495-497 (1975); Huse et al., Science 246:1275-1281 (1989); Ward et al., Nature 341:544-546 (1989).

Generally, a sample obtained from a subject can be contacted with the antibody that specifically binds the biomarker. Optionally, the antibody can be fixed to a solid support to facilitate washing and subsequent isolation of the complex, prior to contacting the antibody with a sample. Examples of solid supports include glass or plastic in the form of e.g., a microtiter plate, a stick, a bead, or a microbead. Antibodies can also be attached to a probe substrate or a protein chip.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads, fluorescent dyes, radiolabels, enzymes (e.g., horse radish peroxidase, alkaline phosphatase and others commonly used in an ELISA), and colorimetric labels such as colloidal gold or colored glass or plastic beads. Alternatively, the biomarker in the sample can be detected using an indirect assay, wherein, for example, a second, labeled antibody is used to detect bound biomarker-specific antibody, and/or in a competition or inhibition assay wherein, for example, a monoclonal antibody which binds to a distinct epitope of the biomarker is incubated simultaneously with the mixture.

Methods for measuring the amount or presence of an antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a gating coupler waveguide method or interferometry). Optical methods include microscopy (both confocal and non-confocal), imaging methods and non-imaging methods. Electrochemical methods include voltammetry and amperometry methods. Radio frequency methods include multipolar resonance spectroscopy. Useful assays are well known in the art, including, for example, as enzyme immune assay (EIA) such as enzyme-linked immunosorbent assay (ELISA), a radioimmune assay (RIA), a Western blot assay, or a slot blot assay.

Immunoassays can be used to determine presence or absence of a biomarker in a sample as well as the quantity of a biomarker in a sample. The amount of an antibody-marker complex can be determined by comparing to a standard. A standard can be, e.g., a known compound or another protein known to be present in a sample. It is understood that the test amount of biomarker need not be measured in absolute units, as long as the unit of measurement can be compared to a control.

When the sample is measured and data is generated, e.g., by mass spectrometry, the data may then be analyzed by a computer software program. In certain cases, a biomarker bound to the substrate can be detected in a gas phase ion spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Generally, data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set as zero in the scale.

A computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen, in another useful format, two or more spectra are compared, conveniently highlighting unique biomarkers and biomarkers that are up- or downregulated between samples. Using any of these formats, one can readily determine whether a particular biomarker is present in a sample.

Software used to analyze the data can include code that applies an algorithm to the analysis of the signal to determine whether the signal represents a peak in a signal that corresponds to a biomarker according to the present invention. Software also can subject the data regarding observed biomarker peaks to classification tree or artificial neural network (ANN) analysis, to determine whether a biomarker peak or combination of biomarker peaks is present that indicates a diagnosis of intra-amniotic inflammation.

7. Multiple/Combined Analysis of PE

In certain embodiments, methods are provided that are diagnostic and/or predictive for PE comprising utilizing one or more assays to measure one or more biomarkers for PE, thereby confirming with the subsequent assay the results obtained from the previous assays and/or obtaining additional quantitative and/or qualitative results that improve predictive value of the test and/or lead to a higher degree of confidence in diagnostic tests. For example, initially simple Congo Red Retention assays may be performed (e.g. dot blots) to give first indication that a subject has developed or is at risk of developing preeclampsia. This first test may be carried out by the subject without the need for supervision and/or laboratory equipments, or with only limited technical expertise and/or equipment required.

If the Congo Red Retention assays is positive, it may be quantified as described herein. This indication may then also be predictive of the severity of PE. In addition to the Congo Red Retention assays, or a similar dye-based say, samples may be subjected to antibody-based assay described herein, using e.g., antibodies that detect specific conformations of misfolded protein aggregates. These test may be carried out on the same sample that was used for the Congo Red Retention assay or on a second sample from the same subject and these tests may be carried out after Congo Red Retention assay or at substantially the sane time. The assays using antibodies that detect specific conformations of misfolded protein aggregates may, in certain embodiments, be used to confirm the result obtained using the Congo Red Retention assay or may be used to obtain additional qualitative information, e.g., correlating the presence or absence of specific oligomeric protein conformations with the likelihood to develop PE or as an indication of the severity of PE. In addition to the assays that are based on protein aggregates found in PE samples (i.e., congophilia/Congo Red Retention and antibody-based protein aggregate analysis) additional test may be conducted to either confirm the results obtained in the previous assays or to obtain additional quantitative or qualitative data. For example, additional assays may be performed measuring the absence or presence and/or the relative amount of one or more biomarkers described herein, including assays to detect the PB biomarker albumin, SerpinA1, sFlt-1, PlGF, VEGF, using assays such as ELISA or e.g., analyzing protein fragments by SELDI-TOF, etc. Additionally, predictive ratios may be calculated for the biomarkers, such as e.g., sFlt/PlGF [uFP]. Further, the presence or absence and/or relative level of additional proteins may be used for diagnosis of PE, such as immunoglobulins, ceruloplasmin and insulin inducible protein 6-16 in protein aggregates of urine.

It should be appreciated that the tests and assays described herein may be carried out in any order and may be conducted alone or in any combination and the invention is not limited in this aspect. It has previously been shown by Applicant and described herein that any one of the tests and assays described is sufficient to detect PE and to aid diagnosis and prognosis.

8 Treatments

Protein conformational disorders such as Alzheimer's, light chain amyloidosis and prion diseases are propagated by amyloid fibril formation and aggregation due to defective folding of cellular proteins into aberrant 3D structures. It has recently been observed that soluble pre-amyloid oligomers (intermediates in fibril assembly) have proteotoxic effects leading to endothelial damage and oxidative stress. Applicants have previously shown that endothelial damage and oxidative stress play pathogenic roles in severe preeclampsia (sPE). Applicants have now unexpectedly found that PE is a conformational disorder associated with protein misfolding and aggregation, characterized by amyloid-like assembly of proteins. Applicants further established by antibody staining with conformation-specific polyclonal and/or monoclonal antibodies that the misfolded intermediates found in the urine of subjects with PB have a propensity to assemble into pore-like structures (amyloid channels) that may play a role in clinical disease manifestations, such as e.g., endothelial damage and oxidative stress. Applicants have reasoned that the accumulation of abnormal protein aggregates in the placenta of patients diagnosed with preeclampsia indicates that these protein aggregates vs a causative factor in the pathology of this disease. In certain embodiments, therapeutical interventions for preeclampsia, utilizing immunological or pharmacological strategies, are provided based on blocking the formation of misfolded protein oligomers that may assemble into amyloid channels. In certain embodiments, treatments for PE are provided. In certain embodiments, treatments are based on therapeutic regimens that were found to reduce severity of other misfolding disorders such as for example Alzheimer's disease. Research into novel therapeutic strategies for the treatment of similar diseases of abnormal protein aggregation, such as Alzheimer's disease and other amyloidoses, has identified agents that can inhibit the development of new protein aggregates and/or decrease the burden of pre-existing protein aggregates. The finding that PE is associated with abnormal protein aggregates presents avenues for treatment.

Multiple approaches and agents, e.g., small molecular weight inhibitors, peptidic inhibitors of fibril and/or oligomer formation, vaccination against one or more of the components of the protein aggregate, passive immunization with antibodies or antibody fragments against one or more of the components of the protein aggregate, among other approaches have been developed for the inhibition and/or reversal of beta-amyloid aggregation in the treatment of Alzheimer's disease. Some of these agents have been shown to inhibit the aggregation of proteins other than beta-amyloid. For example, p-Aminophenol and 2-Amino-4-Chlorophenol and derivatives (Cell Biochemistry and Biophysics 44: 549-553 (2006)) have been shown to inhibit aggregation as well.

In certain embodiments, methods of treating preeclampsia in patients using protein aggregation inhibitors to inhibit the de novo formation of protein aggregates and/or reverse the formation of preexisting aggregates are provided. In certain embodiments, agents that stabilize the native conformation of aggregate-prone proteins are provided that decrease the rate of abnormal folding and consequent aggregation. In certain embodiments, small molecular weight inhibitors, peptidic inhibitors of fibril and/or oligomer formation, vaccination against one or more of the components of the protein aggregate, passive immunization with antibodies or antibody fragments against one or more of the components of the protein aggregate are provided for the treatment and/or prevention of preeclampsia. In certain embodiments, anti-beta amyloid agents (e.g., those summarized in Drug Discovery Today: TherapeuticStrategies 1: 7-12 (2004) and references contained therein are provided for the treatment and/or prevention of preeclampsia.

Applicants have also found that SerpinA1 (alpha-1 antitrypsin) and/or peptide fragments of SerpinA1 is a component of the of the protein aggregates found in preeclampsia. It has previously been shown that SerpinA1 can serve as a biomarker for early detection of preeclampsia (U.S. application Ser. No. 12/084,004 (PCT/US2006/042585), incorporated herein by reference in their entirety).

As used herein the term "SerpinA1 polypeptide" refers to full-length SerpinA1 polypeptide and also to a polypeptide that is a fragment of full-length SerpinA1 polypeptide. SerpinA1 has been previously identified as a serine protease inhibitor, and is also known as alpha 1 antitrypsin. SerpinA1 polypeptide has Genbank Accession No. P01009. It will be understood that SerpinA1 polypeptides encoded by alternative alleles of SerpinA1 may also be used to detect the presence of preeclampsia in subjects. For example, SerpinA1 polypeptides encoded by M1A, M2, and/or M3 alleles of SerpinA1 may be used in methods of the invention to diagnose and/or assess preeclampsia in subjects. SerpinA1 polypeptides are synthesized in the liver and trophoblast and are present in multiple forms that are unrelated to SerpinA1's antiproteolytic activity. SerpinA1 polypeptide is highly susceptible to oxidation and intensive oxidative stress induces SerpinA1 oxidation. A polypeptide that is a fragment at the C-terminus of full-length SerpinA1 polypeptide induces oxidative burst and neutrophil chemotaxis in vitro.

The identification of SerpinA1 in urinary samples of subjects with PB indicates that preeclampsia has a similar disease etiology to other disorders such as alpha-1 antitrypsin deficiency which, due to the accumulation of misfolded alpha-1 antitrypsin leads to damage of hepatocytes and cirrhosis of the liver (N. Engl. J. Med. 346: 45-53 (2002); J. Clin. Inv. 110: 1585-1590 (2002)). In certain embodiments, therapeutic agents that prevent the formation of abnormal aggregates of SerpinA1 protein or its fragments are provided. In other embodiments, agents are provided that can dissociate existing SerpinA1 aggregates or its fragments. For example, on such agent is Trimethylamine N-oxide and related compounds (Am. J. Respir. Cell Mol. Biol. 24:727-732 (2001)). Another example is the FLEAIG peptide (SEQ ID NO: 7) and related peptides and derivatives (Am. J. Respir. Cell Mol. Biol. 35: 540-548 (2006)). In certain embodiments, Trimethylamine N-oxide and related compounds or FLEAIG peptide (SEQ ID NO: 7) and related peptides and derivatives are provided as useful therapeutic agents for the treatment and/or prevention of preeclampsia.

As will be appreciated by those of ordinary skill in the art, evaluation of a treatment also may be based upon an evaluation of the symptoms or clinical end-points of preeclampsia. Thus, methods of the invention are useful for determining the onset, progression or regression of a condition that is characterized by one or more of the biomarkers (such as e.g., SerpinA1, albumin, sFlt-1, PlGF, VEGF, misfolded protein aggregates/congophilia) described herein in a pregnant subject. In some instances, methods of the invention can be used to detect levels of one or more of the biomarkers described herein in subjects diagnosed as having preeclampsia. In other instances, methods of the invention can be used to obtain measurements that represent the diagnosis of preeclampsia in a subject. In some instances, a subject may be already be undergoing drug therapy for preeclampsia, while in other instances a subject may be without present preeclampsia therapy.

The type of treatment for preeclampsia selected may be based, in part, upon selecting pregnant women who have abnormally high levels of one or more of the biomarkers described herein (such as SerpinA1, albumin, sFlt-1, PlGF, VEGF) and/or are shown to have misfolded protein aggregates associated with preeclampsia and exhibit congophilia. Treatments may include administration of a particular type of drug, an activity change, or a dietary change, which may be based at least in part on the presence or absence of an indication of preeclampsia (e.g., detection of one or more of the biomarkers, congophilia/misfolded protein aggregates and/or specific protein oligomer conformations, described herein). Such subjects may already be receiving a drug for treating preeclampsia. It may be appropriate according to the invention to alter a therapeutic regimen for a subject, based upon the measurement of the level of one or more of the biomarker, congophilia/misfolded protein aggregates and/or specific protein oligomer conformations described herein using a method set forth herein. This can be understood in connection with treatment of preeclampsia. A subject may be free of any present treatment for preeclampsia and monitoring of one or more of the biomarkers, congophilia/misfolded protein aggregates and/or specific protein oligomer conformations described herein may allow selection of the most efficacious treatment regimen.

9. Kits

In some embodiments, the instant invention provides kits useful in the methods of the invention. Reagents may be labeled compounds or agents capable of detecting congophilia or misfolded protein aggregates in a urine sample. In certain embodiments, the kits may comprise a surface that has affinity to proteins that can be contacted with the sample (e.g., a urine sample). The kit may further comprise a dye (e.g., Congo Red) that associates with misfolded protein aggregates associated with preeclampsia and can be contacted with the sample. The kit may also comprise a vessel, tube or container suitable for mixing the sample with the dye, or incubating the surface that has affinity to proteins comprising the bound proteins of the sample. The kit may contain one or more washing solutions suitable to remove unincorporated dye. The kit may further comprise positive and negative controls to allow for control of sufficient incorporation and/or washing, e.g., provided on a "test strip" comprising the surface that has affinity to proteins.

In some embodiments, the instant invention provides kits useful in the methods of the invention. Reagents may be labeled compounds or agents capable of detecting, in a urine sample, the presence of misfolded protein aggregates and means for determining the amount of the polypeptide (e.g., an antibody that binds the polypeptide). Suitable reagents for binding with a polypeptide corresponding to a biomarker useful in a method of the subject invention include antibodies, antibody derivatives, antibody fragments, and the like. For antibody-based kits, the kit can comprise, for example: (1) a first antibody (e.g., attached to a solid support) which binds to a polypeptide corresponding to a biomarker of the invention; and, optionally, (2) a second, different antibody that binds to either the polypeptide or the first antibody and is conjugated to a detectable label.

Suitable PB-biomarkers that may be detected using such kits include sFlt-1, PLOP, VEGF, albumin, SerpinA1, IFI6 and ceruloplasmin. In certain embodiments, kits comprise antibodies specific for certain conformations of misfolded proteins, e.g., fibrillar conformations and the like. The antibody may bind to specific protein aggregate conformations from the sample tested/analyzed by the kit. In certain embodiments, wherein the sample is a urinary sample comprising PP-associated protein aggregates which comprise immunoglobulins, the secondary antibody is preabsorbed with Ig to reduce or prevent non-specific binding of the secondary antibody to the protein aggregate comprising immunoglobulins.

The kits, in certain embodiments, can also comprise other components, such as a buffering agent, a preservative, or a protein stabilizing agent. The kit can further comprise components necessary for detecting the detectable label (e.g., an enzyme or a substrate).

Each component of the kit can be enclosed within an individual container and all of the various containers can be within a single package, along with instructions for interpreting the results of the assays performed using the kit. The container may be pretreated with a stabilizing agent and/or a stabilizing agent may be a component of the kit.

EXAMPLES

Example 1

Methods
Protocol Congo Red Dot Blotting of Urine Samples (Red Dot Test):
1. Centrifuge obtained urine samples at 1500×g, 15 minutes and 4° C.
2. Measure urine protein in the spun urine using the Pierce BCA kit (Thermo Scientific Cat #23225). Urine samples may require a 12-fold dilution for protein measurement. Urine samples from women that are potentially preeclampsic have wide variations in protein concentration. Protein levels in urine also vary widely in healthy people depending on the state of hydration. For this mason it is preferred to equalize the total protein concentration. Out of over 680 urine samples obtained from women only approximately 5% (371/681) of urine samples measured <2 mg/mL total protein. Approximately 60% of urine samples had over 6.6 mg/mL total protein. Generally, in most of the cases there is no need to dry the samples, e.g. in the SpeedVac. The drying method was validated and it was found that sample drying does not change the Red Dot Test result. For consistency, SpeedVac drying was used for all assays.

3. Add the volume of sample that contains 200 µg protein to a conical centrifuge tube and concentrate to dryness using, e.g., a SpeedVac.

4. Prepare the Congo Red stock solution (5 mg/ml-) Congo red (Sigma, Cat #C6277) in water. Centrifuge at 14,000×g, 10 minutes to spin down undissolved powder. The stock solution should be freshly made, and should be used (i.e. added to the urine samples) within approximately 1 hour of preparation. One may choose to prepare a Congo Red working solution (0.1 mg/ml) by diluting 50-fold the stock solution.

5. Make Blank sample by adding 2 µl Congo red stock to 0.1 mL PBS (phosphate buffer).

6. Remove dried urine samples from SpeedVac and add 30 µL of Congo Red working solution and vortex well.

7. Incubate 1 hour with vigorous shaking (on a vortex) to achieve Congo red binding.

8. After 1 hour, apply duplicate dots of 5 µl sample with Congo red on nitrocellulose membrane (0.2 micron mesh) in duplicate. Each dot should preferably contain 33.3 µg protein. Also apply the Blank sample in duplicate. If more than one sheet is necessary each sheet should contain dots from the Blank sample. Preferably a positive control sample is incorporated in each run. One may choose to make an application grid which can be placed on a transilluminator and on top of it the nitrocellulose membrane can be placed so that the dots can be spaced in an orderly fashion and so that it is possible to track exactly where each sample has been placed.

9. Let membrane dry for 15 minutes.

10. Wash in water for 3 minutes.

11. Photograph (all spots should look similar in staining intensity at this point).

12. Wash in 50% methanol for 3 minutes then in 70% methanol for 1 minutes and then in 90% methanol until the red in the Blank sample disappears (generally 7-10 minutes).

13. Photograph (spot intensity, e.g. positive control sample Blank sample) should look different).

14. Scan the images and calculate the optical density (OD) of each dot before and after the methanol wash using any densitometry software, e.g. NIH Image J.

15. Calculate the % Congo Red Incorporation (CRI) for all samples as (Average OD of spots from same sample before methanol wash/Average OD of Blank from the same nitrocellulose sheet)×100.

16. Calculate the % Congo Red Retention (CRR) for all samples including the Blank as (Average OD of spots from same sample after methanol wash/Average of spots from same sample before methanol)×100; then subtract CRR of the Blank sample from all values of the dots from urine samples. If the methanol washing was complete there should not be any residual red visible in the dots from the Blank and their OD average should be 0.

17. Call samples with CRR>20% Red Dot Test positive and those CRR<15% Red Dot Test negative.

18. Repeat test if CRR is between 15-20%. It has been found that the diagnostic and prognostic cut-off of the 223 samples analyzed by us using the Red Dot Test is approximately 16.1%.

It should be appreciated that all incubation and preparation (e.g., centrifugation) times, volumes and concentrations are the preferred times, volumes and concentrations. However, other incubation and preparation times, volumes and concentrations may also lead to reliable test results and can be established by one of skill in the art without undue experimentation, and the incubation and preparation times, volumes and concentrations described here are non-limiting. Further, it should be appreciated that the chemicals and equipment described herein are non-limiting and other equivalent chemicals and/or equipment may be used. Further, it should be appreciated that some steps and the order of the steps described herein may be optional and some steps and the order of the steps may be changed, omitted, or combined. Such changes and modifications would be apparent to one of ordinary skill. For example, incubation times of less than 1 hour (step #7), adding a non-denaturing detergent (e.g. Tween 20) to the urine sample, or substituting methanol with ethanol or isopropanol in the washing steps will also result in a reliable test.

Study Design:

110 women were enrolled prospectively in 3 groups: normotensive controls (CRL n=49, GA: 28 [21-34] weeks); chronic hypertension (cHTN n=12, GA: 29 [24-34] weeks) and severe PE (sPE n=49, GA 30 [24-34] weeks). In addition, 34 asymptomatic pregnant women at high-risk of PB were followed longitudinally. Urine congophilia was quantified by dot blot fixation and spectral shift assays on equal amounts of protein. Congophilic proteins were identified by tandem mass spectrometry and validated by Western blot. A urinary proteomic fingerprint was generated using SELDI-TOF. Placental congophilia was examined by polarized microscopy.

Results

Figure 2:
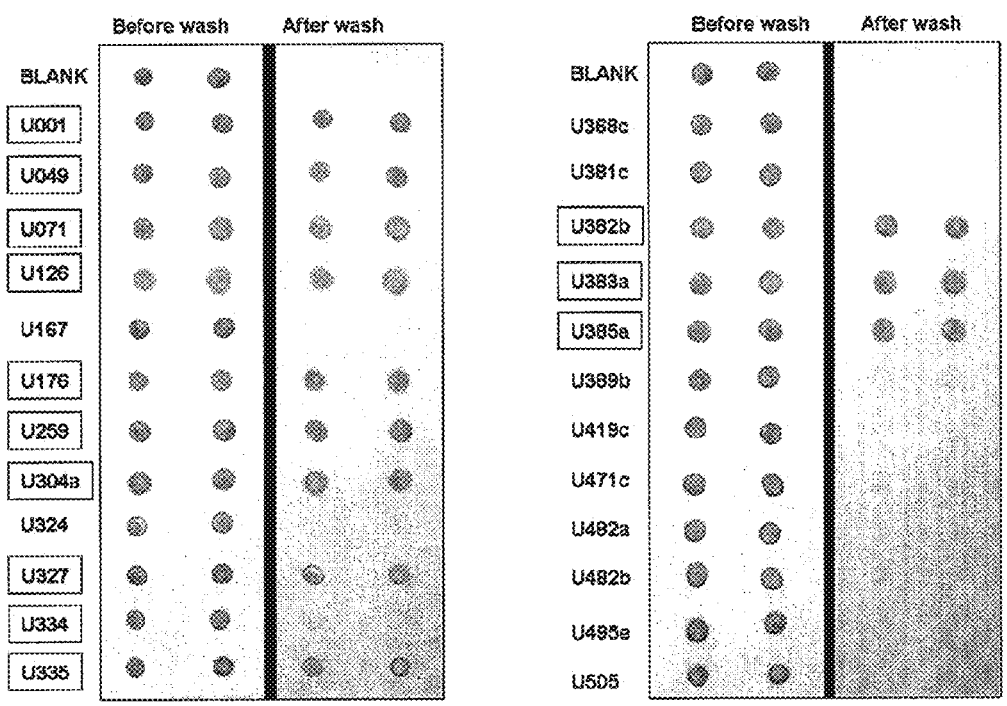
FIG. 2 shows a photograph of a nitrocellulose membrane before and after wash following Congo Red Dot Test of urine samples (33 µg/spot were applied to nitrocellulose) of a cross-sectional cohort. Samples with boxed number were from women with manifest severe preeclampsia.
Figure 3:
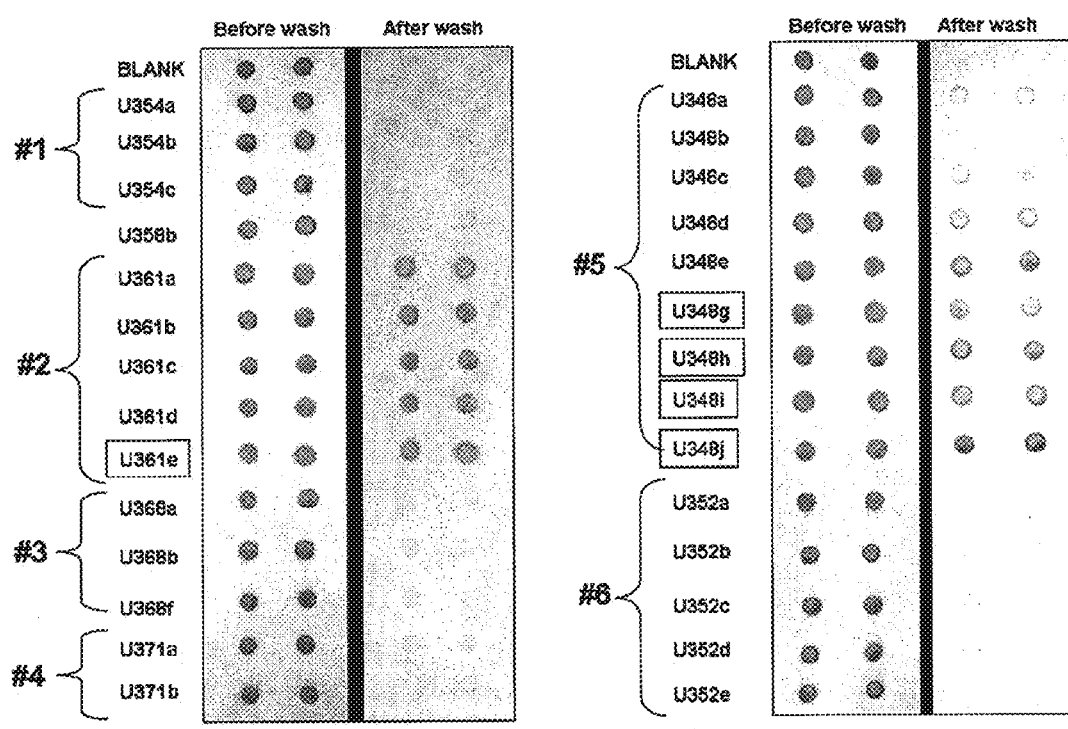
FIG. 3 shows a photograph of a nitrocellulose membrane before and after wash following Congo Red Dot Test of urine samples (33 µg/spot were applied to nitrocellulose) of a longitudinal cohort Six pregnant women were followed with repeat analysis of urine throughout pregnancy. The boxed samples were from the time of clinically manifest disease. The boxes corresponding to samples U348i and U348j were postpartum after medically indicated delivered for preeclampsia (emergency C-section).
Figure 4:
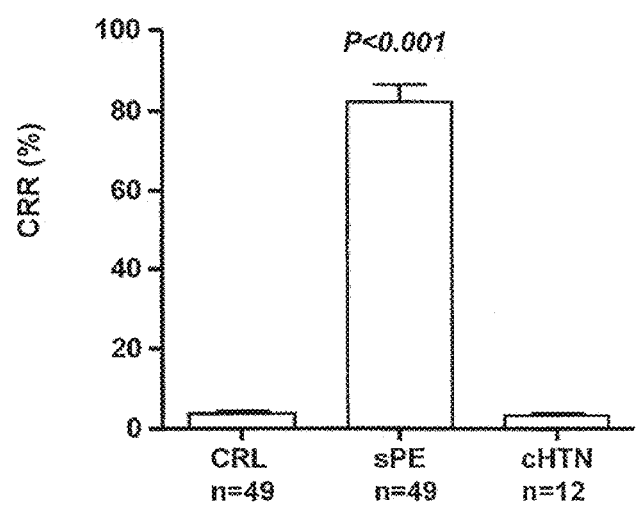
FIG. 4 shows a bar graph of Congo Red Retention (CRR) normalized for amount of protein in women with severe preeclampsia (sPE), chronic hypertention (cHTN) and normal pregnant controls (CRL).
Figure 5:
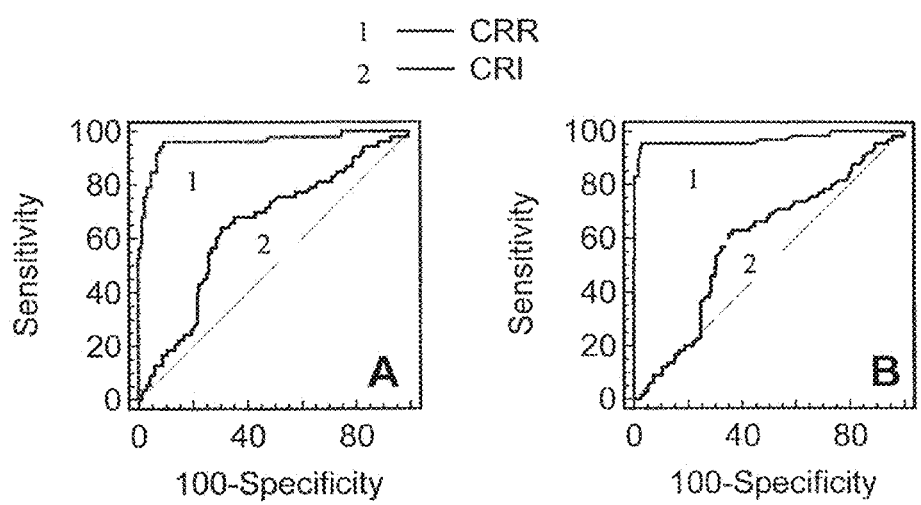
FIG. 5 shows ROC curves of Congo Red Retention (CRR) and Congo Red incorporation (CRI) coefficients to (A) diagnose, and (B) predict a mandated delivery for preeclampsia (223 urine samples from 114 different pregnant women).
Figure 6:
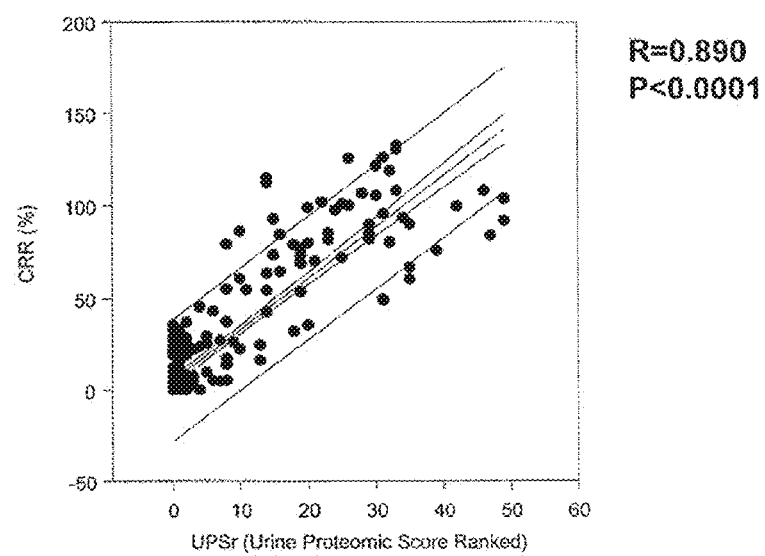
FIG. 6 shows a diagram correlating Congo Red Retention (CRR) of urine proteins with the presence and severity of preeclampsia as determined by the abnormal proteomic profile (UPSr).
Figure 14:
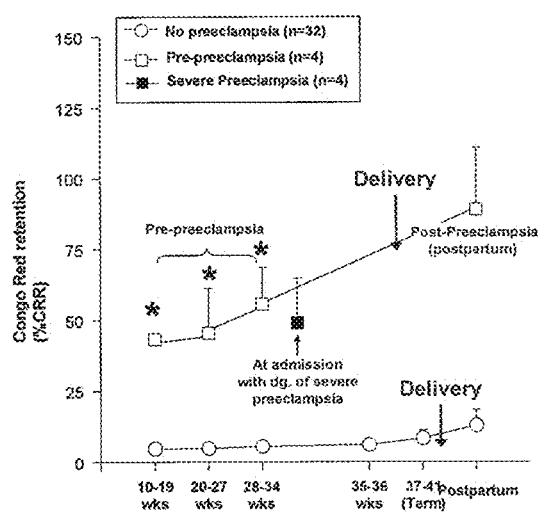
FIG. 14 shows a graph for the prediction of indicated delivery for preeclampsia in a longitudinal cohort.

FIG. 1 shows a photograph of a nitrocellulose membrane before (left) and after wash (right) following Congo Red Dot Test of urine samples (5 µL/spot were applied to nitrocellulose). As can be seen from the Figure, Congo Red stains the samples similarly well before the wash, but is specific for urine samples obtained from women with severe preeclampsia (sPE) after the wash (with the blank being negative). FIG. 2 shows a photograph of a nitrocellulose membrane before and after wash following Congo Red Dot Test of urine samples (33 µg/spot were applied to nitrocellulose) of a cross-sectional cohort (24 samples). Samples with boxed number were from women with manifest severe preeclampsia (sPE). As can be seen from the Figure, Congo Red stains the samples similarly well before the wash, but is specific for urine samples obtained from women with severe preeclampsia after the wash. FIG. 3 shows a photograph of a nitrocellulose membrane before and after wash following Congo Red Dot Test of urine samples (33 µg/spot were applied to nitrocellulose) of a longitudinal cohort (28 samples). Six pregnant women were followed with repeat analysis of urine throughout pregnancy. Patients #2 and #5 developed preeclampsia. The boxed samples obtained from patient #5 were from the time of clinically manifest disease. The boxes corresponding to samples U348i and U348j for patient #5 were postpartum after medically indicated delivered for preeclampsia (emergency C-section). As shown here, both patients (#2 and #5) had abnormal Congo red urine test (red dot positive) long before they were diagnosed and admitted for preeclampsia. FIG. 14 shows a graph for the prediction of indicated delivery for preeclampsia in a longitudinal cohort. 36 women at high-risk (n=30) and low-risk (n=6) were studied using the Congo Red Test. Four women in this cohort developed severe preeclampsia and had an indicated preterm delivery. The data shows that women that later developed PE had high urine congophilia in the first sample that was tested. It was not possible to obtain earlier sample to test if these women had a positive test also before pregnancy. FIG. 4 shows a bar graph of Congo Red Retention (CRR) normalized for amount of protein as described in women with severe preeclampsia (sPE), chronic hypertension (cHTN) and normal pregnant controls (CRL). As shown, CRR is clearly associated with and indicative of severe preeclampsia (sPE). The urine was tested at the time of admission with diagnosis of severe preeclampsia. FIG. 5 shows ROC caves of Congo Red Retention (CRR) and Congo Red incorporation (CRI) coefficients to (A) diagnose, and (B) predict a mandated delivery for preeclampsia (223 urine samples from 114 different pregnant women). Some women had sequential urine samples analyzed throughout pregnancy. FIG. 6 shows that Congo Red Retention (CRR) of urine proteins is significantly correlated with the presence and severity of preeclampsia as determined by the abnormal proteomic profile (UPSr).

Figure 7:
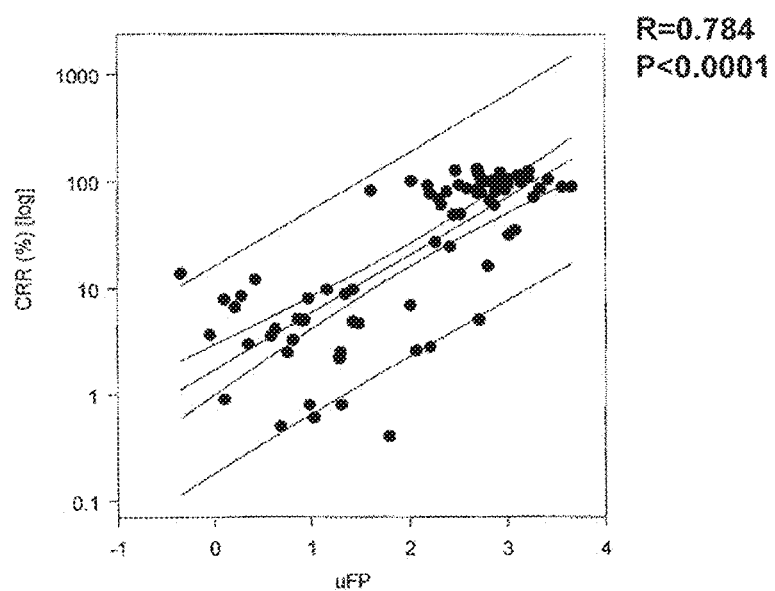
FIG. 7 shows a diagram correlating Congo Red Retention (CRR) of urine proteins with the ratio indicator uFP: log [sFlt-1/PlGF×100].
Figure 8:
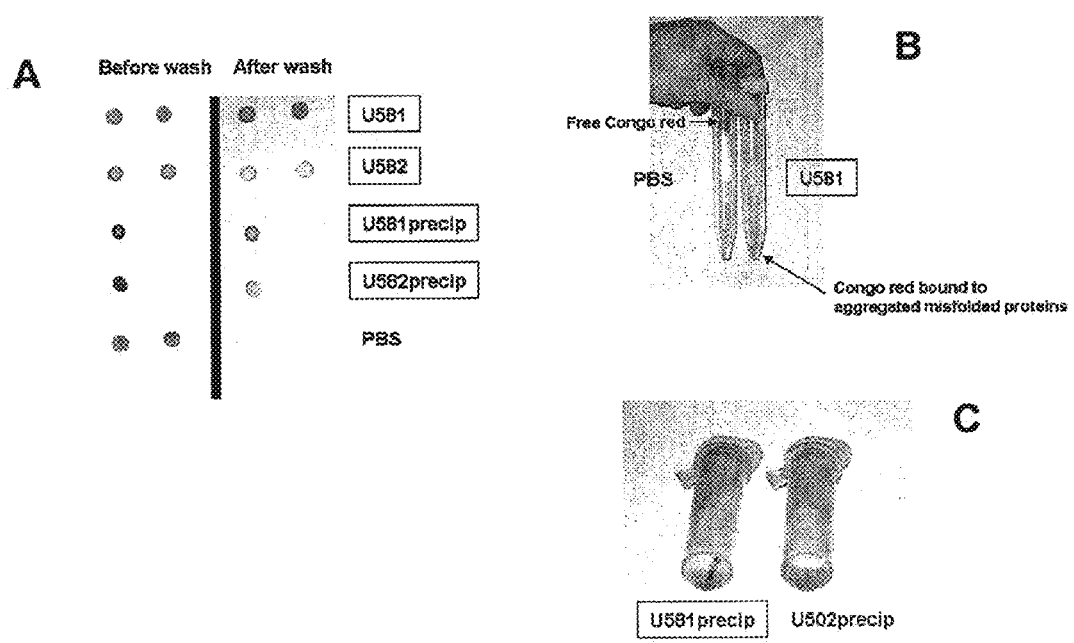
FIG. 8 shows methods of separation of misfolded urine proteins in preeclampsia by (A) Congo red affinity by dot blot, (B) gel filtration, or (C) centrifugation. Boxed samples are from women with clinically manifest severe preeclampsia (sPE).

FIG. 7 shows that Congo Red Retention (CRR) of urine proteins is significantly correlated with the ratio indicator uFP: log [sFlt-1/PIGF×100], as described herein and also in (U.S. Publ. No: US-2006-0183175; PCT/US2005/047010). FIG. 8 shows that similar with misfolded proteins of other diseases and indications (e.g., Alzheimer's and prion disease), misfolded urine proteins in preeclampsia can be separated by methods such as (A) Congo red affinity by dot blot (boxed samples are from women with clinically manifest severe preeclampsia (sPE)) as described herein, (B) gel filtration, or (C) centrifugation and washing of the precipitated Congo red bound proteins with water (e.g. for (B) and (C)).

In further experiments, placental sections were stained with Congo red and showed cloud-like birefringent material deposited in PE but not CRL syncytiotrophoblasts. FIG. A shows placental sections from three women, two with preterm delivery for severe preeclampsia (A-F) and another with idiopathic preterm birth (Control, G-H) that were stained with Congo Red and examined microscopically in either white light (A, D, G) or polarized light (B, C, E, F, H and I). Panels C and F are higher magnifications (640×) of the squared areas in Panels B & B, respectively. As seen in B and E, the placenta of the preeclamptic woman shows cloud-like grey-blue (B & C) or grey-g (E & F) birefringent material deposited in the syncytiotrophoblast layer (red arrows). Panel 1: polarized light image of a brain section from a patient with Alzheimer's disease that has been stained with Congo Red in the same conditions.

Figure 15A:
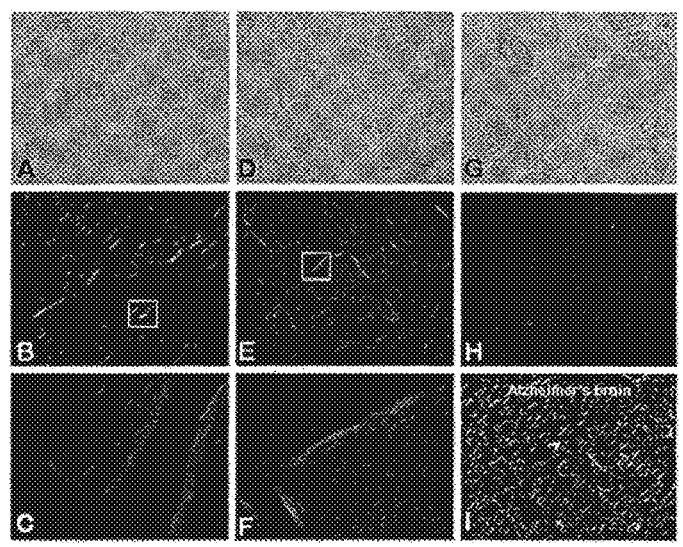
FIG. 15A shows placental sections from three women, two with preterm delivery for severe preeclampsia (A-F) and another with idiopathic preterm birth (Control, G-H) stained with Congo Red and examined microscopically in either white light (A, D, G) or polarized light (B, C, B, F, H and I). Panels C and F are higher magnifications (640×) of the squared areas in Panels B & E, respectively Panel I: polarized light image of a brain section from a patient with Alzheimer's disease that has been stained with Congo Red in the same conditions.
Figure 15B:
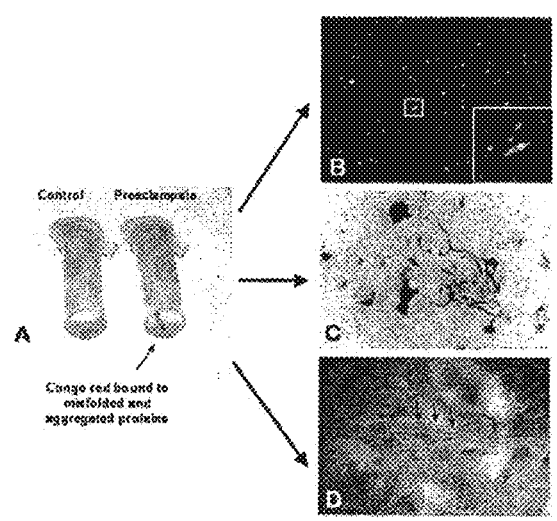
FIG. 15B shows imaging of Congo Red positive precipitated material in preeclamptic nine.

FIG. 15 B shows imaging of Congo Red positive precipitated material in preeclamptic urine. After Congo Red binding and centrifugation the precipitated material (A) is washed with water 3 times (repeating the centrifugation between the washes), resuspended in a drop of water and either placed on a microscope slide for imaging in polarized light (B) or on a grid for electron microscopy after staining positively (C) or negatively (D) with 1% uranyl acetate. The arrows point to a non-cellular structure, likely a fibril.

Figure 16:
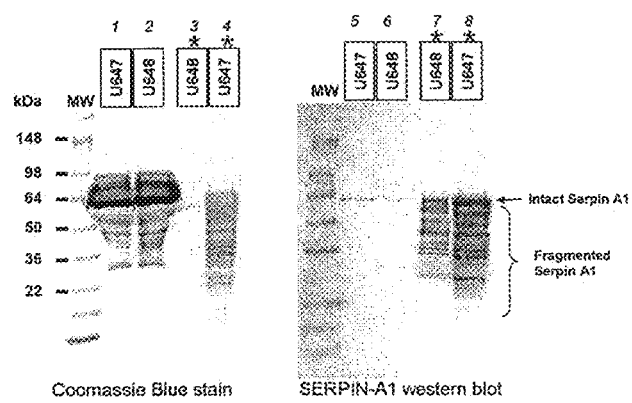
FIG. 16 shows urine samples from two women with severe preeclampsia on duplicate reducing SDS PAGE gels. The left panel shows the gel after staining of total proteins with Coomassie blue stain (Lanes 1-4). The right panel shows the immunoreactivity for SerpinA1 of proteins transferred to nitrocellulose. Molecular weight markers (MW) are shown on each panel.
Figure 17:
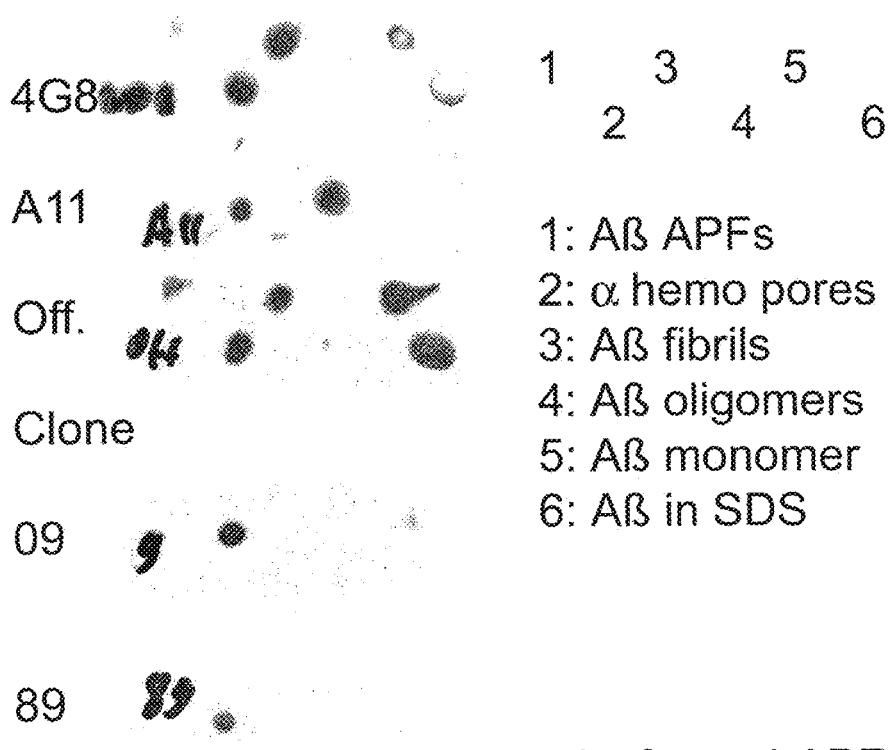
FIG. 17 shows secondary screening results for anti-APF monoclonals 09 and 89.
Figure 18:
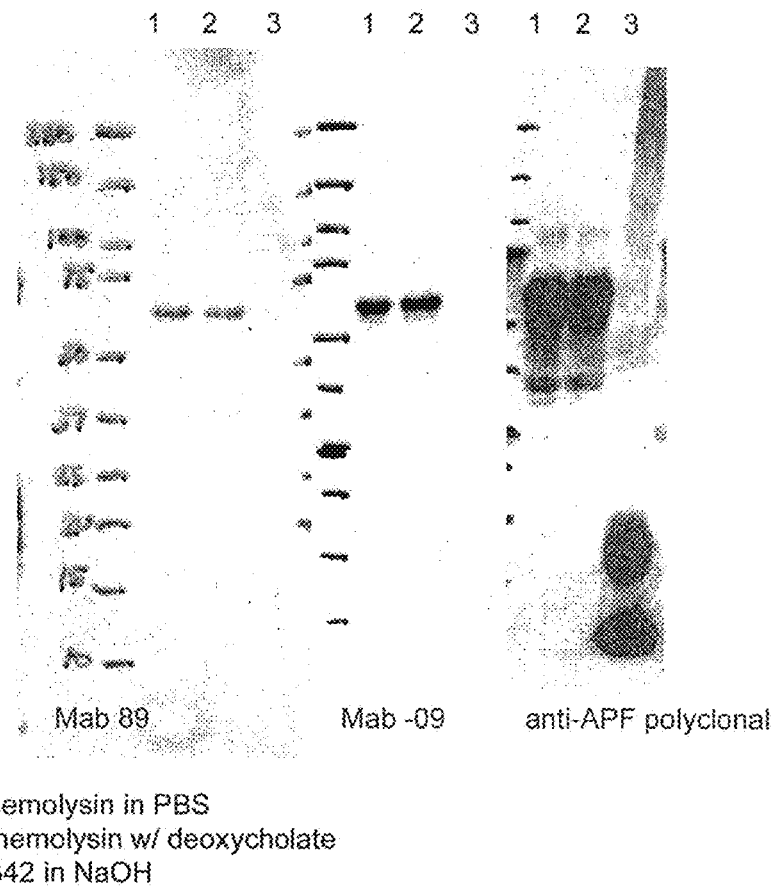
FIG. 18 shows results of characterization of monoclonals 09 and 89 against alpha hemolysin and ABeta.

In further experiments, Congophilic material as well as the bands immunoreactive for conformational antibodies were run on SDS PAGE and subjected to mass spectrometry. Fragments of antitrypsin, ceruloplasmin, heavy- and light-chain IgG were identified in congophilic proteinuria of PB and in the bands immunoreactive for conformational antibodies. Western blot for SERPINA1 in congophilic material was performed and many fragments in a ladder pattern that reacted with the antibody were observed. The presence of ceruloplasmin and IFI6-16 in PB urine was confirmed by western blot and/or dot blot. Light chains were confirmed by ELISA. FIG. 16 shows urine samples from two women with severe preeclampsia (U647 and U648) that were loaded on duplicate 4-20% reducing SDS PAGE gels without (lanes 1-2 and 5-6) or with enrichment of misfolded proteins by Congo Red affinity precipitation (lanes 3-4 and 7-8, red asterisk). The left panel shows the gel after staining of total proteins with Coomassie blue stain (Lanes 1-4). Many new bands became visible in the samples precipitated with Congo Red. The right panel shows the immunoreactivity for SerpinA1 of proteins transferred to nitrocellulose. The additional fragmentation (ladder) pattern is visible in lanes 7 & 8 but not in 5 and 6. Molecular weight markers (MW) are shown on each panel.

This also implies that Congo Red can be efficiently used to enrich biological samples (in this case preeclamptic urine) in misfolded and aggregated proteins which can be further studied.

In summary, the data show that PE is characterized by a marked increase in urine congophilic proteins compared to CRL and cHTN, independent of GA ($P<0.001$). In women followed longitudinally who developed sPE requiring early delivery (n=4), congophilic urine proteins appeared 8-10 weeks prior to clinical manifestations. Congo red binding to PE urine proteins resulted in a red-shift in absorbance similarly seen for other amyloid supramolecular protein structures. Urinary congophilia correlated with the proteomic profile characteristic of PE ($r=0.89$, $P<0.001$).

The data provide evidence that PE is a pregnancy-specific disease characterized by supramolecular amyloid-like assembly of proteins and congophilic proteinuria. Detection of urine congophilia by dot blot fixation and/or spectral shift assays are indicative of a patient with preeclampsia and provide a method for diagnosis of preeclampsia. Urinary congophilic protein aggregates, detected as described, are not only diagnostic of an existing preeclampsia, but are also predictive of the future development of preeclampsia (clinical outcome). In addition to detecting the presence of congophilic protein aggregates in the urine, placental tissue samples stained with Congo Red display characteristic features of such protein aggregates. This methodology of detecting Congo Red staining in the placenta also has application in the diagnosis of preeclampsia.

It should be appreciated that in addition to Congo Red the presence of protein aggregates may also be detected by a variety of other agents and methodologies (e.g., Thioflavin S, amongst others) that are known in the art.

Example 2

Methods
Study Design:
347 pregnant women were enrolled prospectively in the following groups: normotensive controls (CRL n=98, GA:27[7-42 weeks]); chronic hypertension (cHTN n=40, GA:32[11-41 weeks]), gestational hypertension (gHTN n=8 GA:37[26-39 weeks]), mild PE (mPE n=36, GA:36 [24-41 weeks]), severe PE (sPE n=117, GA:32(22-42 weeks)), superimposed PE (spPE n=33 GA:33[18-40 weeks]). 35 asymptomatic women were tested serially throughout gestation. A "Congo Red (CR) Dot" test was standardized with equal urine protein and objectively quantified within minutes as % Congo Red retention (CRR). CRR was evaluated for its ability to predict an indicated delivery for PE (IND) compared to protein-to-creatinine ratio (P/C) and the previously validated urine sFlt1/PlGF ratio, as described herein and also in (U.S. Publ. No: US-2006-0183175; PCT/US2005/047010).

Figure 9:
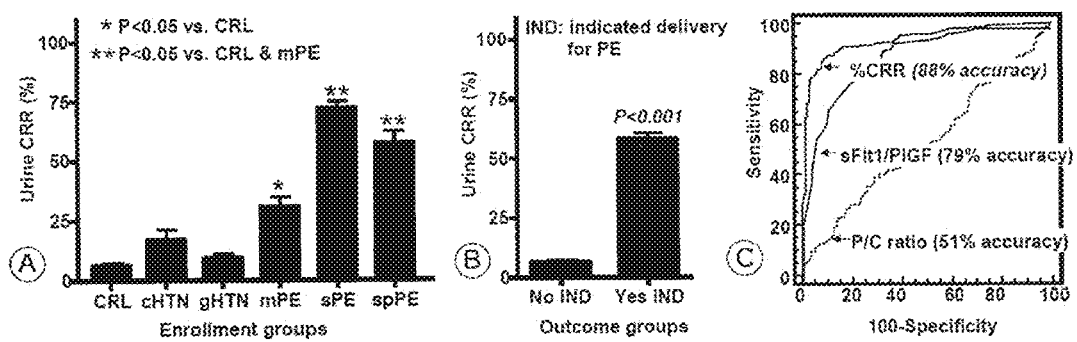
FIG. 9 shows diagrams showing (A) % Congo Red Retention (CRR) of urine proteins of different treatment groups (CRL: control; cHTN: chronic hypertension; gHTN: gestational hypertension; mPE: mild preeclampsia; sPE: severe preeclampsia; spPE: superimposed preeclampsia); (B) % Congo Red Retention (CRR) of urine proteins for different outcome groups (IND: indicated delivery for PE); (C) accuracy graphs comparing the accuracy of prediction (sensitivity/100-specificity) of (1) % Congo Red Retention (CRR) of urine proteins, (2) urine ratio of sFLT/PlGF and (3) P/C ratio urine protein/creatine ratio.

Results:

PE is characterized by increased excretion of misfolded proteins with affinity for the azo dye Congo Red (CR), also used to detect aberrant amyloidal aggregates in Alzheimer's and prion disease. A "Congo Red (CR) Dot" test CRR was designed and validated as a diagnostic and prognostic test for PB based on urine congophilia as a measure of global protein misfolding load in pregnancy. FIG. 9A shows % Congo Red Retention (CRR) of urine proteins of different treatment groups (CRL: control; cHTN: chronic hypertension; gHTN: gestational hypertension; mPE: mild preeclampsia; sPE: severe preeclampsia; spPE: superimposed preeclampsia). 61% (211/347) of women had IND: CRL: 4%; crHTN: 40%; gHTN: 75%; mPE: 69%; sPE: 99%; spPE: 100%. 77% (162/211) of INDs occurred preterm and 51% (107/211)<34 weeks GA. CRR was elevated in mPE and further increased in sPE and spPE independent of GA. Women requiring IND had elevated CRR at enrollment (FIG. 9B, P<0.001). FIG. 9C shows that among women followed longitudinally, 11% (4/35) had preterm IND. In this group, CRRs was increased 14±4 weeks prior to clinically manifest PE. CRR had higher accuracy in predicting IND compared to urine ratio of sFlt1/PlGF (P=0.014) and urine protein/creatine ratio (P/C) (P<0.001) (FIG. 9 C).

In summary, assessment of global protein misfolding load by CRR is a simple diagnostic test for PE and for prediction of IND, an important contributor to preterm birth.

Example 3

Methods
Study Design:

111 urine samples from women enrolled in 3 groups: sPE (n=49, GA. 28±1 weeks), chronic hypertension (cHTN n=12, GA: 29±1 weeks) and normotensive controls (CRL n=50, GA: 28±1 weeks) were analyzed. Equal amounts of mine protein was subjected to dot blot using 3 conformation-specific antibodies recognizing prefibrillar soluble oligomers (A11, Invitrogen), ring-shaped protofibrils (Officer) or fibrils (OC). Specificity was confirmed by omitting the primary antibodies. Identity of aggregated component proteins was sought by mass spectrometry and validated by Western blot with sequence-specific antibodies.

Results

Protein conformational disorders such as Alzheimer's, light chain amyloidosis and prion diseases are propagated by amyloid fibril formation and aggregation due to defective folding of cellular proteins into aberrant 3D structures. Soluble pre-amyloid oligomers (intermediates in fibril assembly) have proteotoxic effects leading to endothelial damage and oxidative stress.

Some important features in the pathogenesis of preeclampsia ware vascular endothelial activation followed by vasospasm. Theories of its cause include abnormal implantation and development of the placenta, oxidative stress, impaired endothelial prostanoid and nitric oxide homeostasis, genetic polymorphisms, abnormal circulating autoantibodies and an abnormal maternal systematic inflammatory response (Buhimschi I A et al. Hum Reprod Update 1998; 4:25-42; Ward K et al; Nat Genet 1993; 4:59; Wallukat G et al. J Clin Invest 1999; 103:945-952; Fass M M et al. Am J Obstet Gynecol 1994; 171: 158-64; Roberta J M et al. Lancet 1993; 341: 1447-51). As endothelial damage and oxidative stress play pathogenic roles in severe preeclampsia (sPE) the nature of urinary soluble pre-amyloid oligomers associated with PE was identified and characterized.

Antibodies that were used to detect urinary soluble pre-amyloid oligomers included those that detect proteins in (i) a prefibrillar soluble oligomer conformation, such as the "A11" antibody amongst others, (ii) a ring-shaped protofibril conformation, such as the "Officer" antibody amongst others, and (iii) a fibril conformation, such as the "OC" antibody amongst others.

The urine dot blots comprising urinary protein aggregates presented a problem of nonspecific binding of the A11 antibody. It was later established (by mass spectrometry of the urinary protein samples) that the urinary protein aggregates of the samples also comprise misfolded human immunoglobulin (IgG) heavy- and light chains that were recognized non-specifically by (i.e., cross-reacted with) most of the secondary antibodies used. It was challenging to find a procedure which minimized this cross-reactivity. After screening numerous secondary antibodies for specificity it was found that it was critical for specificity to use secondary antibodies that were preabsorbed with human IgG.

Figure 10:
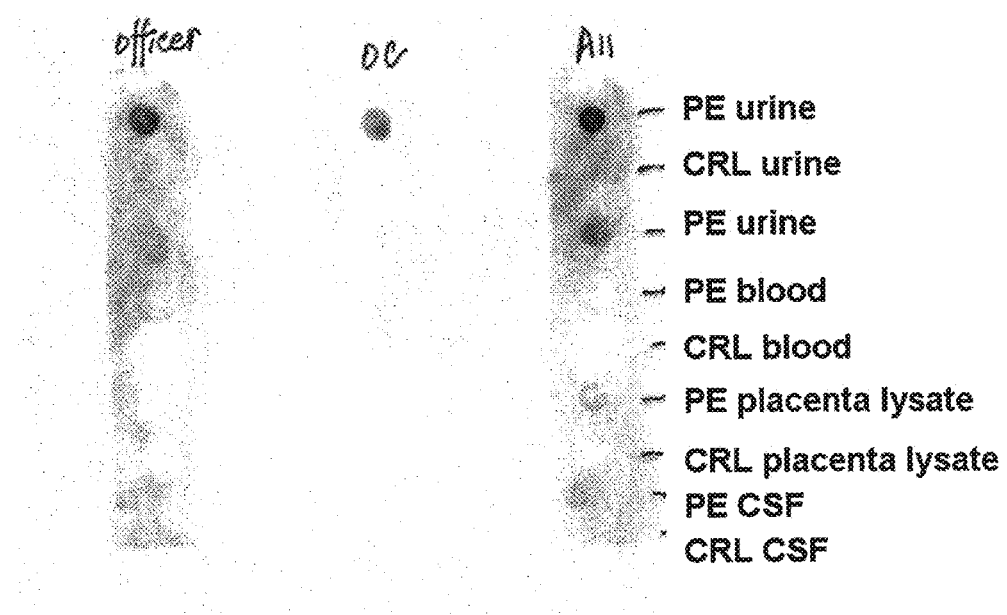
FIG. 10 shows a photograph of a western blot of a nitrocellulose membrane with spotted urine samples (as indicated urine, blood, cerebrospinal fluid (CSF) and placenta lysates; PE: preeclampsia; CRL: control) probed with three polyclonal antibodies A11, OC, and Officer.

The sensitivity of assays using the A11 polyclonal antibody to detect urinary protein aggregates was markedly improved if the secondary antibody was preabsorbed with human IgG to reduce non-specific binding of the secondary antibody to the urinary protein aggregates comprising misfolded human immunoglobulin (IgG) heavy and light chains. Using this assay methodology, positivity in the A11 assay correlated with severity of the symptoms. FIG. 10 shows a photograph of a western blot of a nitrocellulose membrane with spotted urine samples probed with three polyclonal antibodies A11, OC, and Officer. The 3 polyclonal antibodies (A11, specific for a wide range of conformations), OC (specific for fibrils) and Officer (specific for some annular conformations) showed immunoreactivity to samples from preeclampsia patients (as indicated: urine, blood, cerebrospinal fluid (CSF) and placenta lysates, PE: preeclampsia; CRL: control). The Officer antibody is thought to be specific for protein conformations that might form channels or pores in RBC analogous with amyloid channels and may explain hemolysis in patients with preeclampsia. Urine, blood, cerebrospinal fluid and placenta lysates were also tested. The data show that PE is a conformational disorder characterized by amyloid-like assembly of proteins. Concurrent A11 and Officer staining suggests that the misfolded intermediates have a propensity to assemble into pore-like structures (amyloid channels) that may play a role in clinical disease manifestations.

Figure 11:
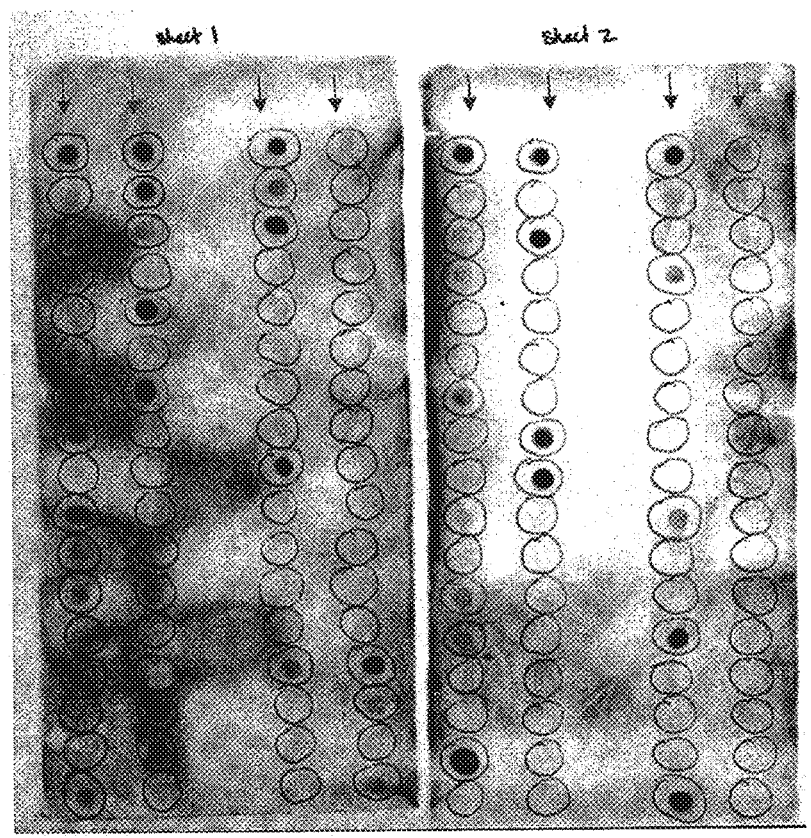
FIG. 11 shows a photograph of a western blot of a nitrocellulose membrane with spotted urine samples (PE: preeclampsia; CRL: control; cHTN: chronic hypertension) probed with polyclonal antibody A11. Red arrows mark rows where samples are spotted. The film is compared with the sample application grid and the position of each sample circled in black.

FIG. 11 shows representative dot blots of urine samples from women in the 3 categories: preeclampsia (PE), cHTN and CRL. Each spot contained 40 mgs urine protein. Red arrows mark rows where samples are spotted. The film is compared with the sample application grid and the position of each sample circled in black. It was found that many women with preeclampsia and Congo red positive test show A11 immunoreactivity in urine samples, although not all Congo red positive women have A11 positivity. The data indicate that A11 positivity correlates with symptom severity.

Women with sPE had increased A11 and Officer (sPE: 42±8 vs. cHTN: 9±6 vs. CRL: 3±1 U/µg, P<0.001) but not OC urine immunoreactivity, independent of GA. Urine A11 and Officer dot blot staining intensity correlated with severity of hypertension (P=0.007) and proteinuria (P=0.005).

In further experiments, it was tested which proteins are involved in forming the aggregates recognized by A11 in PE urine. Two high molecular weight bands which were also A11 positive in non-reducing SDS PAGE were cut out. A tryptic digests was performed and the sample was submitted to the Keck facility for protein identification of the soluble oligomer in sPE urine. The following identities were confirmed by mass spectrometry: immunoglobulin heavy and light chains, ceruloplasmin and interferon inducible protein 6-16 protein (GIP3, IFI6-16), which was found to interact with Alzheimer's presenilin-2 protein to regulate apoptosis. The presence of IFI6-16 in dot blots of preeclamptic urine was confirmed using an anti IFI6-16 antibody. The antibody was a mouse polyclonal from Novus Biologicals Inc, Littleton, Colo. Catalog #H00002537-A01.

The finding that proteins in the urine from preeclampsia patients, that were immunoreactive with the A11 antibody, include immunoglobulin heavy and light chains, ceruloplasmin and the interferon-inducible protein 6-16, provides evidence that quantitation of one or more of these proteins in protein aggregates in the placenta and/or the urine also has utility in the diagnosis or prognosis of preeclampsia.

Example 4 Assessment of Samples

Antigen and antibody preparation is described in Kayed et al., "Fibril specific, conformation dependent antibodies recognize a generic epitope common to amyloid fibrils and fibrillar oligomers that is absent in prefibrillar oligomers," *Molecular Neurodegeneration* 2007, 2:18 which reads as follows:

Fibril antigens were prepared by stirring 2 mg/ml Aβ42 peptide in 50% HFIP/H2O, 0.02% sodium azide for 7 days. Afterwards, the HFIP was evaporated under a stream of nitrogen and the sample was stirred for an additional 7 days and dialyzed against PBS (molecular weight cut off 10,000 Da). The resulting fibrils were checked by EM and the purity was confirmed by the absence of oligomers using anti-oligomer antibody. The antigens were each used to immunize two New Zealand white rabbits (Pacific Immunology Corp., Ramona, Calif., 92065) according to protocols approved by IACUC. Each rabbit immunized with 500 μl of antigen in complete Freund's adjuvant (CFA), and then boosted twice at four week intervals with 500 μl of antigen in Incomplete Freund's Adjuvant (IFA).

Fibril and oligomer preparation: Aβ fibrils and fibrillar oligomer were prepared by dissolving 0.3 mg of lyophilized Aβ42 in 150 μl of hexafluoro-2-propanol (HFIP) for 10-20 minutes at zoom temperate. The resulting Aβ solution was added to DD H$_2$O in a siliconized Eppendorf tube to 80 μM concentration. After 10-20 min incubation at room temperature, the samples were centrifuged for 15 min. at 14,000×G and the supernatant fraction (pH 2.8-3.5) was transferred to a new siliconized tube and subjected to a gentle stream of N$_2$ for 10 min to evaporate the HFIP. The sample was then stirred at 500 RPM using a Teflon coated micro stir bar for 24 hours at 22° C. This method was originally reported for preparing A11 positive prefibrillar oligomers, but more recent work indicates that it also produces fibrillar oligomers that are OC positive (Kayed et al., "Common structure of soluble amyloid oligomers implies common mechanism of pathogenesis" Science 2003, 300(5618):486-489). Fibrils were separated from fibrillar Aβ42 oligomers by centrifuged at 100,000×G for 1 hour at 4° C. The supernatant containing fibrillar oligomers and pellet fraction containing fibrils were separated and collected. The pellets were resuspended in an equal volume of H$_2$O. Alternatively, 1 mg of lyophilized Aβ42 was dissolved in 200 μl of DMSO and incubated at room temperature for 10-15 minutes to form fibrillar oligomers. The fibrillar oligomers in DMSO were fractionated according to size using a TSK-GEL SuperSW2000 column (Tosoh Bioscience LLC) in 10 mM Phosphate, pH 7.4 at a flow rate of 0.3 ml/min.

Results

Figure 12:
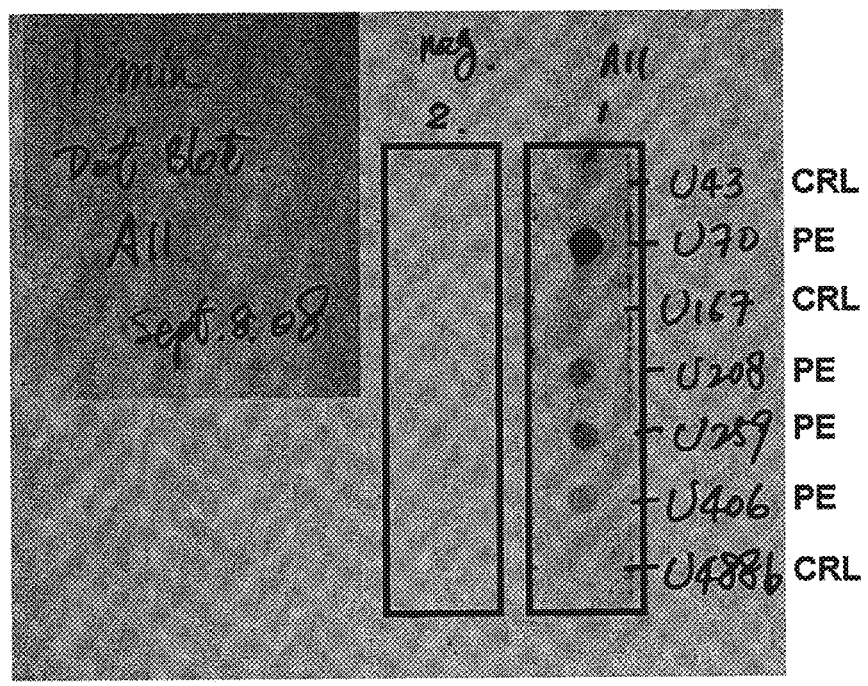
FIG. 12 shows a photograph of a western blot of a nitrocellulose membrane with spotted urine samples (PE: preeclampsia; CRL: control) probed with polyclonal antibody A11 (A11, lane 1) and negative control (neg., lane 2) omitting the primary A11 antibody to control for non-specific binding of the secondary antibody.

Because the A11 antibody is non-selective for oligomeric shapes it was determined that further confirmation using monoclonal antibodies would provide additional useful information. Consequently urine samples that were either A11 positive or negative were tested using a panel of monoclonal antibodies, raised against the same antigen as the A11 antibody (*Science* 300: 486-489, 2003), with preferential affinities for different types of prefibrillar protein oligomer conformations and compared to the A11 antibody. Ten identical strips containing urine samples of women with preeclampsia (PE) or controls (CRL) were generated. FIG. 12 shows A11 immunoreactivity (strip 1) in the laboratory at Yale. Strip 2 was blotted using the same reagents and methods except that the A11 antibody was omitted and served as the control for non-specific binding of the secondary antibodies. The remaining strips were sent to the laboratory at UC Irvine.

Figure 13:
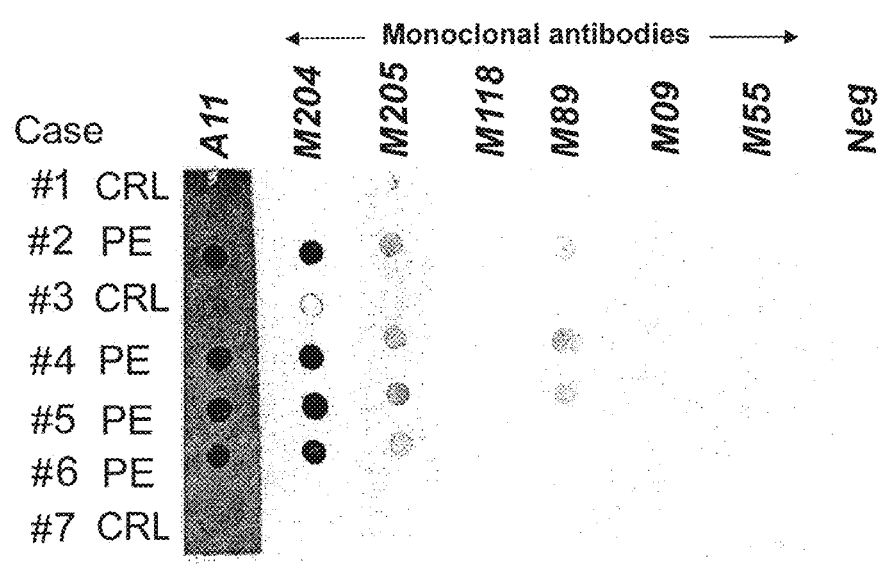
FIG. 13 shows a photograph of a western blot of a nitrocellulose membrane with spotted urine samples (PE: preeclampsia; CRL control) probed with monoclonal antibodies (M204, M205, M118, M89-17, M09, M55) and polyclonal A11 (A11) and negative control (Neg.) omitting the primary antibodies to control for non-specific binding of the secondary antibody.

FIG. 13 shows a photograph of a western blot of a nitrocellulose membrane with spotted urine samples (PE: preeclampsia; CRL: control) probed with monoclonal antibodies (M204, M205, M118, M89, M09, M55) and polyclonal A11 (A11) and negative control (Neg.) omitting the primary antibodies to control for non-specific binding of the secondary antibody. This experiment provided independent confirmation of the immunoreactivity of the A11 antibody to preeclampsia urine samples and demonstrated that some more selective monoclonal antibodies also showed immunoreactivity. These findings show that monoclonal antibodies that recognize different conformations of prefibrillar protein oligomers, such as monoclonal #M204, #M205 and #M89 are useful in the diagnosis of preeclampsia.

Urine samples from women with preeclampsia (PE), but not control cases stained strongly with monoclonal antibody M204 and weakly with monoclonal antibody M205. A subset of the preeclampsia cases also stained with the annular protofibril specific monoclonal M89. Of the samples tested in FIG. 13, the PE case that stained strongest with M89 also was the one that had incipient clinical deterioration consistent with HELLP (Case #4). Conversely, Case #6 (negative for M89) but positive for M204, M205 and A11, is of interest because the diagnosis of severe preeclampsia was based by the sole criterion of pulmonary edema unlike the other PE women who were classified as having severe preeclampsia by blood pressure and/or proteinuria alone. Case #6 subsequently developed peripartum cardiomyopathy which required extensive circulatory support in intensive care unit. The differential pattern of staining with M89 suggests Case #6 may have a distinct etiology and that it may be possible to distinguish these disease forms by immunoreactivity using conformational monoclonals. Anti-Annular Protofibril Monoclonal antibodies, 09 and 89

Example 5 Antibody Production

Two New Zealand white rabbits were vaccinated with an antigen consisting of Aβ1-40 carboxyl terminal thioester covalently bonded to colloidal gold particles via the carboysl terminal sulfur atom. One hundred micrograms of the peptide conjugate antigen was injected with incomplete Freunds adjuvant and boosted with the same antigen at 3 week intervals for approximately 5 months. After the immune response was determined to be equivalent to the A11 antibody immune response, one of the animals was sacrificed, the spleen harvested and the splenic lymphocytes used to produce hybridomas via standard methods known in the art.

After culturing the hybridomas for a sufficient period of time, the supernatants from multiclone wells were screened for the presence of conformation dependent prefibrillar oligomer specific antibodies using Aβ prefibrillar oligomers as a primary screening agent. Aβ monomer, prefibrillar oligomers and fibrils were used as a secondary means of excluding antibodies that are not conformation dependent and interact with all Aβ conformations. Approximately 118 multiclone wells were selected as having immunoreactivity above a criterion of 0.5 AU. These multi clones were sub-cloned and the resulting monoclones were subjected to additional screening and characterization using Aβ40 monomer, prefibrillar oligomer and fibrils.

After secondary screening, clones having a distinct preference for either prefibrillar oligomers or fibrils were selected. Representative clones were selected in comparison to the A11 polyclonal antibody and 6E10, a sequence dependent mouse monoclonal antibody. The conformational and sequence specificity of the clones was analyzed by dot blot Dot blot analysis was conducted by spotting 1 ug of Aβ40 monomer, prefibrillar oligomers and fibrils and 1 ug of prefibrillar oligomers of alpha synuclein, immunoglobin light chain, prion 106-126 peptide, KK(Q40)KK and calcitonin. A11 polyclonal antibody reacts with all types of prefibrillar oligomers, but not Aβ monomer or fibrils. 6E10 recognizes only samples containing AB. Clones 118, 201, 204, 205 and 206 are specific for prefibrillar oligomers and do not recognize monomer or fibrils. This group of clones displays distinct specificities in terms of the other types of prefibrillar oligomers recognized. Clone 121 is specific for Aβ fibrils and does not recognize prefibrillar oligomers of any type or Aβ monomer.

A number of clones appear to secrete antibodies of identical specificity. The most abundant class is similar to clone 201, which only recognize Aβ prefibrillar oligomers and not oligomers of other types. All of these clones are also IgMs. Clone 118 is also indistinguishable from clones 48 mid 55 (data not shown).

The sequences of two of the monoclonal IgGs, 118 and 204 are shown below. The amino acid sequences of the variable regions is distinct, consistent with their different specificities.

118 kappa Vl + Cl
(SEQ ID NO. 7)
AQAAELVMTQTPASVSAAVGGTVTINCQSSESVYNSRLSWFQQKPGQ

PPKLLIYFASTLASGVSSRFSGSGSGTEFTLTISGVQCDDAATYYCA

GHFSNSVYTFGGGTEVVVTGDPVAPTVLIFPPSADLVATGTVTIVCV

ANKYFPDVTVTWEVDGTTQTTGIENSKTPQNSADCTYNLSSTLTLTS

TQYNSHKEYTCKVTQGTTSVVQSFNRGDC*

118 Vh + Clh
(SEQ ID NO. 8)
AAQPAMAQSVEESGGRLVTPGTPLTLTCTVSGFSLSAYEVSWVRQAP

GKGLEWIGIIYANGNTVYASWAKGRFTISKTSTKVDLRIPSPTTEDT

ATYFCARDIYTTTTNLWGPGTLVTVSSGQPKAPSVFPLAPCCGDTHS

STVTLGCLVKGYLPEPVTVTWNSGTLTNGVRTFPSVRQSSGLYSLSS

VVSVTSSSQPVTCNVAHPATNTKVDKTVAPSTCSKTSC

204 kappa Vl + Cll
(SEQ ID NO. 9)
AQAAELDMTQTPASVSEPVGGTVTIKCQASQSISSYLAWYQQKPGQR

PRLLIYETSTLASGVPSRFKGSGSGTEFTLTISDLECADAATYYCQS

TYENPTYVSFGGGTEVGVKGDPVAPTVLIFPPSADLVATGTVTIVCV

ANKYFPDVTVTWEVDGTTQTTGIENSKTPQNSADCTYNLSSTLTLTS

TQYNSHKEYTCKVTQGTTSVVQSFNRGDC*

204 Vh + Clh
(SEQ ID NO. 10)
AAQPAMAQSVKESGGRLVTPGTPLTLACTVSGFSLNTYSMFWVRQAP

GKGLQWIGIISNFGVIYYATWAKGRFTISKTSTTVDLKITSPTTEDT

ATYFCVRKYGSEWGGDLWGPGTLVTVSSGQPKAPSVFPLAPCCGDTP

SSTVTLGCLVKGYLPEPVTVTWNSGTLTNGVRTFPSVRQSSGLYSLS

SVVSVTSSSQPVTCNVAHPATNTKVDKTVAPSTCSKTSC

205 kappa Vl + Cll
(SEQ ID NO. 11)
AQAAELVMTQTPSSVSAAVGGTVTISCQSSESVYNNNYLSWYQQKPG

QPPKRLIDSASTLDSGVPSRFKGSGSGAQFTLTISDLECDDAATYYC

AGAYVNWMRIFGGGTEVVVKGDPVAPTVLIFPPSADLVATGTVTIVC

VANKYFPDVTVTWEVDGTTQTTGIENSKTPQNSADCTYNLSSTLTLT

STQYNSHKEYTCKVTQGTTSVVQSFNRGDC*

205 Vh + Clh
(SEQ ID NO. 12)
MAQSVEESGGRLVTPGTPLTLTCTASGFSLINYYMNWVRQAPGKGLE

WIGLITGWADTYYANSAKGRFTISKTSSTTVDLKITSPTTDDTATYF

CVRGGHTNIISLWGPGTLVTVSSGQPKAPSVFPLPPCCGDTPSSTVT

LGCLVKGYLPEPVTVTWNSGTLTNGVRIFPSVRQSSGLYSLSSVVSV

TSSSQPVTCNVAHPATNTKVDKTVAPSTCSKTSC

Monoclonal Antibodies Specific for Aβ Oligomers and Fibrils:

Even though the polyclonal immune response to different assembly states of amyloid is remarkably specific, monoclonal antibodies offer unique advantages in terms of defining fine structural variation in amyloid aggregates and for determining the structures of these aggregates and their pathological significance. We initially focused on antibodies against prefibrillar amyloid epitopes, but vaccinating mice with the colloidal gold coupled AD that we used to make A11. We tried to produce mouse monoclonal antibodies by contract with two different vendors using 4 different strains of mice. Even though we obtained good titers of conformation dependent IgGs in the polyclonal mouse serum, we were only able to clone IgM secreting hybridomas from the fusion products of mouse splenocytes. We tried different routes of vaccination, vaccination for 6 months and different sources of lymphocytes (peripheral and lymph node) but were never able to clone anything but IgMs. The reasons for the failure to clone IgG secreting clones from mouse hybridomas remain unclear. While these IgMs may have some utility, they are not as desirable for many applications, so we contracted to make monoclonal IgGs in rabbits by contracting with Epitomics, Inc. Although we used the same antigens and screening that we used for mouse monoclonals, we obtained many more positive independent clones (>200), many of which are IgGs (data not shown). Many of these clones appear to be phenotypically identical and fall in to one of 6 distinct classes that we have identified so far (FIG. 1).

The specificity of the monoclonal antibodies we obtained is interesting for several reasons (FIG. 1). All of the monoclonals obtained in response to vaccination with the A11 Aβ C-terminal thioester colloidal gold antigen are conformation specific even though we selected all clones that reacted with Aβ monomer, oligomers and fibrils. None of the clones recognize monomer like 6E10. This indicates that the immune response to the solid phase antigen is highly conformation specific. None of the antibodies recognize both pure fibril and pure oligomer samples, indicating that the distribution of these epitopes is mutually exclusive. Secondly, most of the antibodies (M118, M204, M206, M206) recognize "generic epitopes" that are distributed on prefibrillar oligomers produced from other protein and peptide sequences. However, within this class of antibodies that recognize "generic" prefibrillar oligomer epitopes there is considerable variation in the types of oligomers that the antibody recognizes. All of the generic monoclonals recognize Aβ oligomers because they were used as the primary screen, but each antibody has a specificity more restricted than the A11 polyclonal immune response. For example, M204 strongly recognizes most types of oligomers, but it is distinctly less reactive with immunoglobulin light chain oligomers. M205 reacts strongly with alpha synuclein and light chain oligomers, but does not react will with prion 106-126, polyQ and calcitonin oligomers. M118 prefers light chain and polyQ oligomers, but not synuclein, prion or calcitonin oligomers. These results indicate that there are multiple distinct epitopes associated with prefibrillar oligomers that are widely distributed within this class and that monoclonal antibodies can recognize these unique epitopes. Thirdly, some monoclonals are both conformation dependent and sequence specific. M201 recognizes only Aβ oligomers, while M121 only recognizes Aβ fibrils. M118, M204 and M205 are IgG, while the other antibodies are IgM.

Example 6

Monoclonals were made in rabbits under contract with Epitomics, Inc. New Zealand white rabbits were immunized with A842 annular protofibrils prepared as described in Kayed et al., J. Biol. Chem. 2009 (1). Homogenous populations of AB annular protofibrils were prepared by using Aβ prefibrillar oligomers as the starting material that were prepared as previously described (2). APFs were prepared by adding 5% (vol/vol) hexane to the solution of prefibrillar oligomers and the sample was mixed with a vortex mixer for 1 min every 5 min for a total 50 min. Afterwards, the samples were dialyzed in water, using a MW cut-off membrane of 10 kDa. Rabbits were vaccinated a total of 7 times at 3 week intervals with 500 ug of Aβ annular protofibrils. The serum was screened for annular protofibril specific titer and the rabbit with the highest titer was chosen for monoclonal production. The supernatants from the resulting hybridomas were initially screened by ELISA with Aβ annular protofibrils, Aβ fibrils and Aβ monomer. Wells that produced an optical density of greater than 1.0 on annular protofibrils and background reactivity on Aβ fibrils and monomer were chosen for secondary screening. Approximately 100 wells were chosen for secondary screening against Aβ annular profibrils (APFs), alpha hemolysin pores, Aβ fibrils, Aβ prefibrillar oligomers, Aβ monomer and Aβ in 0.1% SDS using dot blotting. The results are shown below.

In the secondary screen, monoclonals 09 and 89 only reacted with the alpha hemolysin pores. We also characterized their immunoreactivity against alpha hemolysin and Aβ dissolved in 10 mM NaOH by western blotting as shown below.

Both monoclonal antibodies 09 and 87 were found to react with a band at approximately 65 kDa on Westerns. M87 also reacts with a band at approximately 40 kDa. The bend of alpha hemolysin at 65 kDa also reacts strongly with the polyclonal serum from the rabbit that the monoclonals were prepared from.

1. Kayed, R, A. Pensalfini, L. Margol, Y. Sokolov, F. Sarsoza, E. Head, J. Hall, and C. Glabe. 2009. Annular protofibrils are a structurally and functionally distinct type of amyloid oligomer. *J Biol Chem* 284:4230-4237.
2. Kayed, R., and C. G. Glabe. 2006. Conformation-dependent anti-amyloid oligomer antibodies. *Methods Enzymol* 413:326-344.

The practice of the present invention will employ, unless otherwise indicated, conventional techniques of cell biology, cell culture, molecular biology, microbiology, recombinant DNA, and immunology, which are within the skill of the art. Such techniques are described in the literature.

This invention is not limited in its application to the details of construction and the arrangement of components set forth in the description or illustrated in the drawings. The invention is capable of other embodiments and of being practiced or of being carried out in various ways. The phraseology and terminology used herein is for the purpose of description and should not be regarded us limiting. The use of "including," "comprising," or "having," "containing," "involving," and variations thereof herein, is meant to encompass the items listed thereafter and equivalents thereof as well as additional items.

What is claimed is:

1. A method comprising:
   combining a urine sample obtained from a female subject with an A11 antibody that binds specifically to soluble pre-amyloid oligomers; and
   assaying the sample for the presence or absence of the A11 antibody bound to soluble pre-amyloid oligomers.

2. The method of claim 1, wherein the female subject is a pregnant female subject.

3. The method of claim 1, wherein the female subject is a human female subject.

4. The method of claim 3, wherein the human female subject is a pregnant human female subject.

5. The method of claim 3, wherein the human female subject is a postpartum human female subject.

6. A method comprising:
   combining a placental sample obtained from a female subject with an OC antibody that binds specifically to amyloid fibrils; and
   assaying the sample for the presence or absence of the OC antibody bound to amyloid fibrils.

7. The method of claim 6, wherein the female subject is a pregnant female subject.

8. The method of claim 6, wherein the female subject is a human female subject.

9. The method of claim 8, wherein the human female subject is a pregnant human female subject.

10. The method of claim 8, wherein the human female subject is a postpartum human female subject.

* * * * *

SEQUENCE LISTING

```
<160> NUMBER OF SEQ ID NOS: 15

<210> SEQ ID NO 1
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1

Met Ile Glu Gln Asn Thr Lys Ser Pro Leu Phe Met Gly Lys Val Val
```

Asn Pro Thr Gln Lys
        20

<210> SEQ ID NO 2
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Oxidized methionine

<400> SEQUENCE: 2

Met Ile Glu Gln Asn Thr Lys Ser Pro Leu Phe Met Gly Lys Val Val
1               5                   10                  15

Asn Pro Thr Gln Lys
        20

<210> SEQ ID NO 3
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Oxidized methionine
<220> FEATURE:
<221> NAME/KEY: MISC_FEATURE
<222> LOCATION: (12)..(12)
<223> OTHER INFORMATION: Oxidized methionine

<400> SEQUENCE: 3

Met Ile Glu Gln Asn Thr Lys Ser Pro Leu Phe Met Gly Lys Val Val
1               5                   10                  15

Asn Pro Thr Gln Lys
        20

<210> SEQ ID NO 4
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 4

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
        20                  25                  30

Phe Ala Phe Ser
        35

<210> SEQ ID NO 5
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 5

Asp Ala His Lys Ser Glu Val Ala His Arg Phe Lys Asp Leu Gly Glu

-continued

```
<210> SEQ ID NO 6
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala
            20                  25

<210> SEQ ID NO 7
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 7

Ala Gln Ala Ala Glu Leu Val Met Thr Gln Thr Pro Ala Ser Val Ser
1               5                   10                  15

Ala Ala Val Gly Gly Thr Val Thr Ile Asn Cys Gln Ser Ser Glu Ser
            20                  25                  30

Val Tyr Asn Ser Arg Leu Ser Trp Phe Gln Gln Lys Pro Gly Gln Pro
        35                  40                  45

Pro Lys Leu Leu Ile Tyr Phe Ala Ser Thr Leu Ala Ser Gly Val Ser
    50                  55                  60

Ser Arg Phe Ser Gly Ser Gly Ser Gly Thr Glu Phe Thr Leu Thr Ile
65                  70                  75                  80

Ser Gly Val Gln Cys Asp Asp Ala Ala Thr Tyr Tyr Cys Ala Gly His
                85                  90                  95

Phe Ser Asn Ser Val Tyr Thr Phe Gly Gly Gly Thr Glu Val Val Val
            100                 105                 110

Thr Gly Asp Pro Val Ala Pro Thr Val Leu Ile Phe Pro Pro Ser Ala
        115                 120                 125

Asp Leu Val Ala Thr Gly Thr Val Thr Ile Val Cys Val Ala Asn Lys
    130                 135                 140

Tyr Phe Pro Asp Val Thr Val Thr Trp Glu Val Asp Gly Thr Thr Gln
145                 150                 155                 160

Thr Thr Gly Ile Glu Asn Ser Lys Thr Pro Gln Asn Ser Ala Asp Cys
                165                 170                 175

Thr Tyr Asn Leu Ser Ser Thr Leu Thr Leu Thr Ser Thr Gln Tyr Asn
            180                 185                 190

Ser His Lys Glu Tyr Thr Cys Lys Val Thr Gln Gly Thr Thr Ser Val
        195                 200                 205

Val Gln Ser Phe Asn Arg Gly Asp Cys
    210                 215

<210> SEQ ID NO 8
<211> LENGTH: 226
<212> TYPE: PRT
<213> ORGANISM: Artificial Sequence
<220> FEATURE:
```

<223> OTHER INFORMATION: Synthetic Polypeptide

<400> SEQUENCE: 8

Ala Ala Gln Pro Ala Met Ala Gln Ser Val Glu Glu Ser Gly Gly Arg
1               5                   10                  15

Leu Val Thr Pro Gly Thr Pro Leu Thr Leu Thr Cys Thr Val Ser Gly
            20                  25                  30

Phe Ser Leu Ser Ala Tyr Glu Val Ser Trp Val Arg Gln Ala Pro Gly
        35                  40                  45

Lys Gly Leu Glu Trp Ile Gly Ile Ile Tyr Ala Asn Gly Asn Thr Val
    50                  55                  60

Tyr Ala Ser Trp Ala Lys Gly Arg Phe Thr Ile Ser Lys Thr Ser Thr
65                  70                  75                  80

Lys Val Asp Leu Arg Ile Pro Ser Pro Thr Thr Glu Asp Thr Ala Thr
                85                  90                  95

Tyr Phe Cys Ala Arg Asp Ile Tyr Thr Thr Thr Asn Leu Trp Gly
            100                 105                 110

Pro Gly Thr Leu Val Thr Val Ser Ser Gly Gln Pro Lys Ala Pro Ser
            115                 120                 125

Val Phe Pro Leu Ala Pro Cys Cys Gly Asp Thr His Ser Ser Thr Val
130                 135                 140

Thr Leu Gly Cys Leu Val Lys Gly Tyr Leu Pro Glu Pro Val Thr Val
145                 150                 155                 160

Thr Trp Asn Ser Gly Thr Leu Thr Asn Gly Val Arg Thr Phe Pro Ser
                165                 170                 175

Val Arg Gln Ser Ser Gly Leu Tyr Ser Leu Ser Ser Val Val Ser Val
            180                 185                 190

Thr Ser Ser Ser Gln Pro Val Thr Cys Asn Val Ala His Pro Ala Thr
        195                 200                 205

Asn Thr Lys Val Asp Lys Thr Val Ala Pro Ser Thr Cys Ser Lys Thr
    210                 215                 220

Ser Cys
225

<210> SEQ ID NO 9
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 9

Ala Gln Ala Ala Glu Leu Asp Met Thr Gln Thr Pro Ala Ser Val Ser
1               5                   10                  15

Glu Pro Val Gly Gly Thr Val Thr Ile Lys Cys Gln Ala Ser Gln Ser
            20                  25                  30

Ile Ser Ser Tyr Leu Ala Trp Tyr Gln Gln Lys Pro Gly Gln Arg Pro
        35                  40                  45

Arg Leu Leu Ile Tyr Glu Thr Ser Thr Leu Ala Ser Gly Val Pro Ser
    50                  55                  60

Arg Phe Lys Gly Ser Gly Ser Gly Thr Glu Phe Thr Leu Thr Ile Ser
65                  70                  75                  80

Asp Leu Glu Cys Ala Asp Ala Ala Thr Tyr Tyr Cys Gln Ser Thr Tyr
                85                  90                  95

Glu Asn Pro Thr Tyr Val Ser Phe Gly Gly Gly Thr Glu Val Gly Val
            100                 105                 110

```
Lys Gly Asp Pro Val Ala Pro Thr Val Leu Ile Phe Pro Pro Ser Ala
        115                 120                 125

Asp Leu Val Ala Thr Gly Thr Val Thr Ile Val Cys Val Ala Asn Lys
130                 135                 140

Tyr Phe Pro Asp Val Thr Val Thr Trp Glu Val Asp Gly Thr Thr Gln
145                 150                 155                 160

Thr Thr Gly Ile Glu Asn Ser Lys Thr Pro Gln Asn Ser Ala Asp Cys
                165                 170                 175

Thr Tyr Asn Leu Ser Ser Thr Leu Thr Leu Thr Ser Thr Gln Tyr Asn
                180                 185                 190

Ser His Lys Glu Tyr Thr Cys Lys Val Thr Gln Gly Thr Thr Ser Val
                195                 200                 205

Val Gln Ser Phe Asn Arg Gly Asp Cys
210                 215
```

<210> SEQ ID NO 10
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 10

```
Ala Ala Gln Pro Ala Met Ala Gln Ser Val Lys Glu Ser Gly Gly Arg
1               5                   10                  15

Leu Val Thr Pro Gly Thr Pro Leu Thr Leu Ala Cys Thr Val Ser Gly
                20                  25                  30

Phe Ser Leu Asn Thr Tyr Ser Met Phe Trp Val Arg Gln Ala Pro Gly
            35                  40                  45

Lys Gly Leu Gln Trp Ile Gly Ile Ile Ser Asn Phe Gly Val Ile Tyr
    50                  55                  60

Tyr Ala Thr Trp Ala Lys Gly Arg Phe Thr Ile Ser Lys Thr Ser Thr
65                  70                  75                  80

Thr Val Asp Leu Lys Ile Thr Ser Pro Thr Thr Glu Asp Thr Ala Thr
                85                  90                  95

Tyr Phe Cys Val Arg Lys Tyr Gly Ser Glu Trp Gly Gly Asp Leu Trp
            100                 105                 110

Gly Pro Gly Thr Leu Val Thr Val Ser Ser Gly Gln Pro Lys Ala Pro
        115                 120                 125

Ser Val Phe Pro Leu Ala Pro Cys Cys Gly Asp Thr Pro Ser Ser Thr
130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                165                 170                 175

Ser Val Arg Gln Ser Ser Gly Leu Tyr Ser Leu Ser Ser Val Val Ser
                180                 185                 190

Val Thr Ser Ser Ser Gln Pro Val Thr Cys Asn Val Ala His Pro Ala
                195                 200                 205

Thr Asn Thr Lys Val Asp Lys Thr Val Ala Pro Ser Thr Cys Ser Lys
                210                 215                 220

Thr Ser Cys
225
```

<210> SEQ ID NO 11

-continued

```
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 11

Ala Gln Ala Ala Glu Leu Val Met Thr Gln Thr Pro Ser Ser Val Ser
1               5                   10                  15

Ala Ala Val Gly Gly Thr Val Thr Ile Ser Cys Gln Ser Ser Glu Ser
            20                  25                  30

Val Tyr Asn Asn Asn Tyr Leu Ser Trp Tyr Gln Gln Lys Pro Gly Gln
        35                  40                  45

Pro Pro Lys Arg Leu Ile Asp Ser Ala Ser Thr Leu Asp Ser Gly Val
    50                  55                  60

Pro Ser Arg Phe Lys Gly Ser Gly Ser Gly Ala Gln Phe Thr Leu Thr
65                  70                  75                  80

Ile Ser Asp Leu Glu Cys Asp Asp Ala Ala Thr Tyr Tyr Cys Ala Gly
                85                  90                  95

Ala Tyr Val Asn Trp Met Arg Ile Phe Gly Gly Gly Thr Glu Val Val
            100                 105                 110

Val Lys Gly Asp Pro Val Ala Pro Thr Val Leu Ile Phe Pro Pro Ser
        115                 120                 125

Ala Asp Leu Val Ala Thr Gly Thr Val Thr Ile Val Cys Val Ala Asn
    130                 135                 140

Lys Tyr Phe Pro Asp Val Thr Val Thr Trp Glu Val Asp Gly Thr Thr
145                 150                 155                 160

Gln Thr Thr Gly Ile Glu Asn Ser Lys Thr Pro Gln Asn Ser Ala Asp
                165                 170                 175

Cys Thr Tyr Asn Leu Ser Ser Thr Leu Thr Leu Thr Ser Thr Gln Tyr
            180                 185                 190

Asn Ser His Lys Glu Tyr Thr Cys Lys Val Thr Gln Gly Thr Thr Ser
        195                 200                 205

Val Val Gln Ser Phe Asn Arg Gly Asp Cys
    210                 215

<210> SEQ ID NO 12
<211> LENGTH: 222
<212> TYPE: PRT
<213> ORGANISM: Artificial Sequence
<220> FEATURE:
<223> OTHER INFORMATION: Synthetic Polypeptide

<400> SEQUENCE: 12

Met Ala Gln Ser Val Glu Glu Ser Gly Gly Arg Leu Val Thr Pro Gly
1               5                   10                  15

Thr Pro Leu Thr Leu Thr Cys Thr Ala Ser Gly Phe Ser Leu Ile Asn
            20                  25                  30

Tyr Tyr Met Asn Trp Val Arg Gln Ala Pro Gly Lys Gly Leu Glu Trp
        35                  40                  45

Ile Gly Leu Ile Thr Gly Trp Ala Asp Thr Tyr Tyr Ala Asn Ser Ala
    50                  55                  60

Lys Gly Arg Phe Thr Ile Ser Lys Thr Ser Ser Thr Val Asp Leu
65                  70                  75                  80

Lys Ile Thr Ser Pro Thr Thr Asp Asp Thr Ala Thr Tyr Phe Cys Val
                85                  90                  95

Arg Gly Gly His Thr Asn Ile Ile Ser Leu Trp Gly Pro Gly Thr Leu
```

```
                    100                 105                 110
Val Thr Val Ser Ser Gly Gln Pro Lys Ala Pro Ser Val Phe Pro Leu
                115                 120                 125

Pro Pro Cys Cys Gly Asp Thr Pro Ser Ser Thr Val Thr Leu Gly Cys
            130                 135                 140

Leu Val Lys Gly Tyr Leu Pro Glu Pro Val Thr Val Thr Trp Asn Ser
145                 150                 155                 160

Gly Thr Leu Thr Asn Gly Val Arg Ile Phe Pro Ser Val Arg Gln Ser
                165                 170                 175

Ser Gly Leu Tyr Ser Leu Ser Ser Val Val Ser Val Thr Ser Ser Ser
            180                 185                 190

Gln Pro Val Thr Cys Asn Val Ala His Pro Ala Thr Asn Thr Lys Val
                195                 200                 205

Asp Lys Thr Val Ala Pro Ser Thr Cys Ser Lys Thr Ser Cys
            210                 215                 220

<210> SEQ ID NO 13
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 13

Lys Lys Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Lys Lys
        35                  40                  45

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 14

Phe Leu Glu Ala Ile Gly
1               5

<210> SEQ ID NO 15
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 15

Lys Lys Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln Gln Gln Gln Gln Lys Lys
        35                  40
```